US006306830B1

(12) United States Patent
Hammond et al.

(10) Patent No.: US 6,306,830 B1
(45) Date of Patent: Oct. 23, 2001

(54) GENE THERAPY FOR CONGESTIVE HEART FAILURE

(75) Inventors: H. Kirk Hammond, La Jolla; Paul A. Insel, San Diego, both of CA (US); Peipei Ping, Jeffersonville, IN (US); Steven R. Post, Lexington, KY (US); Meihua Gao, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/008,097

(22) Filed: Jan. 16, 1998

Related U.S. Application Data

(63) Continuation-in-part of application No. 08/924,757, filed as application No. PCT/US97/15610 on Sep. 5, 1997, now abandoned.
(60) Provisional application No. 60/048,933, filed on Jun. 16, 1997, and provisional application No. 60/058,209, filed on Sep. 5, 1996.

(51) Int. Cl.[7] ........................... A61K 48/00; A61K 35/00; C12N 15/63; C12N 7/00
(52) U.S. Cl. ..................... 514/44; 435/320.1; 435/235.1; 424/93.2
(58) Field of Search ............................. 514/44; 424/93.1, 424/93.12, 93.2; 435/320.1, 325, 91.4, 455, 235.1

(56) References Cited

U.S. PATENT DOCUMENTS

| | | |
|---|---|---|
| 5,334,521 | 8/1994 | Ishikawa . |
| 5,578,481 | 11/1996 | Ishikawa . |
| 5,792,453 * | 8/1998 | Hammond et al. ................ 424/93.21 |
| 6,034,071 * | 3/2000 | Iyengar ................................ 514/44 |

FOREIGN PATENT DOCUMENTS

| | | |
|---|---|---|
| WO 92/08796 | 5/1992 | (WO) . |
| WO 93/05061 | 3/1993 | (WO) . |
| WO 94/11506 | 5/1994 | (WO) . |
| WO 94/28143 | 12/1994 | (WO) . |
| WO 96/08260 | 3/1996 | (WO) . |
| WO 96/17947 | 6/1996 | (WO) . |
| WO 97/12050 | 4/1997 | (WO) . |
| WO 97/16169 | 5/1997 | (WO) . |
| WO 99/01546 | 1/1999 | (WO) . |
| WO 99/01547 | 1/1999 | (WO) . |

OTHER PUBLICATIONS

Miller FASEB J., vol. 9, pp. 190–199, 1995.*
Deonarain Expert Opin. Ther. Pat., vol. 8, pp. 53–69, 1998.*
Verma Nature, vol. 389, pp. 239–242, Sep. 1997.*
Crystal Science, vol. 270, p. 404–410, 1995.*
Ping et al. Circulation, vol. 92, p. 570, abstract 2727, Oct. 1995.*
Katsushika et al., PNAS, vol. 89, pp. 8774–8778, 1992.*
Tang et al., Biochemistry, vol. 34, p. 14563–14572, 1995.*
Alousi et al., "Stoichiometry of receptor–$G_S$–adenylate cyclase interactions" *FASEB J.* (1991) 5:2300–2304.
Brigham et al., "Cationic liposomes and DNA delivery" *J. Liposome Res.* (1993) 3:31–49.
Bristow et al., "$\beta_1$ and $\beta_2$–adrenergic receptor–mediated adenylate cyclase stimulation in nonfailing and failing human ventricular myocardium" *Mol. Pharm.* (1989) 35:295–303.
Bristow et al., "Reduced $\beta_1$ receptor messenger RNA abundance in the failing human heart" *J. Clin. Invest.* (1993) 92:2737–2745.
Burns et al., "Vesicular stomatitis virus G glycoprotein pseudotyped retroviral vectors: Concentration to very high titer and efficient gene transfer into mammalian and non-mammalian cells" *Proc. Natl. Acad. Sci. (USA)* (1993) 90:8033–8037.
Carter, "Adeno–associated virus vectors" *Curr. Opin. Biotechnol.* (1992) 3:533–539.
Darfler et al., "Stimulation by forskolin of intact S49 lymphoma cells involves the nucleotide regulatory protein of adenylate cyclase" *J. Biol. Chem.* (1982) 257:11901–11907.
Flotte et al., "Adeno–associated virus vectors for gene therapy" *Gene Therapy* (1995) 2:357–362.
Frielle et al., "Cloning of the cDNA for the human $\beta_1$–adrenergic receptor" *Proc. Natl. Acad. Sci. (USA)* (1987) 84:7920–7924.
Gao et al., "Increased adrenergic signaling after adenylylcyclase type VI gene transfer in rat cardiac myocytes" *Circulation*(1997) 6:I–294, XP–002056511.
Hammond et al., "Regional myocardial downregulation of the inhibitory guanosine triphosphate–binding protein (($Gi\alpha_2$)and $\beta$–adrenergic receptors in a porcine model of chronic episodic myocardial ischemia" *J. Clin. Invest.* (1993) 92:2644–2652.
Inglese et al., "Structure and mechanism of the G protein–coupled receptor kinases" *J. Biol. Chem.* (1993) 268:23735–23738.
Ishikawa et al., "Isolation and characterization of a novel cardiac adenylylcyclase cDNA" *J. Biol. Chem.* (1992) 267:13553–13557.
Ishikawa et al., "Downregulation of adenylylcyclase types V and VI mRNA levels in pacing–induced heart failure in dogs" *J. Clin. Invest.* (1994) 93:2224–2229.

(List continued on next page.)

Primary Examiner—Deborah J. R. Clark
Assistant Examiner—Michael C. Wilson
(74) *Attorney, Agent, or Firm*—Morrison & Foerster, LLP

(57) ABSTRACT

The present invention relates to methods and compositions for enhancing cardiac function in mammalian hearts by inserting transgenes that increase $\beta$-adrenergic responsiveness within the myocardium. The present invention can thus be used in the treatment of heart disease, especially congestive heart failure.

27 Claims, 14 Drawing Sheets

OTHER PUBLICATIONS

Iyengar, "Molecular and functional diversity of mammalian $G_S$–stimulated adenylyl cyclases" *FASEB J.* (1993) 7:768–775.

Katsushika et al., "Cloning and characterization of a sixth adenylyl cyclase isoform: Types V and VI constitute a subgroup within the mammalian adenylyl cyclase family" *Proc. Natl. Acad. Sci. (USA)* (1992) 89:8774–8778.

Koch et al., "Cardiac function in mice overexpressing the β–adrenergic receptor kinase or a βARK inhibitor" *Science* (1995) 268:1350–1353.

Krupinski et al., "Molecular diversity in the adenylylclase family: Evidence for eight forms of the enzyme and cloning of type VI" *J. Biol. Chem.* (1992) 267:24858–24862.

Lee et al., "Myosin light chain–2 luciferase transgenic mice reveal distinct regulatory programs for cardiac and skeletal muscle–specific expression of a single contractile protein gene" *J. Biol. Chem.* (1992) 267:15875–15885.

McGrory et al., "Short communications. A simple technique for the rescue of early region I mutations into infectious human adenovirus type 5" *Virology* (1988) 163:614–617.

Miller et al., "Targeted vectors for gene therapy" *FASEB J.* (1995) 9:190–199.

Nabel E., "Gene therapy for cardiovascular disease" *Circulation* (1995) 91:541–548.

Ping et al., "Over–expression of adenylylclase VI ($AC_{VI}$) increases β–adrenergic receptor–stimulated cAMP in neonatal rat cardiac myocytes" *Circulation* (1995) 92:2727.

Ping et al., "Reduced β–adrenergic receptor activation decreases G–protein expression and β–adrenergic receptor kinase activity in porcine heart" *J. Clin. Invest.* (1995) 95:1271–1280.

Roth et al., "Downregulation of cardiac guanosine 5'–triphosphate–binding proteins in right atrium and left ventricle in pacing–induced congestive heart failure" *J. Clin. Invest.* (1993) 91:939–949.

Salomon et al., "A highly sensitive adenylate cyclase assay" *Anal. Biochem.* (1974) 58:541–548.

Spinale et al., "Relation between ventricular and myocyte remodeling with the development and regression of supraventricular tachycardia–induced cardiomyopathy" *Circ. Res.* (1991) 69:1058–1067.

Summers et al., "Signalling pathways in cardiac failure" *Clin. Exper. Pharm. Phys.* (1995) 22:874–876.

Ungerer et al., "Altered expression of β–adrenergic receptor kinase and $β_1$–adrenergic receptors in the failing human heart" *Circulation* (1993) 87:454–463.

Ungerer et al., "Expression of β–arrestins and β–adrenergic receptor kinases in the failing human heart" *Circ Res* (1994) 74:206–213.

Yoshimura et al., "Cloning and expression of a $Ca^{2+}$–inhibitable adenylyl cyclase from NCB–20 cells" *Proc. Natl. Acad. Sci.(USA)* (1992) 89:6716–6720.

Avidor–Reiss, et al., "Opiate–induced adenylyl cyclase superactivation is isozyme–specific," *J. Biol. Chem.* 272(8):5040–7 (1997).

Premont et al., "Two members of a widely expressed subfamily of hormone–stimulated adenylyl cyclases," *Proc. Natl. Acad. Sci. U.S.A.* 89(20):9809–13 (1992).

Thomas, J.M., "Isoform–specific sensitization of adenylyl cyclase activity by prior activation of inhibitory receptors:role of beta gamma subunits in transducing enhanced activity of the type VI isoform," *Mol. Pharmacol.* 49(5):907–14 (1996).

* cited by examiner

$AC_{VI}$ mRNA IN CARDIAC MYOCYTES

GENE THERAPY FOR CONGESTIVE HEART FAILURE

CROSS REFERENCES TO RELATED APPLICATIONS

This application is a continuation-in-part of U.S. patent application Ser. No. 08/924,757, filed Sep. 5, 1997, now abandoned and PCT/US97/15610, filed Sep. 5, 1977, each of which claimed priority to provisional U.S. patent application Ser. No. 60/048,933, filed Jun. 16, 1997, and to U.S. patent application Ser. No. 08/708,661, filed Sep. 5, 1996 (which was subsequently converted to provisional U.S. patent application Ser. No. 60/058,209), all of which are incorporated by reference herein.

STATEMENT REGARDING GOVERNMENT-SPONSORED RESEARCH

This invention was made with U.S. Government support under Grant Nos. HL0281201 and 1P50HL53773-01, awarded by the National Institutes of Health. The U.S. Government may have certain rights in this invention.

FIELD OF THE INVENTION

The present invention relates to methods and compositions for enhancing cardiac function in mammalian hearts, more specifically, the invention relates to techniques and polynucleotide constructs for enhancing myocardial β-adrenergic responsiveness using in vivo gene therapy.

BACKGROUND

It has been reported that 3–4 million adults in the United States have congestive heart failure (abbreviated "CHF" herein); and the incidence of CHF is increasing (see, e.g., Baughman, K., Cardiology Clinics 13: 27–34, 1995). Annually in US hospitals, CHF is the most frequent non-elective admission and the discharge diagnosis for 500,000 patients. Once symptoms of heart failure are moderately severe, the prognosis is worse than most cancers in that 50% of such patients are dead within 2 years (Braunwald, E. (ed), In: Heart Disease, W. B. Saunders, Philadelphia, page 471–485, 1988). Although medical therapy can initially attenuate the symptoms of heart failure (edema, breathlessness, fluid in the lungs), and in some cases prolong life, the prognosis in this disease, even with medical treatment, is grim (see, e.g., Baughman, K., Cardiology Clinics 13: 27–34, 1995).

CHF is defined as abnormal heart function resulting in inadequate cardiac output for metabolic needs (Braunwald, E. led), In: Heart Disease, W. B. Saunders, Philadelphia, page 426, 1988). Symptoms include breathlessness, fatigue, weakness, leg swelling, and exercise intolerance. On physical examination, patients with heart failure tend to have elevations in heart and respiratory rates, rales (an indication of fluid in the lungs), edema, jugular venous distension, and, in general, enlarged hearts. The most common cause of CHF is atherosclerosis which causes blockages in the blood vessels (coronary arteries) that provide blood flow to the heart muscle. Ultimately such blockages may cause myocardial infarction (death of heart muscle) with subsequent decline in heart function and resultant heart failure. Other causes of CHF include valvular heart disease, hypertension, viral infections of the heart, alcohol, and diabetes. Some cases of heart failure occur without clear etiology and are called idiopathic.

CHF is also typically accompanied by alterations in one or more aspects of β-adrenergic neurohumoral function; see, e.g., Bristow M R, et al., N Engl J Med 307:205–211, 1982; Bristow M R, et al., Circ Res 59:297–309, 1986; Ungerer M, et al., Circulation 87: 454–461, 1993; Feldman A M, et al., J Clin Invest 82:189–197, 1988; Bristow M R, et al., J Clin Invest 92: 2737–2745, 1993; Calderone A, et al., Circ Res 69:332–343. 1991; Marzo K P, et al., Circ Res 69:1546–1556, 1991; Liang C-S, et al., J Clin Invest 84: 1267–1275, 1989; Roth D A, et al., J Clin Invest 91: 939–949, 1993; Hadcock J R and Malbon C C: Proc Natl Acad Sci 85:5021–5025, 1988; Hadcock J R, et al., J Biol Chem 264: 19928–19933, 1989; Mahan, et al., Proc Natl Acad Sci USA 82:129–133, 1985; Hammond H K, et al., Circulation 85:269–280, 1992; Neumann J, et al., Lancet 2: 936–937, 1988; Urasawa K, et al., In: G Proteins: Signal Transduction and Disease, Academic Press, London. 44–85, 1992; Bohm M, Mol Cell Biochem, 147: 147–160, 1995; Eschenhage T, et al., Z Kardiol, 81 (Suppl 4): 33–40, 1992; and Yamamoto J, et al., J Mol Cell, 26: 617–626, 1994. See also the numerous additional references regarding various adenylylcyclase enzymes by, e.g., Fujita M et al., Circulation, 90: (No. 4 Part 2), 1994; Yoshimura M et al., Proc Natl Acad Sci USA, 89:6716–6720, 1992; Krupinski J et al., J Biol Chem, 267:24858–24862, 1992; Ishikawa Y et al., J Biol Chem, 267:13553–13557, 1992; Ishikawa Y et al., J. Clin Invest, 93:2224–2229, 1994; Katsushika S et al., Proc Natl Acad Sci USA, 89:8774–8778, 1992; Wallach J et al., FEBS Lett, 338:257–263, 1994; Watson P A et al., J Biol Chem, 269:28893–28898, 1994; Manolopoulos V G et al., Biochem Biophys Res Commun, 208:323–331, 1995; Yu H J et al., FEBS Lett, 374:89–94, 1995; and Chen Z et al., J Biol Chem, 270:27525–27530, 1995.

As a result of these studies and others, efforts to treat CHF have focused on the administration of pharmacological agents, such as catecholamines and other β-adrenergic agonists, as means of stimulating β-adrenergic responses in dysfunctional hearts. Such therapeutic approaches have been only partly successful. Furthermore, long-term exposure to catecholamines can be detrimental. In particular, the heart tends to become less responsive to β-adrenergic stimulation, and such unresponsiveness is typically associated with high levels of catecholamines in plasma, a factor generally linked to a poor prognosis.

Present treatments for CHF include pharmacological therapies, coronary revascularization procedures (e.g. coronary artery bypass surgery and angioplasty), and heart transplantation. Pharmacological therapies have been directed toward increasing the force of contraction of the heart (by using inotropic agents such as digitalis and β-adrenergic receptor agonists), reducing fluid accumulation in the lungs and elsewhere (by using diuretics), and reducing the work of the heart (by using agents that decrease systemic vascular resistance such as angiotensin converting enzyme inhibitors). β-adrenergic receptor antagonists have also been tested. While such pharmacological agents can improve symptoms, and potentially prolong life, the prognosis in most cases remains dismal.

Some patients with heart failure due to associated coronary artery disease can benefit, at least temporarily, by revascularization procedures such as coronary artery bypass surgery and angioplasty. Such procedures are of potential benefit when the heart muscle is not dead but may be dysfunctional because of inadequate blood flow. If normal coronary blood flow is restored, viable dysfunctional myocardium may contract more normally, and heart function may improve. However, revascularization rarely restores cardiac function to normal or near-normal levels in patients with CHF, even though mild improvements are sometimes noted.

Finally, heart transplantation can be a suitable option for patients who have no other confounding diseases and are relatively young, but this is an option for only a small number of patients with heart failure, and only at great expense. In summary, CHF has a very poor prognosis and responds poorly to current therapies.

Further complicating the physiological conditions associated with CHF, are various natural adaptations that tend to occur in patients with dysfunctional hearts. Although these natural responses can initially improve heart function, they ultimately result in problems that can exacerbate CHF, confound treatment, and have adverse effects on survival. There are three such adaptive responses commonly observed in CHF: (i) volume retention induced by changes in sodium reabsorption, which expands plasma volume and initially improves cardiac output; (ii) cardiac enlargement (from dilation and hypertrophy) which can increase stroke volume while maintaining relatively normal wall tension; and (iii) increased norepinephrine release from adrenergic nerve terminals impinging on the heart which, by interacting with cardiac β-adrenergic receptors, tends to increase heart rate and force of contraction, thereby increasing cardiac output. However, each of these three natural adaptations tends ultimately to fail for various reasons. In particular, fluid retention tends to result in edema and retained fluid in the lungs that impairs breathing; heart enlargement can lead to deleterious left ventricular remodeling with subsequent severe dilation and increased wall tension, thus exacerbating CHF; and long-term exposure of the heart to norepinephrine tends to make the heart unresponsive to adrenergic stimulation and is linked with poor prognosis.

Controlled use of pharmacological agents, such as β-adrenergic agonists; and other modulatory drugs, thus remains one of the major forms of treatment despite its shortfalls, including its potentially adverse effect on survival. Researchers who have analyzed and in some cases cloned DNA sequences encoding individual components involved in the β-adrenergic receptor pathway have proposed using such components to identify new classes of drugs that might prove more useful in treating CHF. For example, Ishikawa et al. cloned DNA encoding two different isoforms of adenylylcyclase ($AC_V$ and $AC_{VI}$) that are known to be predominant in mammalian cardiac tissue, and proposed using the DNA and/or recombinant protein to identify new classes of drugs that might stimulate adrenergic pathways (See, e.g., American Cyanamid, WO 93/05061, Mar. 18, 1993, and EP 0 529 662, Mar. 3, 1993; and Ishikawa U.S. Pat. No. 5,334,521, issued Aug. 2, 1994). In other reports in which cloned components of the adrenergic stimulation pathway were investigated, the authors generated transgenic mice overexpressing certain components (including cardiac $β_2$-adrenergic receptors, $Gs_α$ and G-protein receptor kinase inhibitors) and obtained some data suggesting that β-adrenergic stimulation may be enhanced in transgenic mice (see, e.g., Gaudin C, et al., J Clin Invest 95: 1676–1683, 1995; Koch W J, et al., Science 268: 1350–1353, 1995; and Bond R A, et al., Nature 364: 272–276, 1995). None of these reports showed that cardiac function could be effectively restored in animals with heart failure, nor did they show that adrenergic responsiveness could be enhanced in large animal models that would be considered predictive of success in treating CHF in humans.

Indeed, reflecting on the observed difficulties associated with the clinical use of β-adrenergic agonists (such as dopamine and dobutamine), a recent review concluded that β-adrenergic stimulation appears to be harmful; and that, on the contrary, β-receptor "blockers" or antagonists may be more useful for improving morbidity and mortality rates (see, e.g., Baughman, K., Cardiology Clinics 13: 27–34, 1995). While some agents may improve symptoms, the prognosis for patients receiving such pharmacological agents remains dismal.

The invention described and claimed herein addresses and overcomes these and other problems associated with the prior art by providing techniques by which cardiac function can be effectively enhanced in vivo without the administration of β-adrenergic-agonist drugs.

SUMMARY OF THE INVENTION

Figure 1A:
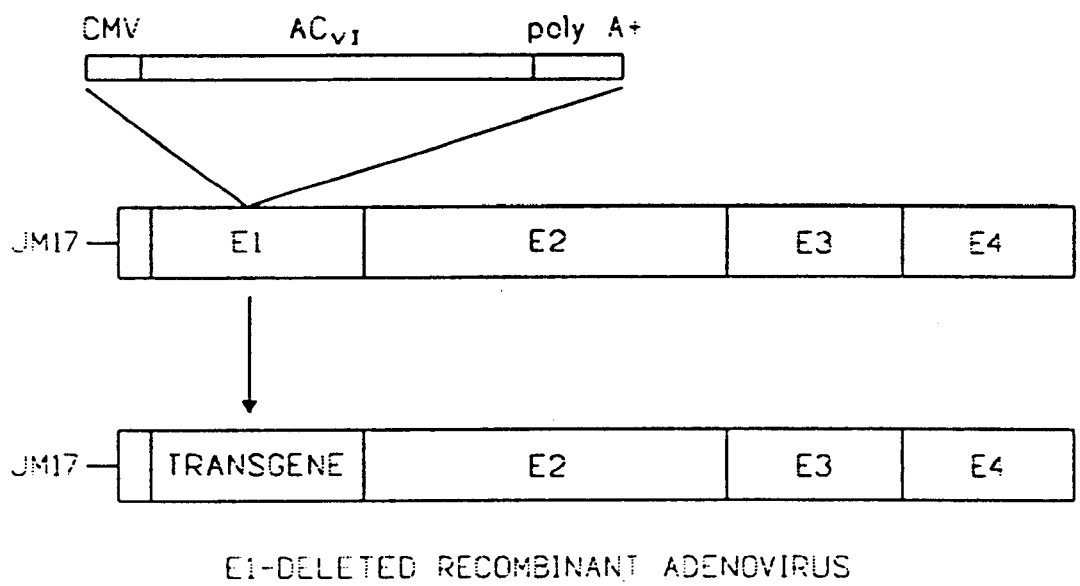
FIG. 1A shows a schematic of the construction of an exemplary replication-defective recombinant adenovirus vector useful for gene transfer into cells and into the heart, as described in Example 5–1 below.

The present invention relates to methods and compositions for enhancing cardiac function in mammalian hearts by inserting transgenes that increase β-adrenergic responsiveness within the myocardium. The present invention can thus be used in the treatment of heart disease, especially congestive heart failure.

Various aspects of the present invention include the following:

A method of enhancing cardiac function in a mammal, comprising delivering a vector to the heart of said mammal, the vector comprising a gene encoding a β-adrenergic signaling protein (β-ASP) operably linked to a promoter. Preferably, the vector is introduced into a blood vessel supplying blood to the myocardium of the heart, so as to deliver the vector to cardiac myocytes; more preferably the vector is introduced into the lumen of a coronary artery, a saphenous vein graft, or an internal mammary artery graft. Most preferably, the vector is introduced into the lumen of both the left and right coronary arteries. Preferably, the mammal is a human.

In preferred methods of enhancing cardiac function according to one of the preceding embodiments, the vector comprises at least one gene encoding a β-ASP selected from the group consisting of a β-adrenergic receptor (β-AR), a G-protein receptor kinase inhibitor (GRK inhibitor) and an adenylylcyclase (AC), each operably linked to a promoter. The method can also comprise introducing a vector encoding two different β-adrenergic signaling proteins (β-ASPs), each operably linked to a promoter, or introducing a second vector comprising a second β-ASP gene operably linked to a promoter.

In one preferred embodiment described herein, the vector comprises a gene encoding an adenylylcyclase (AC), preferably a cardiac AC such as AC isoform II, AC isoform V or AC isoform VI, more preferably AC isoform VI. In another preferred embodiment described herein, the vector comprises a gene encoding a β-AR, preferably a $β_1$-adrenergic receptor ($β_1$-AR) or a $β_2$-adrenergic receptor ($β_2$-AR), more preferably a $β_1$-AR. In another preferred embodiment described herein, the vector comprises a gene encoding a GRK inhibitor, which is preferably a gene encoding a GRK protein having a mutation that impairs kinase activity without eliminating receptor binding activity, more preferably the mutation is a truncation deleting the kinase domain.

In preferred methods of enhancing cardiac function according to one of the preceding embodiments, the vector comprises a gene encoding a β-ASP operably linked to a heterologous constitutive promoter or a heterologous inducible promoter. A preferred heterologous constitutive promoter is a CMV promoter which also includes an enhancer. In other preferred embodiments described herein, the promoter is a tissue-specific promoter, preferably a cardiac-specific promoter, more preferably, a ventricular myocyte-specific promoter. Preferred examples of ventricular myocyte-specific promoters include a ventricular myosin light chain 2 promoter and a ventricular myosin heavy chain promoter. The gene encoding a β-ASP can also be operably linked to a heterologous enhancer, such as the CMV enhancer. Preferably, the gene encoding a β-ASP is also operably linked to a polyadenylation signal.

In preferred methods of enhancing cardiac function according to one of the preceding embodiments, the vector is a viral vector or a lipid-based vector, preferably a viral vector. The vector can be a targeted vector, especially a targeted vector that preferentially binds to ventricular myocytes. Presently preferred viral vectors are derived from adenovirus (Ad) or adeno-associated virus (AAV). Both human and non-human viral vectors can be used but preferably the recombinant viral vector is replication-defective in humans. Where the vector is an adenovirus, it preferably comprises a polynucleotide having a promoter operably linked to a gene encoding a β-ASP (such as a β-AR, a GRK inhibitor, and/or an adenylylcyclase), and is replication-defective in humans. Presently preferred replication-defective adenoviral vector have deletions that remove the E1A and E1B genes, or have deletions that remove the E1A, E1B and E4 genes. Preferably about $10^7$ to $10^{13}$ adenovirus vector particles, more preferably about $10^9$ to $10^{12}$ vector particles, are introduced into a blood vessel, preferably a blood vessel supplying the myocardium as described above. For AAV vectors, the vector preferably comprises a polynucleotide having a promoter operably linked to a gene encoding a β-ASP (such as a β-AR, a GRK inhibitor, and/or an adenylylcyclase) and, preferably, the gene encoding a β-ASP is flanked by AAV inverted terminal repeats (ITRs). Preferably, the AAV vector is replication-defective in humans. Presently preferred replication-defective AAV vectors have deletions affecting one or more AAV replication or encapsidation sequences. Alternatively, the vector can be a lipid-based vector comprising a gene encoding β-ASP (such as a β-AR, a GRK inhibitor, and/or an adenylylcyclase) as described herein.

A recombinant replication-defective viral particle comprising a gene encoding a β-ASP (such as a β-AR, a GRK inhibitor, and/or an adenylylcyclase) operably linked to a promoter. Preferably, the promoter is a heterologous constitutive or inducible promoter. The vector can also comprise genes encoding more than one β-ASP. Preferred viral vectors are derived from adenovirus (Ad) or adeno-associated virus (AAV). Both human and non-human viral vectors can be used but preferably the recombinant viral vector is replication-defective in humans. Where the vector is an adenovirus, it preferably comprises a polynucleotide having a promoter operably linked to a gene encoding a β-ASP (such as a β-AR, a GRK inhibitor, and/or an adenylylcyclase), and is replication-defective in humans. Presently preferred replication-defective adenoviral vector have deletions that remove the E1A and E1B genes, or have deletions that remove the E1A, E1B and E4 genes. For AAV vectors, the vector preferably comprises a polynucleotide having a promoter operably linked to a gene encoding a β-ASP (such as a β-AR, a GRK inhibitor, and/or an adenylylcyclase) and, preferably, the gene encoding a β-ASP is flanked by AAV inverted terminal repeats (ITRs). Preferably, the AAV vector is replication-defective in humans. Presently preferred replication-defective AAV vectors have deletions affecting one or more AAV replication or encapsidation sequences. Other vectors of the present invention include lipid-based vectors (such as liposomes) comprising one or more genes encoding a β-ASP (such as a β-AR, a GRK inhibitor, and/or an adenylylcyclase), as described herein.

A mammalian cell transfected with a recombinant replication-defective viral particle or other vector according to one of the preceding embodiments.

A filtered injectable adenovirus particle preparation comprising: (i) a recombinant replication-defective adenovirus particle as described above, and (ii) a carrier. The carrier is preferably a pharmaceutically-acceptable carrier. Preferably the adenovirus vector has been filtered through a 0.1–0.5 micron filter.

A method of generating a recombinant replication-defective viral particle as described above, comprising the following steps in the order listed:
  (i) introducing first and second plasmids into a replication-permissive mammalian cell expressing one or more adenovirus genes conferring replication competence, wherein said first plasmid comprises a gene encoding a β-ASP (such as a β-AR, a GRK inhibitor, and/or an adenylylcyclase) operably linked to a promoter and further comprises a replication-defective adenovirus genome, and wherein said second plasmid comprises a replication-proficient adenovirus genome and further comprises an additional polynucleotide sequence making the second plasmid too large to be encapsidated in an adenovirus particle, whereby rescue recombination takes place between the first plasmid and the second plasmid to generate a recombinant adenoviral genome comprising the gene encoding a β-ASP but lacking one or more adenoviral replication genes, said recombinant adenoviral genome being sufficiently small to be encapsidated in an adenovirus particle;
  (ii) identifying successful recombinant viral vectors in cell culture; and
  (iii) propagating a resulting recombinant viral particle in replication-permissive mammalian cells expressing the missing adenoviral replication genes to generate a recombinant replication-defective viral particle.

The introducing step can be accomplished by co-transfection of the first and second plasmids into the permissive mammalian cell. The method can also comprise, prior to said step of introducing first and second plasmids, the step of cloning a gene encoding a β-ASP into a plasmid containing a promoter and partial adenovirus sequences of the left end of a replication-defective adenovirus genome such that the gene encoding the β-ASP is operably linked to said promoter. Preferably the method further comprises, after said propagation step, the step of purifying the propagated viral particles, and preferably also includes filtering the purified viral particles through a 0.1–0.5 micron filter. An exemplary first plasmid as described above is plasmid pAC1 or plasmid ACCMVPLPA comprising a gene encoding a β-ASP. The identification step described above preferably comprises the steps of: (i) monitoring transfected cells for evidence of cytopathic effect; (ii) isolating viral nucleic acid from the cell supernatant of cultures of the transfected cells showing a cytopathic effecttreating the cell supernatant from cell cultures showing a cytopathic effect with a proteinase (such as proteinase K), followed by phenol/chloroform extraction and ethanol precipitation; (iii) identifying successful recombinants with PCR using primers complementary to the promoter operably linked to the β-ASP gene and primers complementary to adenovirus sequences; and (iv) purifying the recombinant viral particles by plaque purification (preferably for at least two rounds). Viral nucleic acid can be isolated by treating the cell culture supernatant suspected of containing recombinant viral particles with a proteinase (such as proteinase K), followed by phenol/chloroform extraction of the proteinase-treated supernatant to remove proteins, and finally, ethanol precipitation of the lysate to obtain viral DNA.

The purification step as described above preferably comprises the steps of: (i) propagating the resulting recombinants in cells transformed with the replication competence conferring genes to titers in the $10^{10}$–$10^{12}$ viral particles range; and (ii) purifying the propagated recombinants (preferably by double CsCl gradient ultracentrifugation).

A recombinant pro-viral plasmid comprising a gene encoding a β-ASP operably linked to a promoter and further comprising a replication-defective viral genome. Preferably, the β-ASP is a β-AR, a GRK inhibitor or an adenylylcyclase, more preferably, adenylylcyclase isoform VI. Exemplary replication-defective viral genomes include an adenovirus genome and an AAV genome. Where the recombinant replication-defective viral genome is an adenovirus genome, the adenovirus may be either a human or a non-human mammalian adenovirus (preferably non-human mammalian), but in either case is preferably replication-defective in humans. Preferably, the recombinant replication-defective adenovirus genome has deletions removing the E1A and E1B genes, or deletions removing the E1A, E1B and E4 genes. Where the recombinant replication-defective viral genome is an AAV genome, the AAV genome preferably has deletions affecting one or more AAV replication or encapsidation sequences.

A cell comprising a recombinant pro-viral plasmid according to one of the preceding embodiments.

DETAILED DESCRIPTION OF PREFERRED EMBODIMENTS

Definitions

A "polynucleotide" refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. It also includes modified polynucleotides such as methylated and/or capped polynucleotides.

"Recombinant," as applied to a polynucleotide, means that the polynucleotide is the product of various combinations of cloning, restriction and/or ligation steps, and other procedures that result in a construct that is distinct from a polynucleotide found in nature.

A "gene" refers to a polynucleotide or portion of a polynucleotide comprising a sequence that encodes a protein. For most situations, it is desirable for the gene to also comprise a promoter operably linked to the coding sequence in order to effectively promote transcription. Enhancers, repressors and other regulatory sequences may also be included in order to modulate activity of the gene, as is well known in the art. (See, e.g., the references cited below).

The terms "polypeptide," "peptide," and "protein" are used interchangeably to refer to polymers of amino acids of any length. These terms also include proteins that are post-translationally modified through reactions that include glycosylation, acetylation and phosphorylation.

A "heterologous" component refers to a component that is introduced into or produced within a different entity from that in which it is naturally located. For example, a polynucleotide derived from one organism and introduced by genetic engineering techniques into a different organism is a heterologous polynucleotide which, if expressed, can encode a heterologous polypeptide. Similarly, a promoter or enhancer that is removed from its native coding sequence and operably linked to a different coding sequence is a heterologous promoter or enhancer.

A "promoter," as used herein, refers to a polynucleotide sequence that controls transcription of a gene or coding sequence to which it is operably linked. A large number of promoters, including constitutive, inducible and repressible promoters, from a variety of different sources, are well known in the art and are available as or within cloned polynucleotide sequences (from, e.g., depositories such as the ATCC as well as other commercial or individual sources).

An "enhancer," as used herein, refers to a polynucleotide sequence that enhances transcription of a gene or coding sequence to which it is operably linked. A large number of enhancers, from a variety of different sources are well known in the art and available as or within cloned polynucleotide sequences (from, e.g., depositories such as the ATCC as well as other commercial or individual sources). A number of polynucleotides comprising promoter sequences (such as the commonly-used CMV promoter) also comprise enhancer sequences.

"Operably linked" refers to a juxtaposition, wherein the components so described are in a relationship permitting them to function in their intended manner. A promoter is operably linked to a coding sequence if the promoter controls transcription of the coding sequence. Although an operably linked promoter is generally located upstream of the coding sequence, it is not necessarily contiguous with it. An enhancer is operably linked to a coding sequence if the enhancer increases transcription of the coding sequence. Operably linked enhancers can be located upstream, within or downstream of coding sequences. A polyadenylation sequence is operably linked to a coding sequence if it is located at the downstream end of the coding sequence such that transcription proceeds through the coding sequence into the polyadenylation sequence.

A "replicon" refers to a polynucleotide comprising an origin of replication which allows for replication of the polynucleotide in an appropriate host cell. Examples include replicons of a target cell into which a heterologous nucleic acid might be integrated (e.g., nuclear and mitochondrial chromosomes), as well as extrachromosomal replicons (such as replicating plasmids and episomes).

"Gene delivery," "gene transfer," and the like as used herein, are terms referring to the introduction of an exogenous polynucleotide (sometimes referred to as a "transgenes") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art and described herein.

"In vivo" gene delivery, gene transfer, gene therapy and the like as used herein, are terms referring to the introduction of a vector comprising an exogenous polynucleotide directly into the body of an organism, such as a human or non-human mammal, whereby the exogenous polynucleotide is introduced to a cell of such organism in vivo.

A "vector" (sometimes referred to as gene delivery or gene transfer "vehicle") refers to a macromolecule or complex of molecules comprising a polynucleotide to be delivered to a host cell, either in vitro or in vivo. The polynucleotide to be delivered may comprise a coding sequence of interest in gene therapy. Vectors include, for example, viral vectors (such as adenoviruses ("Ad"), adeno-associated viruses (AAV), and retroviruses), liposomes and other lipid-containing complexes, and other macromolecular complexes capable of mediating delivery of a polynucleotide to a host cell. Vectors can also comprise other components or functionalities that further modulate gene delivery and/or gene expression, or that otherwise provide beneficial properties to the targeted cells. As described and illustrated in more detail below, such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. A large variety of such vectors are known in the art and are generally available (see, e.g., the various references cited below).

A "recombinant viral vector" refers to a viral vector comprising one or more heterologous genes or sequences. Since many viral vectors exhibit size-constraints associated with packaging, the heterologous genes or sequences are typically introduced by replacing one or more portions of the viral genome. Such viruses may become replication-defective, requiring the deleted function(s) to be provided in trans during viral replication and encapsidation (by using, e.g., a helper virus or a packaging cell line carrying genes necessary for replication and/or encapsidation) (see, e.g., the references and illustrations below). Modified viral vectors in which a polynucleotide to be delivered is carried on the outside of the viral particle have also been described (see, e.g., Curiel, D T, et al. PNAS 88: 8850–8854, 1991).

Viral "packaging" as used herein refers to a series of intracellular events that results in the synthesis and assembly of a viral vector. Packaging typically involves the replication of the "pro-viral genome", or a recombinant pro-vector typically referred to as a "vector plasmid" (which is a recombinant polynucleotide than can be packaged in an manner analogous to a viral genome, typically as a result of being flanked by appropriate viral "packaging sequences"), followed by encapsidation or other coating of the nucleic acid. Thus, when a suitable vector plasmid is introduced into a packaging cell line under appropriate conditions, it can be replicated and assembled into a viral particle. Viral "rep" and "cap" genes, found in many viral genomes, are genes encoding replication and encapsidation proteins, respectively. A "replication-defective" or "replication-incompetent" viral vector refers to a viral vector in which one or more functions necessary for replication and/or packaging are missing or altered, rendering the viral vector incapable of initiating viral replication following uptake by a host cell. To produce stocks of such replication-defective viral vectors, the virus or pro-viral nucleic acid can be introduced into a "packaging cell line" that has been modified to contain genes encoding the missing functions which can be supplied in trans). For example, such packaging genes can be stably integrated into a replicon of the packaging cell line or they can be introduced by transfection with a "packaging plasmid" or helper virus carrying genes encoding the missing functions.

A "detectable marker gene" is a gene that allows cells carrying the gene to be specifically detected (e.g., distinguished from cells which do not carry the marker gene). A large variety of such marker genes are known in the art. Preferred examples thereof include detectable marker genes which encode proteins appearing on cellular surfaces, thereby facilitating simplified and rapid detection and/or cellular sorting. By way of illustration, the lacZ gene encoding beta-galactosidase can be used as a detectable marker, allowing cells transduced with a vector carrying the lacZ gene to be detected by staining, as described below.

A "selectable marker gene" is a gene that allows cells carrying the gene to be specifically selected for or against, in the presence of a corresponding selective agent. By way of illustration, an antibiotic resistance gene can be used as a positive selectable marker gene that allows a host cell to be positively selected for in the presence of the corresponding antibiotic. Selectable markers can be positive, negative or bifunctional. Positive selectable markers allow selection for cells carrying the marker, whereas negative selectable markers allow cells carrying the marker to be selectively eliminated. A variety of such marker genes have been described, including bifunctional (i.e. positive/negative) markers (see, e.g., WO 92/08796, published May 29, 1992, and WO 94/28143, published Dec. 8, 1994). Such marker genes can provide an added measure of control that can be advantageous in gene therapy contexts.

"β-adrenergic signaling," as used herein, refers to β-adrenergic receptor-mediated signaling which is mediated via β-adrenergic receptors ("β-ARs") present on cellular surfaces. Of particular relevance in the context of the present invention are receptors present on the surface of β-adrenergic-stimulated cells in the myocardium of mammalian heart tissue. As described below, β-adrenergic signaling within myocardial tissue is initially mediated by agonist binding to β-AR, followed by $G_s$-mediated signal transduction to adenylylcyclase (AC). Activated AC then catalyzes the synthesis of cyclic AMP (cAMP), and increased intracellular concentrations of cAMP mediate increased cytosolic calcium transients which enhance both the rate and force of cardiac contraction (referred to as positive chronotrophy and positive inotrophy, respectively). Various β-adrenergic signaling proteins, and other factors affecting β-adrenergic signaling, are described in the art and are further illustrated herein.

A "β-adrenergic signaling protein" (sometimes abbreviated "β-ASP" herein) or "β-adrenergic signaling element" refers to a protein that is capable of enhancing β-adrenergic receptor-mediated signaling when expressed in mammalian tissue, preferably (for purposes of the present invention) when expressed in mammalian myocardial tissue. β-adrenergic signaling proteins thus include "β-adrenergic signal transducer" proteins that mediate or transduce β-adrenergic signaling, preferably in mammalian myocardial cells, as well as proteins which can either stimulate such transducer proteins or which can inactivate or compete with inhibitors of such transducer proteins (thereby indirectly enhancing signal transduction). A variety of such proteins that are associated with β-adrenergic receptor-mediated signaling in mammalian cardiac tissue have been identified (see, e.g., the various references regarding β-adrenergic responsiveness cited above) and are illustrated herein. Preferred β-ASPs for use in the present invention are those that are known to play a role in β-adrenergic receptor-mediated signal transduction in mammalian heart tissue, such as the various proteins associated with the "βAR-Gs-AC" pathway, comprising a β-adrenergic receptor ("βAR"), a $G_s$ protein transducer and an adenylylcyclase ("AC") effect or, as well as proteins enhancing the activity of such βAR-Gs-AC proteins, as described in more detail herein and in the cited art. Recent data have demonstrated that $G_s$ protein is generally present at a much higher molar proportion than either βAR or AC. The latter two proteins (βAR and AC), as well as inhibitors of G-protein receptor kinases (which affect βAR activity) are preferred β-adrenergic receptor-mediated signaling components for use in the present invention. Examples of preferred β-ASPs for use in the present invention thus include: β-adrenergic receptors (such as $β_1$-adrenergic receptors or $β_2$-adrenergic receptors, more preferably $β_1$-adrenergic receptors), adenylylcyclases (preferably a cardiac AC such as $AC_V$ or $AC_{VI}$, more preferably $AC_{VI}$); as well as inhibitors of the function of G-protein receptor kinases (which are generally referred to herein as "GRK" inhibitors).

"β-adrenergic receptors" (abbreviated "β-AR" or "βAR") are the cell-surface receptors involved in β-adrenergic receptor-mediated signaling via the βAR-Gs-AC pathway. Within the myocardium of a mammalian heart, βARs are the principal receptors for norepinephrine (the sympathetic neurotransmitter) and for epinephrine (the adrenal hormone). Human myocardium contains both $β_1$-adrenergic receptors and $β_2$-adrenergic receptors, but $β_1$-ARs are predominant and are most closely associated with the altered β-adrenergic signaling that is observed with heart failure, as described below.

"$G_s$ protein" is a GTP-binding regulatory protein that effectively couples activation of a variety of cell-surface receptors (including β-adrenergic receptors) to the activation of adenylylcyclase, as described in the art and herein.

"Adenylylcyclase" (EC 4.6.1.1, also referred to as "adenylcyclase", "adenylate cyclase", and "cAMP synthetase") is an enzyme that catalyzes the conversion of adenosine triphosphate (ATP) to 3':5'-cyclic adenosine monophosphate (cAMP). Adenylylcyclase (abbreviated herein as "AC") is known to exist in a number of different isoforms that are found in varying levels in most all mammalian tissues. The most preferred adenylylcyclases of the present invention are "cardiac adenylylcyclases" which are isoforms found to be predominant in mammalian heart tissue, particularly in cardiac myocytes; as described in more detail below.

"G-protein receptor kinases" (abbreviated "GRK", but also referred to in the art as "β-adrenergic receptor kinases" or "βARK"), are kinase proteins that catalyze phosphorylation of G-protein-coupled receptor proteins including β-adrenergic receptors ("βARs"). Phosphorylation of βARs by GRK proteins leads to uncoupling of the receptors and a concomitant decrease in responsiveness to β-adrenergic signaling.

"GRK inhibitors," as used herein refer to proteins that inhibit the function of G-protein receptor kinases. Such inhibitors of GRK include modified GRK proteins in which receptor-binding activity has been uncoupled from kinase activity. Exemplary GRK inhibitors thus include modified GRKs that have been truncated (typically by deletions beginning at the amino-terminus) to remove kinase function while retaining the ability to bind to G-protein-coupled receptor proteins such as βARs. Such truncated GRK proteins can thus effectively compete with or prevent normal GRK from binding to βAR but do not cause subsequent inhibition of receptor activity (since they lack kinase activity). Examples of GRK inhibitors that can be used in the present invention are described below.

"Vasculature" or "vascular" are terms referring to the system of vessels carrying blood (as well as lymph fluids) throughout the mammalian body.

"Blood vessel" refers to any of the vessels of the mammalian vascular system, including arteries, arterioles, capillaries, venules, veins, sinuses, and vasa vasorum.

"Artery" refers to a blood vessel through which blood passes away from the heart. Coronary arteries supply the tissues of the heart itself, while other arteries supply the remaining organs of the body. The general structure of an artery consists of a lumen surrounded by a multi-layered arterial wall.

An "individual" as used herein refers to a large mammal, most preferably a human.

"Treatment" or "therapy" as used herein refers to administering, to an individual patient, agents that are capable of eliciting a prophylactic, curative or other beneficial effect in the individual.

"Gene therapy" as used herein refers to administering, to an individual patient, vectors comprising a therapeutic gene.

A "therapeutic polynucleotide" or "therapeutic gene" refers to a nucleotide sequence that is capable, when transferred to an individual, of eliciting a prophylactic, curative or other beneficial effect in the individual.

References

The practice of the present invention will employ, unless otherwise indicated, conventional techniques of molecular biology and the like, which are within the skill of the art. Such techniques are explained fully in the literature. See e.g., Molecular Cloning: A Laboratory Manual, (J. Sambrook et al., Cold Spring Harbor Laboratory, Cold Spring Harbor, N.Y., 1989); Current Protocols in Molecular Biology (F. Ausubel et al. eds., 1987 and updated); Essential Molecular Biology (T. Brown ed., IRL Press 1991); Gene Expression Technology (Goeddel ed., Academic Press 1991); Methods for Cloning and Analysis of Eukaryotic Genes (A. Bothwell et al. eds., Bartlett Publ. 1990); Gene Transfer and Expression (M. Kriegler, Stockton Press 1990); Recombinant DNA Methodology (R. Wu et al. eds., Academic Press 1989); PCR: A Practical Approach (M. McPherson et al., IRL Press at Oxford University Press 1991); Cell Culture for Biochemists (R. Adams ed., Elsevier Science Publishers 1990); Gene Transfer Vectors for Mammalian Cells (J. Miller & M. Calos eds., 1987); Mammalian Cell Biotechnology (M. Butler ed., 1991); Animal Cell Culture (J. Pollard et al. eds., Humana Press 1990); Culture of Animal Cells, 2nd Ed. (R. Freshney et al. eds., Alan R. Liss 1987); Flow Cytometry and Sorting (M. Melamed et al. eds., Wiley-Liss 1990); the series Methods in Enzymology (Academic Press, Inc.); Techniques in Immunocytochemistry, (G. Bullock & P. Petrusz eds., Academic Press 1982, 1983, 1985, 1989); Handbook of Experimental Immunology, (D. Weir & C. Blackwell, eds.); Cellular and Molecular Immunology (A. Abbas et al., W. B. Saunders Co. 1991, 1994); Current Protocols in Immunology (J. Coligan et al. eds. 1991); the series Annual Review of Immunology; the series Advances in Immunology; Oligonucleotide Synthesis (M. Gait ed., 1984); and Animal Cell Culture (R. Freshney ed., IRL Press 1987).

Additional references describing delivery and logistics of surgery which may be used in the methods of the present invention include the following: Topol, E J (ed.), The Textbook of Interventional Cardiology, 2nd Ed. (W. B. Saunders Co. 1994); Rutherford, R B, Vascular Surgery, 3rd Ed. (W. B. Saunders Co. 1989); Wyngaarden J B et al. (eds.), The Cecil Textbook of Medicine, 19th Ed. (W. B. Saunders, 1992); and Sabiston, D, The Textbook of Surgery, 14th Ed. (W. B. Saunders Co. 1991).

Additional references describing cell types found in the blood vessels, and the structure of the vasculature which may be useful in the methods of the present invention include the following: W. Bloom & D. Fawcett, A Textbook of Histology, 10th Ed., (W. B. Saunders Co. 1975).

Various publications have postulated on the uses of gene transfer for the treatment or prevention of disease, including heart disease. See, e.g., Methods in Molecular Biology, Vol. 7: Gene Transfer and Expression Protocols, Murray, E. (ed.), Humana Press, Clifton, N.J. (1991); Mazur et al., Molecular and Cellular Pharmacology, 21:104–111, 1994; French, Herz 18:222–229, 1993; Williams, American Journal of Medical Sciences 306:129–136, 1993; and Schneider and French, Circulation 88:1937–1942, 1993.

Sources and structural/functional features of vectors and of various β-adrenergic signaling proteins that could be used in the present invention are provided in the various reports as cited throughout this specification, and are described in more detail below.

Incorporation by Reference

References cited within this application, including patents, published patent applications and other publications, are hereby incorporated by reference.

Description of Various Preferred Embodiments

Various preferred aspects of the present invention are summarized below and further described and illustrated in the subsequent detailed descriptions and examples.

One preferred aspect of the present invention is to provide methods for treating heart disease (especially CHF), in which one or more β-adrenergic signaling elements is synthesized in vivo in a patient by targeting the myocardium with a vector construct containing a gene encoding a β-adrenergic signaling element. The preferred methods employ vector constructs and/or delivery methods that result in localized expression of the β-adrenergic signaling element that is relatively restricted to the myocardium of the patient. The presently preferred β-adrenergic signaling proteins include adenylylcyclases ("AC"s) (preferably a cardiac AC such as $AC_{II}$, $AC_V$ or $AC_{VI}$, more preferably $AC_{VI}$), β-adrenergic receptors (such as $β_1$-adrenergic receptors or $β_2$-adrenergic receptors, preferably $β_1$-adrenergic receptors), and inhibitors of the function of G-protein receptor kinases "GRK inhibitors"). Examples of such preferred β-ASPs are described and illustrated below.

Preferred vectors for use in the present invention include viral vectors, lipid-based vectors and other vectors that are capable of delivering DNA to non-dividing cells in vivo.

Presently preferred are viral vectors, particularly replication-defective viral vectors (including, for example replication-defective adenovirus vectors and adeno-associated virus (AAV) vectors. For ease of production and use in the present invention, replication-defective adenovirus vectors are presently most preferred.

The presently preferred means of in vivo delivery (especially for vector constructs that are not otherwise targeted for delivery and/or expression that is restricted to the myocardium), is by injection of the vector into a blood vessel directly supplying the myocardium, preferably by injection into a coronary artery. Such injection is preferably achieved by catheter introduced substantially (typically at least about 1 cm) within the ostium of one or both coronary arteries or one or more saphenous veins or internal mammary artery grafts or other conduits delivering blood to the myocardium.

By injecting the vector stock, preferably containing no wild-type virus, deeply into the lumen of one or both coronary arteries (or grafts and other vascular conduits), preferably into both the right and left coronary arteries (or grafts and other vascular conduits), and preferably in an amount of $10^7$–$10^{13}$ viral particles as determined by optical densitometry (more preferably $10^9$–$10^{11}$ viral particles), it is possible to locally transfect a desired number of cells, especially cardiac myocytes, with genes that encode proteins that increase β-adrenergic signal transduction in the affected myocardium, thereby maximizing therapeutic efficacy of gene transfer, and minimizing undesirable effects at extra-cardiac sites and the possibility of an inflammatory response to viral proteins. Vector constructs that are specifically targeted to the myocardium, such as vectors incorporating myocardial-specific binding or uptake components, and/or which incorporate β-adrenergic signaling transgenes that are under the control of myocardial-specific transcriptional regulatory sequences (e.g., ventricular myocyte-specific promoters) can be used in place of or, preferably, in addition to such directed injection techniques as a means of further restricting expression to the myocardium, especially the ventricular myocytes. For vectors that can elicit an immune response, it is preferable to inject the vector directly into a blood vessel supplying the myocardium as described above, although the additional techniques for restricting the potential for extracardiac expression can also be employed.

As described in detail below, we have shown that the use of such techniques with vectors carrying β-adrenergic signaling element transgenes can effectively enhance endogenous β-adrenergic responsiveness and function within the myocardium of a large mammal heart, without any observed effect on non-cardiac tissues and without generating any substantial immune reaction.

In another aspect, the present invention provides a filtered, injectable adenovirus vector preparation, comprising a recombinant adenovirus vector, preferably in a final viral titer of $10^7$–$10^{14}$ viral particles, said vector containing no wild-type virus and comprising a partial adenovirus sequence from which one or more required adenovirus genes conferring replication competence, for example,, the E1A/E1B genes have been deleted, and a transgenes coding for a $β_1$-adrenergic signaling element such as $AC_{VI}$, $AC_V$, other adenylylcyclases, $β_2$-adrenergic receptors, or inhibitors of the function of G-protein receptor kinases, driven by a promoter flanked by the partial adenovirus sequence; and a pharmaceutically acceptable carrier.

In a further preferred aspect, the present invention provides methods for the generation of recombinant viral stocks capable of effecting expression of a β-adrenergic signaling element in vivo in the myocardium, comprising the steps of cloning a transgenes coding for a β-adrenergic signaling element (such as $AC_{VI}$, $AC_V$, other adenylylcyclases, $β_1$-adrenergic receptors, $β_2$-adrenergic receptors, or inhibitors of the function of G-protein receptor kinases) into a plasmid containing a promoter and a polylinker flanked by partial adenovirus sequences of an adenovirus genome from which one or more adenovirus genes required for replication competence (generically referred to as viral replication or "rep" genes), such as the E1A/E1B genes of the human adenovirus 5 genome, have been deleted; co-transfecting said plasmid into mammalian cells transformed with the missing replication genes, along with a plasmid which contains a complete adenovirus genome and an additional insert making the plasmid too large to be encapsidated, whereby rescue recombination takes place between the transgenes-inserted plasmid and the plasmid having the entire adenovirus genome so as to create a recombinant genome containing the transgenes without the deleted viral replication genes, said recombinant genome being sufficiently small to be encapsidated; identifying successful recombinants in cell cultures; propagating the resulting recombinant in mammalian cells comprising or transformed with the viral replication genes; and purifying the propagated recombinants so as to contain the recombinant vector, without wild-type virus therein, and preferably passing the purified vector through a filter, preferably 0.1–0.5 micron filter, more preferably a 0.3 micron filter, to obtain purified filtered recombinant virus stock.

These and other preferred aspects of the present invention are described and illustrated below.

Transgenes Encoding β-Adrenergic Signaling Elements

The present invention employs genes encoding protein or peptide elements that increase β-adrenergic signaling and are therefore capable of enhancing responsiveness to endogenous β-adrenergic stimulation within dysfunctional regions of a mammalian heart. Such proteins are referred to herein as "β-adrenergic signaling proteins" (or "β-ASPs"). The term β-ASP refers to a protein that is capable of enhancing β-adrenergic signaling when expressed in mammalian tissue, preferably (for purposes of the present invention) when expressed in mammalian myocardial tissue.

β-adrenergic signaling proteins include β-adrenergic signal transducer proteins that mediate or transduce β-adrenergic signaling, preferably in mammalian myocardial cells, as well as proteins which can either stimulate such transducer proteins or which can inactivate or compete with inhibitors of such transducer proteins (thereby indirectly enhancing signal transduction). A variety of such proteins that are associated with β-adrenergic signaling in mammalian cardiac tissue have been identified (see, e.g., the various references regarding β-adrenergic responsiveness cited above) and are illustrated herein.

Preferred β-ASPs for use in the present invention are those that are known to play a role in β-adrenergic signal transduction in mammalian heart tissue, such as the various proteins associated with the "βAR-Gs-AC" pathway, comprising a β-adrenergic receptor ("βAR"), a $G_s$ protein transducer and an adenylylcyclase ("AC") effect or, as described in more detail herein and in the cited art. Recent data have demonstrated that $G_s$ protein is generally present at a much higher molar proportion than either βAR or AC. The latter two proteins (βAR and AC), as well as inhibitors of G-protein receptor kinases (which affect βAR activity) are more preferred β-adrenergic signaling components for use in the present invention.

β-adrenergic signaling within myocardial tissue is initially mediated by agonist binding to βAR, followed by $G_s$-mediated signal transduction to AC. Activated AC then catalyzes the synthesis of cyclic AMP, and increased intracellular concentrations of cAMP mediate increased cytosolic calcium transients which enhance both the rate and force of cardiac contraction (referred to as positive "chronotrophy" and positive "inotrophy," respectively).

Examples of particularly preferred β-ASPs for use in the present invention thus include: β-adrenergic receptors (such as $β_1$-adrenergic receptors or $β_2$-adrenergic receptors, preferably $β_1$-adrenergic receptors), adenylylcyclases (preferably a cardiac AC such as $AC_V$ or $AC_{VI}$, more preferably $AC_{VI}$); as well as inhibitors of the function of G-protein receptor kinases (which are generally referred to herein as "GRK" inhibitors).

β-adrenergic receptors (abbreviated "β-AR" or "βAR") are cell-surface receptors involved in β-adrenergic signaling via the βAR-Gs-AC pathway. Within the myocardium of a mammalian heart, βARs are the principal receptors for norepinephrine (the sympathetic neurotransmitter) and for epinephrine (the adrenal hormone). Human myocardium contains both $β_1$-adrenergic receptors and $β_2$-adrenergic receptors, but $β_1$-ARs are predominant and are most closely associated with the altered β-adrenergic signaling that is observed with heart failure.

$G_s$ protein is a GTP-binding regulatory protein that effectively couples activation of a variety of cell-surface receptors (including β-adrenergic receptors) to the activation of adenylylcyclase, as described in the art and herein.

Adenylylcyclase (also referred to as "adenylylcyclase," and abbreviated "AC") is an enzyme that catalyzes the conversion of adenosine triphosphate (ATP) to 3':5'-cyclic adenosine monophosphate (cAMP). Adenylylcyclase is known to exist in a number of different isoforms that are found in varying levels in most all mammalian tissues. The most preferred adenylylcyclases of the present invention are "cardiac adenylylcyclases" which are isoforms found to be predominant in mammalian heart tissue, particularly in cardiac myocytes; as described in more detail below.

G-protein receptor kinases (abbreviated "GRK", but also referred to in the art as "β-adrenergic receptor kinases" or "βARK"), are kinase proteins that catalyze phosphorylation of G-protein-coupled receptor proteins including β-adrenergic receptors ("βARs"). Phosphorylation of βARs by GRK proteins leads to inactivation of the receptors and a concomitant decrease in responsiveness to β-adrenergic signaling.

GRK inhibitors, as used herein, refer to peptide inhibitors of the function of G-protein receptor kinases. Peptide inhibitors of GRK include modified GRK proteins in which receptor-binding activity has been uncoupled from kinase activity. Exemplary GRK inhibitors thus include modified GRKs that have been truncated (typically by deletions beginning at the amino-terminus) to remove kinase function while retaining the ability to bind to G-protein-coupled receptor proteins such as βARs. Such truncated GRK proteins can thus effectively compete with or prevent normal GRK from binding to βAR but without causing subsequent inhibition of receptor activity.

Genes encoding such β-adrenergic signaling proteins, including preferred genes encoding βARs, AC isoforms and inhibitors of GRK proteins are known in the art and generally available (see, e.g., the references cited above regarding β-adrenergic signaling components). In addition, since these components tend to be relatively highly conserved, new homologs (or isoforms) of known genes can generally be readily obtained by screening a cDNA or genomic library of interest (e.g., a tissue-specific cDNA library), using techniques that are now quite well known in the art (see, e.g., the molecular biology references cited herein).

As an initial demonstration of the usefulness of the methods of the present invention, we tested the delivery and expression of a transgenes encoding an adenylylcyclase protein as an illustrative example of a β-adrenergic signaling protein.

The most preferred adenylylcyclases of the present invention are "cardiac adenylylcyclases" which are isoforms found to be predominant in mammalian heart tissue, particularly in cardiac myocytes. Presently preferred cardiac ACs include AC isoform V (abbreviated "$AC_V$") and AC isoform VI (abbreviated "$AC_{VI}$"), with $AC_{VI}$ being presently most preferred for reasons described herein. Although the various AC isoforms are distinct in terms of DNA and protein sequence, and are typically expressed in a tissue-specific manner, certain of the isoforms are closely homologous to each other and the mammalian isoforms generally have a common topographical feature comprising transmembrane spanning regions that are associated with large cytoplasmic loops. In addition, the amino acid composition of the cytoplasmic loops tends to be conserved among isoforms. Typically, cloned DNA encoding such adenylylcyclases will already be available as plasmids, although polynucleotides encoding the enzymes can also be obtained using polymerase chain reaction (PCR) methodology, as described in the art (see, e.g., PCR: A Practical Approach (M. McPherson et al., IRL Press at Oxford University Press 1991)). The detection, purification, and characterization of adenylylcyclases, including assays for identifying and characterizing new adenylylcyclases effective in a given cell type, have also been described in a number of publications (see, e.g., the references cited herein by Ishikawa et al. and Krupinski et al., regarding AC isoforms).

As described and illustrated in more detail below, we have successfully employed gene therapy techniques to deliver vectors encoding AC (as an illustrative β-ASP) into the myocardium of a large animal model that has been determined to be predictive of heart function in humans. We have also shown that gene delivery of the β-ASP resulted in enhanced cardiac function in the animals tested, indicating that the methods of the present invention are likely to provide effective alternatives to present treatments for congestive heart failure.

Vectors for Gene Delivery in vivo

In general, the gene of interest is transferred to the heart, including cardiac myocytes, in vivo and directs production of the encoded protein. Preferably such production is relatively constitutive. A variety of different gene transfer vectors, including viral as well as non-viral systems, can be employed to deliver transgenes for use in the present invention (see, e.g., the references cited above). As illustrated below, we have found that the helper-independent replication-defective human adenovirus 5 system can be used effectively transfect a large percentage of myocardial cells in vivo by a single intracoronary injection. We have also shown that such a delivery technique can be used to effectively target vectors to the myocardium of a large mammal heart. Additional means of targeting vectors to particular cells or tissue types are described below and in the art.

In various illustrations described below, we have used recombinant adenovirus vectors based on the human adenovirus 5 (as described by McGrory W J, et al., Virology 163: 614–617, 1988) which are missing essential early genes from the adenovirus genome (usually E1A/E1B), and are therefore unable to replicate unless grown in permissive cell lines that provide the missing gene products in trans. In place of the missing adenovirus genomic sequences, a transgenes of interest can be cloned and expressed in tissue/cells infected with the replication-defective adenovirus. Although adenovirus-based gene transfer does not generally result in stable integration of the transgenes into the host genome (less than 0.1% adenovirus-mediated transfections result in transgenes incorporation into host DNA), adenovirus vectors can be propagated in high titer and transfect non-replicating cells; and, although the transgenes is not passed to daughter cells, this is suitable for gene transfer to adult cardiac myocytes, which do not actively divide. Retrovirus vectors provide stable gene transfer, and high titers are now obtainable via retrovirus pseudotyping (Burns, et al., Proc Natl Acad Sci (USA) 90: 8033–8037, 1993), but current retrovirus vectors are generally unable to efficiently transduce nonreplicating cells.

An advantage associated with nondividing cells such as myocytes is that the viral vector is not readily "diluted out" by host cell division. To further enhance duration of transgenes expression in the heart, however, it is also possible to employ various second generation adenovirus vectors that have both E1 and E4 deletions, which can be used in conjunction with cyclophosphamide administration (See, e.g., Dai et al., Proc. Nat'l Acad Sci. (USA) 92: 1401–1405, 1995). To further increase the extent of initial gene transfer, multiple infusions, or infusion in an isolated coronary circuit can also be employed.

Human 293 cells, which are human embryonic kidney cells transformed with adenovirus E1A/E1B genes, typify useful permissive cell lines for the production of such replication-defective vectors. However, other cell lines which allow replication-defective adenovirus vectors to propagate therein can also be used, such as HeLa cells.

References describing a variety of other gene delivery vectors are known in the art, some of which are cited herein. Such other vectors include, for example, other viral vectors (such as adeno-associated viruses (AAV), liposomes and other lipid-containing complexes, and other macromolecular complexes capable of mediating delivery of a polynucleotide to a host cell. As described above and in the cited references, vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. Selectable markers can be positive, negative or bifunctional. Positive selectable markers allow selection for cells carrying the marker, whereas negative selectable markers allow cells carrying the marker to be selectively eliminated. A variety of such marker genes have been described, including bifunctional (i.e. positive/negative) markers (see, e.g., Lupton, S., WO 92/08796, published May 29, 1992; and Lupton, S., WO 94/28143, published Dec. 8, 1994). Such marker genes can provide an added measure of control that can be advantageous in gene therapy contexts. A large variety of such vectors are known in the art and are generally available (see, e.g., the various references cited above).

Additional references describing adenovirus vectors and other viral vectors which could be used in the methods of the present invention include the following: Horwitz, M. S., Adenoviridae and Their Replication, in Fields, B., et al. (eds.) Virology, Vol. 2, Raven Press New York, pp.1679–1721, 1990); Graham, F., et al., pp.109–128 in Methods in Molecular Biology, Vol. 7: Gene Transfer and Expression Protocols, Murray, E. (ed.), Humana Press, Clifton, N. J. (1991); Miller, N., et al., FASEB Journal 9: 190–199, 1995; Schreier, H, Pharmaceutica Acta Helvetiae 68: 145–159, 1994; Schneider and French, Circulation 88:1937–1942, 1993; Curiel D. T., et al., Human Gene Therapy 3: 147–154, 1992; Graham, F. L., et al., WO 95/00655 (Jan. 5, 1995); Falck-Pedersen, E. S., WO 95/16772 (Jun. 22, 1995); Denefle, P. et al., WO 95/23867 (Sep. 8, 1995); Haddada, H. et al., WO 94/26914 (Nov. 24, 1994); Perricaudet, M. et al., WO 95/02697 (Jan. 26, 1995); Zhang, W., et al., WO 95/25071 (Oct. 12, 1995). A variety of adenovirus plasmids are also available from commercial sources, including, e.g., Microbix Biosystems of Toronto, Ontario (see, e.g., Microbix Product Information Sheet: Plasmids for Adenovirus Vector Construction, 1996).

Additional references describing AAV vectors which could be used in the methods of the present invention include the following: Carter, B., Handbook of Parvoviruses, vol. I, pp.169–228, 1990; Berns, Virology, pp. 1743–1764 (Raven Press 1990); Carter, B., Curr. Opin. Biotechnol., 3: 533–539, 1992; Muzyczka, N., Current Topics in Microbiology and Immunology, 158: 92–129, 1992; Flotte, T. R., et al., Am. J. Respir. Cell Mol. Biol. 7:349–356, 1992; Chatterjee et al., Ann. NY Acad. Sci., 770: 79–90, 1995; Flotte, T. R., et al., WO 95/13365 (May 18, 1995); Trempe, J. P., et al., WO 95/13392 (May 18, 1995); Kotin, R., Human Gene Therapy, 5: 793–801, 1994; Flotte, T. R., et al., Gene Therapy 2:357–362, 1995; Allen, J. M., WO 96/17947 (Jun. 13, 1996); and Du et al., Gene Therapy 3: 254–261, 1996.

Additional references describing non-viral vectors which could be used in the methods of the present invention include the following: Ledley, F D, Human Gene Therapy 6: 1129–1144, 1995; Miller, N., et al., FASEB Journal 9: 190–199, 1995; Chonn, A., et al., Curr. Opin. in Biotech. 6: 698–708, 1995; Schofield, J P, et al., British Med. Bull. 51: 56–71, 1995; Brigham, K. L., et al., J. Liposome Res. 3: 31–49, 1993; Brigham, K. L., WO 91/06309 (May 16, 1991); Feigner, P. L., et al., WO 91/17424 (Nov. 14, 1991); Solodin et al., Biochemistry 34: 13537–13544, 1995; WO 93/19768 (Oct. 14, 1993); Debs et al., WO 93/25673; Feigner, P. L., et al., U.S. Pat. No. 5,264,618 (Nov. 23, 1993); Epand, R. M., et al., U.S. Pat. No. 5,283,185 (Feb. 1, 1994); Gebeyehu et al., U.S. Pat. No. 5,334,761 (Aug. 2, 1994); Feigner, P. L., et al., U.S. Pat. No. 5,459,127 (Oct. 17, 1995); Overell, R. W., et al., WO 95/28494 (Oct. 26, 1995); Jessee, WO 95/02698 (Jan. 26, 1995); Haces and Ciccarone, WO 95/17373 (Jun. 29, 1995); Lin et al., WO 96/01840 (Jan. 25, 1996).

Construction of Recombinant Viral Vectors

For purposes of illustrating vector-mediated gene delivery of β-adrenergic signaling proteins to the myocardium, we chose a basic (i.e. "first generation") adenovirus vector that can be constructed by the rescue recombination technique as described in McGrory W J, et al., Virology 163:614–617, 1988. Briefly, the transgene of interest is cloned into a shuttle vector that contains a promoter, polylinker and partial flanking adenovirus sequences from which E1A/E1B genes have been deleted.

Illustrative shuttle vectors include, e.g., plasmid "pAC1" (Virology 163:614–617, 1988) (or an analog) which encodes portions of the left end of the human adenovirus 5 genome but lacks the early protein region comprising E1A and E1B sequences that are essential for viral replication; and plasmid "ACCMVPLPA" (J Biol Chem 267:25129–25134, 1992) which contains a polylinker, CMV promoter and SV40 polyadenylation signal flanked by partial adenovirus sequences from which the E1A/E1B genes have been deleted. The use of plasmids such as pAC1 or ACCMVPLA can thus facilitate the cloning process.

The shuttle vector can then be co-transfected, along with a plasmid comprising the entire human adenovirus 5 genome (but with a length too large to be encapsidated), into suitable host cells such as human 293 cells. Co-transfection can be conducted by calcium phosphate precipitation or lipofection (see, e.g., Biotechniques 15:868–872, 1993).

As an illustrative plasmid for co-transfection, plasmid "JM17" encodes the entire human adenovirus 5 genome plus portions of the vector pBR322 including the gene for ampicillin resistance (4.3 kb) (Giordano, et al. Nature Medicine 2: 534–539, 1996). Although JM17 encodes all of the adenovirus proteins necessary to make mature viral particles, it is too large to be encapsidated (40 kb versus 36 kb for wild type).

In a small subset of co-transfected cells, "rescue recombination" occurs between the transgene-containing shuttle vector (such as plasmid pAC1) and the plasmid having the entire adenovirus 5 genome (such as plasmid pJM17) which generates a recombinant genome that contains the transgene of interest in place of the deleted E1A/E1B sequences, and that secondarily loses the additional sequence (such as pBR322 sequences) during recombination, thereby being small enough to be encapsidated (see, e.g., Giordano, et al. Nature Medicine 2: 534–539, 1996). An illustration of such a vector is presented in FIG. 1. The CMV driven β-galactosidase gene in adenovirus HCMVSP1lacZ (Nature Medicine 2: 534–539, 1996) can be used to evaluate the efficiency of gene transfer using X-gal treatment.

Illustrative examples demonstrating the preparation and use of such vectors are provided below. Advantages of using adenovirus vectors include the ability to effect high efficiency gene transfer (as many as 50% of target organ cells transfected in vivo), the ease of obtaining high titer viral stocks and the ability of these vectors to effect gene transfer into cells such as cardiac myocytes which do not divide.

A variety of other vectors suitable for in vivo gene therapy can also be readily employed to deliver β-ASP transgenes in accordance with the present invention. Such other vectors include, by way of illustration, other viral vectors such as adeno-associated virus (AAV) vectors; non-viral protein-based delivery platforms); as well as lipid-based vectors (including, e.g., cationic liposomes and analogous gene delivery complexes. The preparation and use of these and other vectors are described in the art (see, e.g., the references regarding gene delivery vectors cited above).

Targeted β-ASP Vector Constructs

The present invention contemplates the use of cell targeting not only by delivery of the transgene into the coronary artery, for example, but also by use of targeted vector constructs having features that tend to target gene delivery and/or gene expression to particular host cells or host cell types (such as the myocardium). Such targeted vector constructs would thus include targeted delivery vectors and/or targeted vectors, as described in more detail below and in the published art. Restricting delivery and/or expression can be beneficial as a means of further focusing the potential effects of gene therapy. The potential usefulness of further restricting delivery/expression depends in large part on the type of vector being used and the method and place of introduction of such vector. As described herein, delivery of viral vectors via intracoronary injection to the myocardium has been observed to provide, in itself, highly targeted gene delivery (see the Examples below). In addition, using vectors that do not result in transgene integration into a replicon of the host cell (such as adenovirus and numerous other vectors), cardiac myocytes are expected to exhibit relatively long transgene expression since the cells do not undergo rapid turnover. In contrast, expression in more rapidly dividing cells would tend to be decreased by cell division and turnover. However, other means of limiting delivery and/or expression can also be employed, in addition to or in place of the illustrated delivery method, as described herein.

Targeted delivery vectors include, for example, vectors (such as viruses, non-viral protein-based vectors and lipid-based vectors) having surface components (such as a member of a ligand-receptor pair, the other half of which is found on a host cell to be targeted) or other features that mediate preferential binding and/or gene delivery to particular host cells or host cell types. As is known in the art, a number of vectors of both viral and non-viral origin have inherent properties facilitating such preferential binding and/or have been modified to effect preferential targeting (see, e.g., Miller, N., et al., FASEB Journal 9: 190–199, 1995; Chonn, A., et al., Curr. Opin. in Biotech. 6: 698–708, 1995; Schofield, J P, et al., British Med. Bull. 51: 56–71, 1995; Schreier, H, Pharmaceutica Acta Helvetiae 68: 145–159, 1994; Ledley, F D, Human Gene Therapy 6: 1129–1144, 1995; Conary, J. T., et al., WO 95/34647 (Dec. 21, 1995); Overell, R. W., et al., WO 95/28494 (Oct. 26, 1995); and Truong, V. L. et al., WO 96/00295 (Jan. 4, 1996)).

Targeted vectors include vectors (such as viruses, non-viral protein-based vectors and lipid-based vectors) in which delivery results in transgene expression that is relatively limited to particular host cells or host cell types. By way of illustration, β-ASP transgenes to be delivered according to the present invention can be operably linked to heterologous tissue-specific promoters thereby restricting expression to cells in that particular tissue.

For example, tissue-specific transcriptional control sequences derived from a gene encoding left ventricular myosin light chain-2 ($MLC_{2V}$) or myosin heavy chain (MHC) can be fused to a β-ASP transgene (such as the $AV_{VI}$ gene) within a vector such as the adenovirus constructs described above. Expression of the transgene can therefore be relatively restricted to ventricular cardiac myocytes. The efficacy of gene expression and degree of specificity provided by $MLC_{2V}$ and MHC promoters with lacZ have been determined (using a recombinant adenovirus system such as that exemplified herein); and cardiac-specific expression has been reported (see, e.g., Lee, et al., J Biol Chem 267:15875–15885,1992).

Since the $MLC_{2V}$ promoter comprises only about 250 bp, it will fit easily within even size-restricted delivery vectors such as the adenovirus-5 packaging system exemplified herein. The myosin heavy chain promoter, known to be a vigorous promoter of transcription, provides another alternative cardiac-specific promoter and comprises less than 300 bp. Other promoters, such as the troponin-C promoter, while highly efficacious and sufficiently small, do not provide such tissue specificity.

Propagation and Purification of Viral Vectors

Recombinant viral vectors, such as adenoviral vectors, can be plaque purified according to standard methods. By way of illustration, recombinant adenoviral viral vectors can be propagated in human 293 cells (which provide E1A and E1B functions in trans) to titers in the preferred range of about $10^{10}$–$10^{12}$ viral particles/ml.

Propagation and purification techniques have been described for a variety of viral vectors that can be used in conjunction with the present invention. Adenoviral vectors are exemplified herein but other viral vectors such as AAV can also be employed. For adenovirus, cells can be infected at about 80% confluence and harvested 48 hours later. After 3 freeze-thaw cycles the cellular debris can be collected by centrifugation and the virus purified by CsCl gradient ultracentrifugation (double CsCl gradient ultracentrifugation is preferred).

Prior to in vivo injection, the viral stocks can be desalted by gel filtration through Sepharose columns such as G25 Sephadex. The product can then be filtered through a 30 micron filter, thereby reducing the potential for deleterious effects associated with intracoronary injection of unfiltered virus. The resulting viral stock preferably has a final viral titer that is at least about $10^{10}$–$10^{12}$ viral particles/ml.

Preferably, the recombinant adenovirus is highly purified, and is substantially free of wild-type (potentially replicative) virus. For these reasons, propagation and purification can be conducted to exclude contaminants and wild-type virus by, for example, identifying successful recombinants with PCR using appropriate primers, conducting two rounds of plaque purification, and double CsCl gradient ultracentrifugation. Additionally, we have found that the problems associated with cardiac arrhythmias that can be induced by adenovirus vector injections into patients can be essentially avoided by filtration of the recombinant adenovirus through an appropriately-sized filter prior to intracoronary injection. This strategy also appears to substantially improve gene transfer and expression.

Delivery of Vectors Carrying One or More β-ASP Transgenes

The means and compositions which are used to deliver the vectors carrying β-ASP transgenes depend on the particular vector employed as is well known in the art. Typically, however, a vector can be in the form of an injectable preparation containing pharmaceutically acceptable carrier/diluent such as saline, for example.

For viral vectors (such as adenovirus), the final titer of the virus in the injectable preparation is preferably in the range of about $10^{7}$–$10^{13}$ viral particles which allows for effective gene transfer. Other pharmaceutical carriers, formulations and dosages are described below.

Vectors comprising β-ASP transgenes can be delivered to the myocardium by direct intracoronary (or graft vessel) injection using standard percutaneous catheter based methods under fluoroscopic guidance, in an amount sufficient for the transgene to be expressed and to provide a therapeutic benefit. Such an injection is preferably made deeply into the lumen (about 1 cm within the arterial lumen) of the coronary arteries (or graft vessel), and preferably is made in both coronary arteries (to provide general distribution to all areas of the heart).

By injecting the material directly into the lumen of the coronary artery by coronary catheters, it is possible to target the gene rather effectively, and to minimize loss of the recombinant vectors to the proximal aorta during injection. We have found that gene expression when delivered in this manner does not occur in hepatocytes and that viral RNA cannot be found in the urine at any time after intracoronary injection. In addition, using PCR, we find no evidence of extracardiac gene expression in the eye, liver, or skeletal muscle two weeks after intracoronary delivery. Any variety of coronary catheter can be used in the present invention. In addition, other techniques known to those having ordinary skill in the art can be used for transfer of genes to the heart.

Animal Model of Congestive Heart Failure

Important prerequisites for developing any cardiac gene therapy technique to be applicable to humans are: (a) constitution of a large animal model that is applicable to clinical congestive heart failure and which can provide useful data regarding mechanisms for altered P-adrenergic signaling in the setting of heart failure, and (b) accurate evaluation of the effects of gene transfer. None of the prior art has effectively described and/or demonstrated a means for treating congestive heart failure using in vivo gene therapy.

For this invention, we have employed a porcine model of heart failure that mimics human clinical congestive heart failure in a number of important ways, including the clinical abnormalities associated with β-adrenergic signaling. In our porcine model, sustained rapid ventricular pacing in these large mammals (225 beats/min) results in left ventricular chamber enlargement, depressed systolic function, and hemodynamic abnormalities, all of which mimic clinical dilated heart failure in humans (see, e.g., Roth D A, et al., J Clin Invest 91: 939–949, 1993). Furthermore, the detailed analysis of altered β-adrenergic signaling in the porcine model heart, particularly plasma and myocardial catecholamine levels, β-adrenergic receptor down-regulation and uncoupling, and alterations in adenylylcyclase function, likewise mimic conditions associated with heart failure in humans (Roth D A, et al., J Clin Invest 91: 939–949, 1993).

The fundamental findings from studies conducted on myocardium from these animal models with heart failure vis-à-vis the current invention include the following. First, there is a 75% reduction in left ventricular $\beta_1$-adrenergic receptor number, with a similar decrease in $\beta_1$-adrenergic receptor mRNA; whereas $\beta_2$-adrenergic receptor number (and mRNA) do not change. This mirrors what is seen in human heart failure (see, e.g., Bristow M R, et al., J Clin Invest 92: 2737–2745, 1993). Second, left ventricular β-adrenergic receptors are uncoupled from Gs, and there is increased function and expression of G-protein receptor kinase. These findings are also present in failed human hearts (see, e.g., Ungerer M, et al., Circulation, 87: 454–461, 1993; Ungerer M, et al., Circ Res, 74: 206–213, 1994). Third, there is a reduction in the function of left ventricular AC, that is associated with mRNA for $AC_{VI}$ (Roth D A, et al., J Clin Invest, 91: 939–949, 1993; see also Ishikawa Y, et al., J Clin Invest, 93: 2224–2229, 1994).

Recent studies also show reduced forskolin-stimulated cAMP production in homogenates of failing left ventricle, suggesting impaired AC function (Bristow, M. R.et al., Mol. Pharm. 35, 295–303, 1989; Ishikawa, Y., et al., J. Clin. Invest. 93, 2224–2229, 1994; Kiuchi K., et al. J. Clin. Invest. 91, 907–914, 1993; Marzo, K. P., et al., Circ. Res. 69, 1546–1556, 1991; Roth, D. A., et al., J. Clin. Invest. 91, 939–949, 1993). A problem with the assessment of the catalytic subunit of AC is that there are currently only imperfect means to assess either its concentration or its function. The diterpene forskolin is an activator of AC and, accordingly, forskolin-stimulated cAMP production has been the most commonly employed method for assaying its biological activity. However, since full response to forskolin involves interaction of $Gs_I$ and AC, and since activation of Gi$_f$ inhibits forskolin response (Darfler, F. J., et al., J. Biol. Chem. 257, 11901–11907, 1982), forskolin stimulation falls short of providing a precise measure of AC function. It is widely recognized that AC tends to be quite labile and is generally unstable out of its normal cellular environment. Antibodies to AC are not widely available, and the protein is expressed in low abundance, exacerbating the problems of quantitation and functional assessment of this pivotal transducing element. Because of these problems, little is known about the precise alterations in quantity and function of AC in pathophysiological settings. Regulation of cellular function by AC is further complicated by the recent evidence that multiple isoforms of AC exist, at least two of which have been demonstrated to be expressed in the heart (Ishikawa, Y., et al., J. Clin. Invest. 93, 2224–2229, 1994; lyengar R. FASEB J. 7, 768–775, 1993; Katsusshika, S., et al., Proc. Natl. Acad. Sci. (U.S.A.) 89, 8774–8778, 1992; Krupinski, J., et al., J. Biol. Chem. 267,24858–24862, 1992; Tang, W. J. and A. G. Gilman. Cell 70, 869–872, 1992; Taussig, R., et al., J. Biol. Chem. 269, 6093–6100, 1994). Studies from our laboratories have employed two approaches to provide quantitative information regarding AC expression. First, forskolin binding is used to quantitate AC function (Alousi A, et al. FASEB Journal 5:2300–2303, 1991). Second, RNase protection assays are used to provide quantitative assessment of mRNA levels for AC isoforms (Ping P, et al., Circulation 90: I-I-580, 1994; Ping P and Hammond H K, Am J Physiol 267: H2079-H2085, 1994).

Using degenerate PCR primers for AC isoforms, we have isolated twenty-eight positive clones. Subsequent sequence analyses established, based upon previously reported sequences of AC isoforms, that at least three AC isoforms are expressed in porcine left ventricle. Previous reports regarding AC isoform expression in mammalian heart using whole rat heart homogenates and PCR identified eight AC isoforms (Katsusshika, S., et al., Proc. Natl. Acad. Sci. (U.S.A.) 89, 8774–8778, 1992); although the cell types expressing the various AC isoforms were not identified. Subsequent studies using Northern blotting (with poly-(A)-selection) have been able to identify only two isoforms, $AC_V$ and $AC_{VI}$ in dog heart (Ishikawa, Y., et al., J. Clin. Invest. 93, 2224–2229, 1994). Ishikawa, et al. (Ishikawa, Y., et al., J. Clin. Invest. 93, 2224–2229, 1994) confirmed that $AC_V$ and $AC_{VI}$ isoforms could be identified in RNA extracted from isolated cardiac myocytes.

We have found, with respect to the presently-employed porcine model, that AC isoforms II, V, and VI are present not only in RNA extracted from whole heart, but also in RNA extracted from a pure population of adult porcine left ventricular cardiac myocytes.

A previous study showed that severe heart failure was associated with downregulation of AC isoforms V and VI mRNA (Ishikawa, Y., et al., J. Clin. Invest. 93, 2224–2229, 1994). We used an animal model that mimics clinical CHF to see if AC isoform mRNA downregulation in heart failure is uniform among isoforms. Although our findings are in agreement with some aspects of previous reports, including an early uncoupling of myocardial βAR (Ishikawa, Y., et al., J. Clin. Invest. 93, 2224–2229, 1994; Kiuchi K., et al. J. Clin. Invest. 91, 907–914, 1993), there are also differences. First, we identified a third AC isoform of cardiac myocyte origin ($AC_{II}$), and established, through quantitative measurements, the level of expression of these three isoforms in left ventricle. Second, in contrast to lshikawa, et al. (Ishikawa, Y., et al., J. Clin. Invest. 93, 2224–2229, 1994), we found that AC isoform downregulation is isoform-specific. In particular, reduced ACv, expression appears to be associated with impaired β-adrenergic responsiveness in CHF.

In summary, in the normal heart, the amount of AC appears to set a limit on β-adrenergic responsiveness. In heart failure, where AC downregulation further impairs transmembrane signaling, this would be expected to be an even more important limitation affecting transmembrane β-adrenergic signaling.

Our studies with pigs, described and illustrated in more detail below, demonstrate that over-expression of a β-ASP (such as AC), by in vivo delivery to the myocardium, can enhance cardiac function in a large animal model predictive of humans. There are no previous publications describing and/or demonstrating such techniques for use in the treatment of heart failure. Our studies also provided additional confirmation that the CHF phenotype in the porcine pacing model is very similar to that observed in clinical CHF in humans.

Our demonstrated ability (using the methods of the present invention) to significantly increase adrenergic responsiveness in the porcine pacing model of CHF thus provides a critical advance, not only for understanding the molecular mechanisms of cardiac adrenergic signaling but also for actually treating the clinical condition.

As described in the examples below, we used normal pigs to initially examine the efficacy of our gene delivery techniques and to provide data to show that intracoronary gene delivery of a recombinant adenovirus expressing $AC_{VI}$ could positively impact cardiac function. In these initial studies, a recombinant adenovirus expressing lacZ (as a reporter gene used to document successful gene transfer and expression) was injected into the coronary arteries of 5 pigs (using approximately $0.5 \times 10^{11}$ viral particles). Two weeks later, the animals were killed and tissue samples were examined.

PCR was used to detect adenovirus DNA in myocardium from animals that had received gene transfer. Effective gene transfer was documented in the hearts of the pigs, and was not found in other tissues. As further confirmation of the success of these techniques, myocardial samples from lacZ-infected animals were found to exhibit substantial β-galactosidase activity on histological inspection.

To illustrate cardiac gene therapy using a β-ASP transgene, pigs were exposed to in vivo gene delivery of DNA encoding an $AC_{VI}$ isoform. In studies conducted on three animals, physiological measures of β-adrenergic responsiveness were obtained before and 5–10 days after intracoronary injection of a recombinant adenovirus expressing the βASP transgene (encoding $AC_{VI}$).

Our results revealed that heart rate responsiveness to β-adrenergic stimulation was significantly increased after gene transfer according to the present invention.

In addition, one of the pigs was further examined (both before and after gene transfer), to monitor potential changes in left ventricular dP/dt, which is a measure of the rate of rise of pressure development, and a further indicator of cardiac function. The results, described below, indicated that cardiac gene therapy according to the present invention also resulted in a substantial increase in left ventricular dP/dt. These data thus provided further confirmation that the techniques of the present invention can be used to enhance cardiac function in a large animal model that mimics CHF in humans.

Our data demonstrated that a βASP, AC, can be effectively delivered by in vivo gene therapy to a large animal heart and that β-adrenergic responsiveness and cardiac function can be increased using such a method. Other preferred β-ASP can be delivered in an analogous manner. By way of illustration, in the following description and in the examples, we describe additional types of β-ASPs, including a β-adrenergic receptor ($β_1$-AR) and a GRK inhibitor. $β_1$-AR is functionally upstream of AC in the βAR-$G_S$-AC pathway, and like AC has been found to be down-regulated in association with heart failure.

With further regard to the predictiveness of the pacing-induced model of heart failure to clinical heart failure in humans, it is important to note that although the two end conditions are not brought about in the same manner (i.e. in terms of etiology and rate of development), the resulting states of heart failure necessitating treatment are quite closely related. Thus, not only are both systems characterized by dilated, poorly contracting hearts, and multi-chamber enlargement, but, most importantly, the two systems exhibit strikingly similar abnormalities associated with β-adrenergic signaling (see, e.g., Bristow M R, et al., N Engl J Med, 307: 205–211, 1982; Bristow M R, et al., Mol Pharm, 35: 295–303, 1989; Bristow M R, et al., J Clin Invest, 92: 2737–2745, 1993; Ishikawa Y, et al., J Clin Invest, 93: 2224–2229, 1994; Kiuchi K, et al., J Clin Invest, 91: 907–914, 1993; Marzo K P, et al., Circ Res, 69: 1546–1556, 1991; Ping P, et al., Am J Physiol, 267: H2079-H2085, 1994; Ping P, et al., J Clin Invest, 95: 1271–1280, 1995; Roth D A, et al., J Clin Invest, 91: 939–949, 1993; Ungerer M, et al., Circulation, 87: 454–461, 1993; Ungerer M, et al., Circ Res, 74: 206–213, 1994).

The data described below also document, for the first time, that myocardial $GRK_5$ protein and mRNA contents are susceptible to upregulation in mild and severe heart failure. Without wishing to be bound by theory, our data support the idea that increased expression of $GRK_5$ may be responsible for the increased GRK activity observed in these clinical conditions. In any case, the current data strongly support the hypothesis that increased left ventricular GRK expression contributes to reduced adrenergic signaling at an early stage during the development of heart failure. The role of GRK in heart failure, and the use of GRK inhibitors as a β-ASP for gene delivery according to the present invention, are described in more detail below.

Without wishing to be bound by theory, our data support the idea that increased GRK expression is an early change in heart failure that predates alterations in AC isoform expression; and that impaired hormonal stimulation of AC, associated with βAR uncoupling, may result from increased βAR phosphorylation by GRK, possibly resulting from increased $GRK_5$ expression.

The enhancement of β-adrenergic responsiveness according to the present invention is expected to be beneficial for enhancing cardiac function in the numerous disease situations in which heart failure is associated with reductions in β-adrenergic signaling. In that regard, it is important to distinguish etiology from putative intervention points, particularly in situations such as this in which a molecular pathway leads from upstream signaling events to downstream effector events, and in which signaling components tend to be decreased (in number or activity) without actually being eliminated (thereby making the dysfunction and potential treatment more quantitative in nature). Thus, interventionary treatment such as that described herein can be directed at the principal molecular site of impact or potentially at a downstream site that tends to obviate or "by-pass" the principal limitation. By way of illustration, although an effective reduction in the level of a β-adrenergic receptor (β-AR) may be, and preferably is, treated directly by increasing the level of that same protein; it may also be compensated for indirectly, for example by increasing the activity of the residual β-AR proteins or relieving inhibition of such proteins (e.g. using GRK inhibitors), by increasing the activity of an analogous β-AR, and/or by increasing the availability of downstream signal transducers (e.g. AC) to make it more likely that initial signaling events result in downstream stimulation. Indeed, although our analyses described above support the idea that β-AR number and/or activity are significantly affected in severe heart failure, our results involving gene therapy in vivo according to the present invention (as described below) demonstrate that even intervention to increase a downstream component such as AC can substantially enhance cardiac function. Therapies directed at upstream deficiencies (employing, e.g., the delivery of β-AR and/or GRK inhibitors) would also be expected to provide substantial benefit in terms of β-adrenergic signaling and cardiac function. As described below, it will be possible to supply one or more such β-ASP transgenes according to the present invention as means of enhancing β-adrenergic responsiveness and cardiac function in the context of congestive heart failure.

Therapeutic Applications

Our data demonstrate that gene transfer of a β-adrenergic signaling element into the myocardium can be used to enhance responsiveness of the heart to endogenous β-adrenergic stimulation. Our technique, which we show to be successfully applicable in a large mammal model used to mimic clinical congestive heart failure in humans, would be expected to be beneficial for the treatment of CHF in humans, thereby providing a much-need alternative to present treatments such as the administration of exogenous β-adrenergic stimulants that tend to limit long-term survival.

As described herein, a number of different vectors can be employed to deliver the β-ASP transgene in vivo according to the present invention. By way of illustration, the replication-defective recombinant adenovirus vectors exemplified resulted in highly efficient gene transfer in vivo without cytopathic effect or inflammation in the areas of gene expression.

Compositions or products of the invention may conveniently be provided in the form of formulations suitable for administration into the blood stream (e.g. in an intracoronary artery). A suitable administration format may best be determined by a medical practitioner for each patient individually, according to standard procedures. Suitable pharmaceutically acceptable carriers and their formulation are described in standard formulations treatises, e.g., Remington's Pharmaceuticals Sciences by E. W. Martin. See also Wang, Y. J. and Hanson, M. A. "Parental Formulations of Proteins and Peptides: Stability and Stabilizers," Journals of Parental Sciences and Technology, Technical Report No. 10, Supp. 42:2S (1988). Vectors of the present invention should preferably be formulated in solution at neutral pH, for example, about pH 6.5 to about pH 8.5, more preferably from about pH 7 to 8, with an excipient to bring the solution to about isotonicity, for example, 4.5% mannitol or 0.9% sodium chloride, pH buffered with art-known buffer solutions, such as sodium phosphate, that are generally regarded as safe, together with an accepted preservative such as metacresol 0.1% to 0.75%, more preferably from 0.15% to 0.4% metacresol. Obtaining a desired isotonicity can be accomplished using sodium chloride or other pharmaceutically acceptable agents such as dextrose, boric acid, sodium tartrate, propylene glycol, polyols (such as mannitol and sorbitol), or other inorganic or organic solutes. Sodium chloride is preferred particularly for buffers containing sodium ions. If desired, solutions of the above compositions can also be prepared to enhance shelf life and stability. Therapeutically useful compositions of the invention can be prepared by mixing the ingredients following generally accepted procedures. For example, the selected components can be mixed to produce a concentrated mixture which may then be adjusted to the final concentration and viscosity by the addition of water and/or a buffer to control pH or an additional solute to control tonicity.

For use by the physician, the compositions can be provided in dosage form containing an amount of a vector of the invention which will be effective in one or multiple doses to induce β-ASP transgene delivery/expression at a desired level. As will be recognized by those in the field, an effective amount of therapeutic agent will vary with many factors including the age and weight of the patient, the patient's physical condition, and the level of enhancement of cardiac function desired, and other factors.

For viral vectors, the effective does of the compounds of this invention will typically be in the range of at least about $10^7$ viral particles, preferably about $10^9$ viral particles, and more preferably about $10^{11}$ viral particles. The number of viral particles may, but preferably does not exceed $10^{14}$. As noted, the exact dose to be administered is determined by the attending clinician, but is preferably in 1 ml phosphate buffered saline.

The presently most preferred mode of administration in the case of heart disease is by intracoronary injection to one or both coronary arteries (or to one or more saphenous vein or internal mammary artery grafts or other conduits) using an appropriate coronary catheter. A variety of catheters and delivery routes can be used to achieve intracoronary delivery, as is known in the art. For example, a variety of general purpose catheters, as well as modified catheters, suitable for use in the present invention are available from commercial suppliers such as Advanced Cardiovascular Systems (ACS), Target Therapeutics and Cordis. Also, where delivery to the myocardium is achieved by injection directly into a coronary artery (which is presently most preferred), a number of approaches can be used to introduce a catheter into the coronary artery, as is known in the art. By way of illustration, a catheter can be conveniently introduced into a femoral artery and threaded retrograde through the iliac artery and abdominal aorta and into a coronary artery. Alternatively, a catheter can be first introduced into a brachial or carotid artery and threaded retrograde to a coronary artery. Detailed descriptions of these and other techniques can be found in the art (see, e.g., the references cited above, including: Topol, E J (ed.), The Textbook of Interventional Cardiology, 2nd Ed. (W. B. Saunders Co. 1994); Rutherford, R B, Vascular Surgery, 3rd Ed. (W. B. Saunders Co. 1989); Wyngaarden J B et al. (eds.), The Cecil Textbook of Medicine, 19th Ed. (W. B. Saunders, 1992); and Sabiston, D, The Textbook of Surgery, 14th Ed. (W. B. Saunders Co. 1991)).

The following Examples are provided to further assist those of ordinary skill in the art. Such examples are intended to be illustrative and therefore should not be regarded as limiting the invention. A number of exemplary modifications and variations are described in this application and others will become apparent to those of skill in this art. Such variations are considered to fall within the scope of the invention as described and claimed herein.

EXAMPLES

Example 1

General Methods

Example 1-1

Animals and Surgical Procedures

Animal use was in accordance with NIH guidelines. Sixteen Yorkshire pigs (Sus scrofa) weighing 42±5 kg were used for this study, and were anesthetized with ketamine (50 mg/kg, im) and atropine sulfate (0.1 mg/kg, im) followed by sodium amytal (100 mg/kg, iv). After endotracheal intubation, halothane (0.5–1.5%) was delivered by a pressure-cycled ventilator throughout the procedure. At left thoracotomy, catheters were placed in the aorta, pulmonary artery, and left atrium. A Konigsberg micromanometer was placed into the left ventricular apex and an epicardial unipolar lead was placed 1.0 cm below the atrioventricular groove in the lateral wall of the left ventricle. The power generator (Spectrax 5985; Medtronic Incorporated, Minneapolis, Minn.) was inserted into a subcutaneous pocket in the abdomen. The pericardium was loosely approximated and the chest closed.

Ten days after thoracotomy, baseline measures of hemodynamics and left ventricular function were made. Ventricular pacing then was initiated (225 bpm). Five of these animals underwent assessment of hemodynamic and ventricular function 96 hours after initiation of pacing and then were killed. Six animals underwent weekly studies of hemodynamics and ventricular function and were killed twenty-eight days after initiation of pacing. The five remaining animals (controls) were not paced and were killed thirty-eight days after instrumentation.

Example 1-2

Hemodynamic Studies

Hemodynamic data were obtained from conscious, unsedated animals after the pacemaker had been inactivated for 1 hr and animals were in a basal state. Pressures were obtained from the left atrium and aorta. Left ventricular dP/dt was obtained from the high fidelity left ventricular pressure.

Example 1-3

Echocardiographic Studies

Two-dimensional and M-mode images were obtained using a Hewlett Packard Sonos 1500 imaging system. Images were obtained from a right parasternal approach at the mid-papillary muscle level and recorded on VHS tape. Measurements were made using criteria from the American Society of Echocardiography (Sahn D J, et al., Circulation 58: 1072–1083, 1978). End-diastolic dimension (EDD) and end-systolic dimension (ESD) were measured on at least 5 beats and averaged. End-diastolic dimension was obtained at the onset of the QRS complex. End-systolic dimension was taken at the instant of maximum lateral position of the interventricular septum, or at the end of the T wave. Left ventricular systolic function was assessed using fractional shortening [(EDD-ESD)/EDD]×100. The coefficient of variation for end-diastolic dimension on repeated measurements was <5%. All of these measurements were obtained with pacemakers inactivated.

Example 1-4

Terminal Thoracotomy

After four days (n=5) or twenty-eight days (n=6) of continuous pacing (or a similar post-operative duration without pacing for the five control animals), pigs were anesthetized, and midline sternotomies made. Hearts were removed, rinsed in sterile saline (4° C.), and the coronary arteries perfused with sterile saline (4° C.). Transmural samples of the left ventricular free wall were taken mid-way from base to apex, near the midportion of the left anterior descending coronary artery. Myocardial samples were then frozen (−80° C.). Time from heart removal to placing samples in liquid nitrogen was 5–10 min.

Example 1-5
Membrane Assessment and Preparation

Frozen transmural samples (−80° C.) were powdered in a stainless steel mortar and pestle (also −80° C.), placed in Tris buffer, glass-glass homogenized, and contractile proteins extracted (0.5 M KCl, 20 min, 4° C.). The pellet of a 45,000×g centrifugation was resuspended in buffer. Protein concentrations were determined by the method of Bradford (Bradford M M, Anal. Biochem, 72: 248–254, 1976); the protein yield (mg protein/mg wet weight) was assessed in all preparations. We have previously shown that the activity of p-nitrophenyl-phosphatase (Bers D M, Biochem Biophys Acta, 555: 131–146, 1979), a sarcolemmal membrane-associated enzyme used to assess membrane protein yield per mg crude membrane homogenate, is not altered in this model (Roth D A, et al., J. Clin Invest, 91: 939–949, 1993).

Example 1-6
Adenylylcyclase Assays

Methods for measuring AC activity were modified from Salomon (Salomon Y, et al., Anal Biochem, 58: 541–548, 1974) as previously reported (Hammond H K, et al., Circulation 85: 269–280, 1992; Hammond H K, et al., Circulation 8:, 666–679, 1992). The following agents were used to stimulate cAMP production (final concentrations): isoproterenol (10 $\mu$M), GTP (10 $\mu$M), Gpp[NH]p (100 $\mu$M), forskolin (100 $\mu$M). We found that cAMP production under these conditions was linear with respect to time and protein concentration, and that 3-isobutyl, 2-methylxanthine (1.0 mM), adenosine deaminase (5 U/ml), or both, had no effect on basal or maximally stimulated cAMP production. Previous experiments established that AC activity does not distribute to the supernatant of a 45,000×g centrifugation in our membrane preparation (Hammond H K, et al., Circulation 85: 269–280, 1992).

Example 1-7
$\beta$-Adrenergic Receptor Binding Studies

As previously described (Hammond H K, et al., Circulation 8:, 666–679, 1992) $\beta$ARs were identified using the radioligand [$^{125}$I]-iodocyanapindolol. Agonist affinity was determined by performing competitive binding assays using (−)isoproterenol (Hammond H K, et al., Circulation 8:, 666–679, 1992).

Example 1-8
Assessment of Gs$\alpha$ and Gi$\alpha_2$ Content by Immunoblotting Assessment of $\alpha$s and $\alpha$i subunits of Gs and Gi, respectively, was conducted using standard SDS-PAGE and immunoblotting techniques as previously described (Roth D A, et al., FEBS Lett, 29: 46–50, 1992). Briefly, 100 $\mu$g of protein from each supernatant and pellet fraction of a 45,000×g centrifugation of crude myocardial homogenate derived from appropriate transmural samples was electrophoresed on a 10% denaturing gel for 4 hours at 30 mA. Proteins were electroblotted onto nitrocellulose membranes (Amersham, U.K.) for 14 hours, 70 volts, 4° C. Transfer efficiency was recorded by photocopies of membranes dyed with reversible Ponceau staining, and gel retention checked with Coomasie Blue staining. Background blocking was accomplished by incubating membranes in Tris-buffered saline (TBS, pH 7.5) with 2% non-fat dry milk, 2 hours, 25° C. Purified primary polyclonal antibodies (NEN, Boston Mass., rabbit Anti-G-proteins: RM/1 Gs$\alpha$; AS/7, transducin, Gi$\alpha_1$, Gi$\alpha_2$) were diluted 1:600 in 15 ml of TBS with 0.05% Tween-20 (TTBS, pH 7.5) and 1% non-fat dry milk, and membranes incubated for 14 hours, 4° C. Autoradiographic detection of bands was performed by incubating membranes in 75 ml TTBS with 1% non-fat dry milk and 15×10$^6$ cpm $^{125}$I-Protein A (NEN, Boston, Mass.) for 2 hours, 25° C. followed by thorough sequential washes in TTBS, and placing against X-ray film (Kodak X-OMAT AR) for 5 days, −70° C. The 45 and 40 kDa bands for Gs$\alpha$ and Gi$\alpha_2$ were removed from the membranes with background controls for gamma counting.

Example 1-9
Assessment of GRK$_2$ and GRK$_5$ Content by Immunoblotting

Assessment of left ventricular GRK$_2$ and GRK$_5$ content was conducted using standard SDS-PAGE and immunoblotting techniques as previously reported (Ping P, et al., J. Clin Invest, 95: 1271–1280, 1995; Roth D A, et al., FEBS Lett, 29: 46–50, 1992). An antibody specific for purified bovine GRK$_2$ and purified bovine GRK$_2$ were provided by Dr. Jeffrey L. Benovic. An antibody specific for GRK$_5$ was obtained from Santa Cruz Biotechnology (Santa Cruz, Calif.). Transmural left ventricular samples were placed in a lysis buffer containing 20 mM Tris HCl (pH 7.5), 2 mM EDTA, 10 $\mu$g/ml benzamidine, 10 $\mu$g/ml leupeptin, 100 $\mu$g/ml PMSF and 5 $\mu$g/ml pepstatin A. Powdered samples were homogenized then centrifuged and resuspended by sonication in lysis buffer. Eighty $\mu$g of protein from each left ventricular sample was mixed with Laemmli buffer and boiled, then electrophoresed on a 10% denaturing gel. Proteins were transferred to PVDF paper (Immobolin-P, Millipore); transfer efficiency was determined by Ponceau staining. The membrane was blocked for 2 hr in Tris-buffered saline containing 0.1% Tween-20 and 5% non-fat dry milk and developed by conventional methods using GRK$_2$ or GRK$_5$ antiserum followed by exposure to horseradish peroxidase-lined anti-rabbit immunoglobulin (1:1000 in TBS). The blots were developed by the ECL method and bands were visualized after exposing blots to X-ray film. Densities of bands co-migrating with purified bovine GRK$_2$ were quantified by densitometric scanning; for GRK$_5$, we quantified the GRK$_5$-specific band migrating at approximately (68 kD).

Example 1-10
G-Protein Receptor Kinase Activity

GRK enzymatic activity was determined using light-dependent phosphorylation of rhodopsin (Benovic J L, Methods Enzymology, 200: 351–363, 1991) as we have previously reported (Ping P, et al., J. Clin Invest, 95: 1271–1280, 1995). No GRK subtype-specific activity assay is available so phosphorylation of rhodopsin reflects activity of GRK$_2$ ($\beta$ARK$_1$) and GRK$_5$, the predominant GRK isoforms in the heart (Inglese J, et al., J Biol Chem, 268: 23735–23738, 1993). We purified rhodopsin from rod outer segments obtained from dark-adapted calf retina. Light-dependent phosphorylation of purified rhodopsin was first tested by using recombinant GRK$_2$ (a gift from Dr. J. Benovic). One gram of left ventricle was homogenized in 9 ml lysis buffer (50 mM Tris-HCL, pH 7.5, 5 mM EDTA, 10 $\mu$g/ml benzamindine, 20 $\mu$g/ml leupeptin, 40 $\mu$g/ml PMSF and 5 $\mu$g/ml pepstin A), then centrifuged at 45,000×g for 30 minutes. The pellet was resuspended in 4 ml of lysis buffer with 250 mM NaCl (used to dissociate membrane-associated GRK) and homogenized again in a power-driven glass rotor (4° C.). The pellet suspension was then re-centrifuged and ion exchange columns (Amicon) were used to remove NaCl in the supernatant of the pellet suspension. Both the supernatant and the supernatant of the pellet suspension then underwent DEAE-Sephacel column purification to eliminate endogenous kinases that could contaminate GRK-dependent phosphorylation (Ping P, et al., J Clin Invest 95: 1271–1280, 1995; Ungerer M, et al., Circulation, 87: 454–461, 1993). Both supernatant and pellet fractions were independently column-purified.

GRK-dependent phosphorylation was measured by incubating 100 µg protein from either fraction with 250 pmol rhodopsin in buffer containing 18 mM Tris HCl, 1.8 mM EDTA, 4.8 mM MgCl$_2$, 73 µM ATP, and 2.9 cpm/fmol [$^{32}$P]-ATP. The GRK-dependent phosphorylation reaction was confirmed by adding protein kinase A inhibitor (1 µM) and heparin (10 µg/ml) into the reaction. Protein concentration for both pellet and supernatant were determined before and after DEAE-Sephacel purification and the final enzyme activity was expressed as pmol phosphate/min/mg of protein as well as per gram of tissue. We have previously shown that 45,000×g centrifugation (30 min) provides a supernatant which contains less than 1% of the total cellular activity of p-nitrophenylphosphatase (a sarcolemmal membrane-associated enzyme), suggesting excellent separation of cytosolic from membrane components (Roth D A, et al., FEBS Lett, 29: 46–50, 1992).

Example 1-11

RNA Extraction

Total RNA was extracted from left ventricle using a modification of the acid guanidinium thiocyanate-phenol-chloroform extraction method (Chomczynski P, et: al., Anal Biochem, 162: 156–159, 1987) as previously described (Ping P, et al., Am J Physiol, 267: H2079–H2085, 1994; Ping P, et al., J Clin Invest 95: 1271–1280, 1995). Tissue samples were homogenized in 4.0 M guanidinium buffer, extracted twice with acidic phenol-chloroform, and precipitated with isopropanol. The final pellet was washed with 70% ethanol, dissolved in diethylpyrocarbonate-treated water and stored at −80° C. The integrity and purity of the RNA were assessed by gel electrophoresis and the ultraviolet absorbance ratio (260 nm÷280 nm); the sample was rejected if the ratio was less than 1.5, or if visual inspection of the gel photograph suggested degradation.

Example 1-12

Polymerase Chain Reaction Cloning

AC isoforms in porcine left ventricle were isolated by the polymerase chain reaction (PCR). Porcine heart RNA was isolated and reverse-transcribed into cDNA using AMV (avian myeloblastosis virus) reverse transcriptase (Life Science Incorporated, St. Petersburg, Fla.). Degenerate primers spanning a total of 207 bp of the putative nucleotide binding region of the AC gene family (Krupinski J, et al., J Biol Chem, 267: 24858–24862, 1992) were used to amplify the porcine heart cDNA AC genes. The primer sequences used included:

(1) 5'-ACGTAGAATTCGG(AG)GA(CT)TGTTA(CT)TACTG-3' (sense strand as shown in SEQ ID NO: 7)

(2) 5'-ACGTTAAGCTTCCA(GC)AC(AG)TC(AG)AA(CT)TGCCA-3' (antisense strand as shown in SEQ ID NO: 8)

Complementary DNA derived from 5 µg of total RNA was amplified with 4 µM PCR primers in 10 mM Tris-HCl and 50 mM KCl reaction buffer (pH 8.3). Taq DNA polymerase (2.5 units) was used (Gibco BRL). The amplification reaction was run for 30 cycles at 95° C. (2 min), 52° C. (2 min), and 72° C. (2 min), followed by extension at 72° C. for 10 min.

Example 1-13

Construction of Porcine Riboprobes

The PCR fragments obtained from the above reaction were subcloned into pGEM 4Z vectors (Promega) and sequenced. Among the twenty-eight clones sequenced, sixteen type VI, eleven type V, and one type II AC clones were identified based on the published sequences from the rat (Krupinski J, et al., J Biol Chem, 267: 24858–24862, 1992). Porcine and rat AC types II and VI have identical predicted amino acid sequences. Porcine AC type V differs from rat AC type V only at a single amino acid. These three porcine AC isoforms share 90% homology with the rat at the nucleotide level (Krupinski J, et al., J Biol Chem, 267: 24858–24862, 1992).

The three sequenced AC isoform plasmids were linearized with either HindIII to generate the control RNA or with EcoR1 to generate the antisense riboprobes for AC types II, V, and VI. In vitro transcription was then performed using either SP6 or T7 polymerase (Promega) to generate the control RNA (214 bp) or antisense riboprobes (219 bp) for subsequent RNase protection assays. Riboprobes synthesized in vitro contain the complementary sequences of both the mRNA and the pGEM 4Z vector, and are therefore longer than the protected band fragment from the porcine RNA sample (mRNA only). The protected band from porcine heart is sized at 207 bp. The longer length of the control RNA, also derived from the extra sequence from the pGEM 4Z vector, protects the in vitro G, synthesized control mRNA from contamination by sample RNA.

Example 1-14

RNase Protection Assay

RNase protection assays methods were performed as described previously (Ping P, et al., Am J Physiol, 267: H2079–H2085, 1994; Ping P, et al., J Clin Invest 95: 1271–1280, 1995). In vitro transcription was carried out to synthesize [$^{32}$P]-labeled riboprobes with specific activities ranging from $1 \times 10^8$ to $5 \times 10^9$ cpm/µg, using the gene constructs described above. Total RNA (20 µg) from tissue and various amounts of in vitro synthesized sense strand control RNA were hybridized with $2-8 \times 10^4$ cpm probe (in 5–8 fold excess of mRNA as determined in preliminary experiments) in 20 µl of 80% formamide, 40 mM Hepes (pH 7.6), 400 mM NaCl, and 1.0 mM EDTA for 12–16 hours (45° C.). Digestion buffer (300 µl) containing 300 mM NaCl, 10 mM Tris-HCL (pH 7.4), 5 mM EDTA, and 20 µg RNase A and 3 units of T1 RNase per µg total RNA was then added and incubated for 30 minutes (37° C.). After treatment with proteinase K and extraction with phenol-chloroform, the RNAse resistant hybrids were precipitated and run on a 6% polyacrylamide urea gel. The $AC_{II}$, $AC_V$, and $AC_{VI}$ mRNA signals were quantitated by counting the excised gel band with a β-counter. After counting, the cpm of control RNA could be expressed as cpm/µg of control RNA. These data then were used to quantitate mRNA levels in myocardial tissue (pmol specific mRNA/g total RNA). The cardiac content of $AC_{II}$, $AC_V$, and $AC_{VI}$ mRNA were calculated from the ratio of their signal to the signal from their sense strand control RNA in the same hybridization reaction. A mammalian 18S riboprobe (400 cpm; plasmid construct from Ambion) was used together with $AC_{II}$, $AC_V$, and $AC_{VI}$ riboprobes in the hybridizations to assess the loading and hybridization conditions for each tissue sample. The high yield and very low specific activity of the 18S riboprobe ($5-8 \times 10^4$ cpm/µg; Megascript, Ambion) was obtained to assure accurate measurement of the 18S transcript from 20 µg of total RNA. RNase resistance (<1%) and riboprobe specificity were confirmed by complete digestion of single stranded antisense riboprobe plus 40 µg of transfer RNA (yeast) with RNase A and T1.

Example 1-15
Northern Blot Analysis of $GRK_2$

A mouse $GRK_2$ ($\beta ARK_1$) cDNA fragment provided by Dr. P. A. Insel was used to assess $GRK_2$ mRNA content in left ventricular samples. Twenty micrograms of total RNA was gel denatured and blotted onto nylon membranes. The Northern blot was hybridized with a [$^{32}$P]-labeled random primer $GRK_2$ cDNA fragment (bp 1134–1688) for 24 h at 42° C. in a buffer containing 5×SSPE, 10×Denhardt's solution, 100 µg/ml salmon sperm DNA, 50% formamide, and 2% SDS. The blot was washed with 2×SSC/0.1% SDS at 27° C. for 15 min.

Example 1-16
Northern Blot Analysis of $GRK_5$

A human $GRK_5$ cDNA probe (Marzo K P, et al., Circ Res, 69: 1546–1556, 1991) provided by Dr. J. Benovic was used to assess $GRK_5$ mRNA content in left ventricular samples. Twenty micrograms of total RNA was gel denatured and blotted onto nylon membrane. The Northern blot was hybridized with a [$^{32}$P]-labeled random primer $GRK_5$ cDNA fragment (bp 383–1540) for 24 h at 42° C. in a buffer containing 5×SSPE, 10×Denhardt's solution, 100 µg/ml salmon sperm DNA, 50% formamide, and 2% SDS. The blot was washed with 2×SSC/0.1% SDS at 27° C. for 30 min, followed by a high stringency wash with 0.12×SSC/0.1% SDS at 42° C. for 30 min.

Example 1-17
Isolated Cardiac Myocytes

Adult porcine cardiac myocytes were obtained by collagenase perfusion of the coronary artery; and cell viability, purity and yield established as previously described (Spinale F G, et al., Circ. Res. 69: 1058–1067, 1991). Cardiac myocytes, devoid of other cell line contaminants, were frozen and subsequently used for RNA extraction. RT-PCR using the AC isoform primers described above was performed. AC isoforms were identified by hybridization (Southern blot) with specific $AC_{II}$, $AC_V$, and $AC_{VI}$ isoform probes. These probes were cloned and sequenced from porcine heart cDNA as described above. Probe specificity was tested and no cross hybridization occurred between $AC_{II}$, $AC_V$, and $AC_{VI}$ isoform probes.

Example 1-19
Statistical Analysis

For indication of statistical significance, data are generally expressed as mean ±1 SD. Specific measurements were compared using repeated measures analysis of variance; post hoc tests were performed using Student's t-test, with the Bonferroni correction for multiple comparisons between group means. The null hypothesis was rejected when $p<0.05$.

Example 2
A Large Animal Model of Congestive Heart Failure

Figure 2:
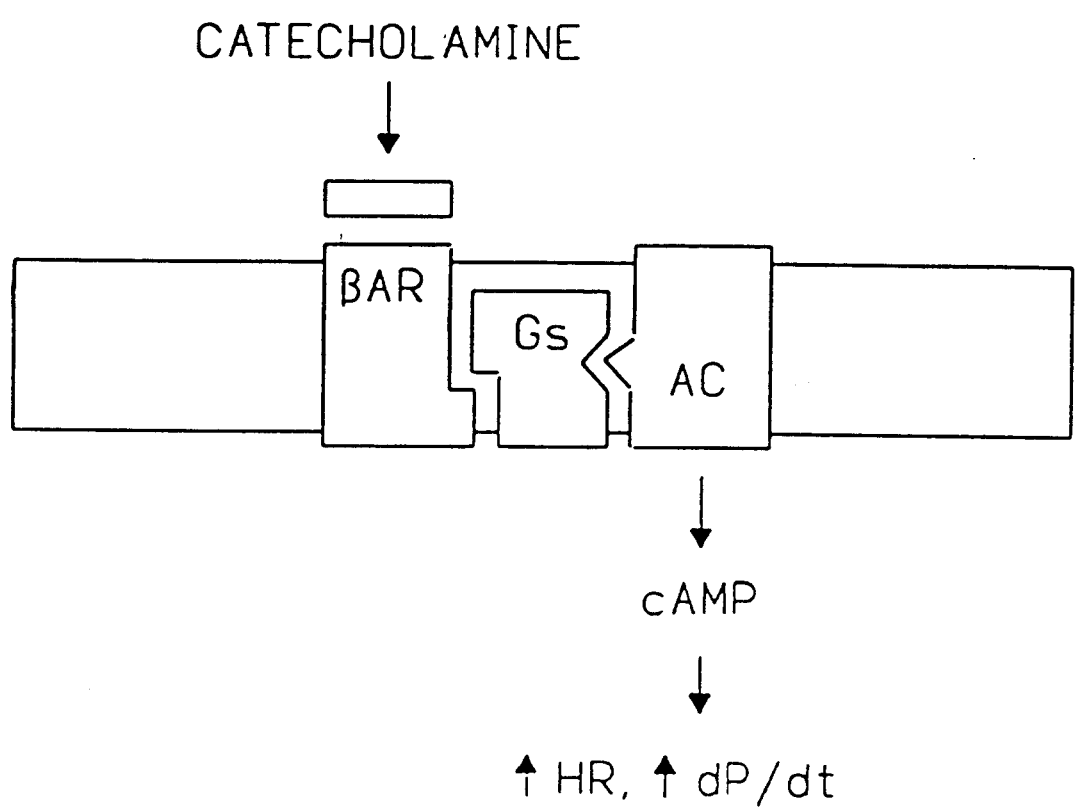
FIG. 2 shows a schematic of the cell surface β-adrenergic-Gs-adenylycyclase pathway. It is through this pathway that β-adrenergic stimulation increases intracellular cAMP thereby influencing heart rate responsiveness and force of contraction. The pathway includes a β-adrenergic receptor, a stimulatory GTP-binding protein (Gs) linking receptor occupation with cAMP production, and an adenylylcyclase, as described in more detail below.

The means by which cardiac myocytes respond to biological signals from the internal environment is through strategically placed cell surface receptors. Principal among these receptors is the β-adrenergic receptor. The transduction pathway by which a hormone or neurotransmitter interacting with a β-adrenergic receptor on the cell surface alters intracellular behavior is known as the β-adrenergic-Gs-adenylylcyclase (or "βAR:Gs:AC") pathway as shown in FIG. 2. It is through this pathway that β-adrenergic stimulation increases intracellular cAMP thereby influencing heart rate responsiveness and force of contraction. The pathway includes three principle components: the β-adrenergic receptor (βAR), the stimulatory GTP-binding protein (Gs) and adenylylcyclase (AC). The molar stoichiometry of components within the βAR:Gs:AC pathway in rat ventricular myocytes, and presumably cardiac myocytes of other mammals, is believed to be about 1:70:1 respectively (see, e.g., Alousi, et al., FASEB J 5:2300, 1991). β-adrenergic signaling within myocardial tissue is initially mediated by agonist binding to βAR, followed by Gs-mediated signal transduction to AC. Activated AC then catalyzes the synthesis of cyclic AMP, and increased intracellular concentrations of cAMP mediate increased cytosolic calcium transients which enhance both the rate and force of cardiac contraction (referred to as positive "chronotrophy" and positive "inotrophy," respectively).

We used a large animal model predictive of humans to examine the possibility that one or more components of the βAR:Gs:AC pathway (as shown in FIG. 2) might effectively limit transmembrane β-adrenergic signaling in cardiac myocytes, and that elevating expression of one or more of the proteins in the pathway might lead to enhanced responsiveness to endogenous β-adrenergic signaling. As exemplary β-ASPs, we have initially focused attention on AC, β-AR, and GRK inhibitors (which indirectly enhance β-AR activity), as described in more detail below.

Example 2-1
Hemodynamics and Left Ventricular Function

As shown in Table 1, rapid ventricular pacing resulted in increased basal heart rate and mean left atrial pressure four days after the initiation of pacing. Data were obtained from sixteen animals (pacemakers inactivated); values represent mean ±1 SD. Groups included normal animals that were not paced (Control, n=5), animals with mild heart failure induced by four days of pacing (4d; n=5), and animals with severe heart failure induced by twenty-eight days of pacing (28d, n=6). LAP, mean left atrial pressure; MAP, mean arterial pressure; EDD, end-diastolic pressure; FS %, % fractional shortening. Analysis of variance (repeated measures) was used to determine whether duration of pacing affected a specific variable.

After four days, animals also showed increased end-diastolic dimension, reduced fractional shortening, and diminished left ventricular peak positive dP/dt. These data indicate mild deterioration of left ventricular function four days after the initiation of continuous rapid pacing.

Cardiac conditions worsened considerably after twenty-eight days of pacing (Table 1), providing a model for heart failure in a large animal considered predictive of humans. Additional evidence establishing the predictiveness of this porcine heart failure model for CHF in humans is described herein and in the art (see, e.g., Roth D A et al., J Clin Invest 91:939–949, 1993, and related references as cited above).

TABLE 1

| HEMODYNAMICS AND LEFT VENTRICULAR FUNCTION | | | | |
|---|---|---|---|---|
| | CONTROL | 4 d | 28 d | p (ANOVA) |
| Heart Rate (bpm) | 100 ± 6 | 131 ± 2[b] | 157 ± 15[c,e] | 0.0001 |
| LAP (mmHg) | 14 ± 1 | 22 ± 3[a] | 36 ± 6[c,e] | 0.0001 |
| MAP (mmHg) | 106 ± 5 | 97 ± 13 | 102 ± 14 | 0.48 |

TABLE 1-continued

HEMODYNAMICS AND LEFT VENTRICULAR FUNCTION

|  | CONTROL | 4 d | 28 d | p (ANOVA) |
|---|---|---|---|---|
| EDD (mm) | 42 ± 2 | 49 ± 3 | 58 ± 6[c,d] | 0.0002 |
| FS (%) | 41 ± 6 | 32 ± 2[a] | 13 ± 4[c,f] | 0.0001 |
| LV dP/dT (mmHg/sec) | 3043 ± 387 | 2036 ± 582[b] | 1072 ± 123[c,d] | 0.0001 |

Data were obtained from sixteen animals (pacemakers inactivated); values represent mean ± 1 SD. Groups included normal animals that were not paced (Control, n = 5), animals with mild heart failure induced by four days of pacing (4 d; n = 5), and animals with severe heart failure induced by twenty-eight days of pacing (28 d, n = 6). LAP, mean left atrial pressure; MAP, mean arterial pressure; EDD, end-diastolic pressure; FS%, % fractional shortening. Analysis of variance (repeated measures) was used to determine whether duration of pacing affected a specific variable. Post hoc testing was performed using Student's t-test with the Bonferroni correction: [a]$p < 0.05$; [b]$p < 0.01$; [c]$p < 0.001$ (vs control); [d]$p < 0.05$; [e]$p < 0.01$; [f]$p < 0.001$ (4 d vs 28 d).

Example 2-2

Necropsy

In animals paced for four days, ascites was present (mean amount: 150 ml; range 0–500 ml). Liver to body weight ratios, compared to previously reported weight-matched control pigs (Roth D A, et al., J. Clin Invest, 91: 939–949, 1993), increased after four days of pacing (Control: 18±3 g/kg, n=15; 4d: 25±2 g/kg, n=5; p<0.0001). Therefore, four days of pacing caused a modest increase in systemic congestion. Left ventricular to body weight ratios, compared to previously reported weight-matched controls (Roth D A, et al., J. Clin Invest, 91: 939–949, 1993) did not increase (Control: 2.7±0.5 g/kg, n=15; 4d: 3.0±0.4 g/kg, n=5; p=0.24).

After twenty-eight days of pacing, liver to body weight ratios were increased two-fold (p<0.0001) and left ventricle to body weight ratios were unchanged, as previously reported (Roth D A, et al., J. Clin Invest, 91: 939–949, 1993).

Example 3

The Role of Adenylylcyclase as a β-Adrenergic Signaling Protein in a Large Animal Model of Congestive Heart Failure The following data indicate that the amount of the exemplary β-ASP adenylylcyclase does in fact impose a limit on β-adrenergic signaling through this pathway in large animal models that are expected to be highly predictive of cardiac function and dysfunction in humans.

Example 3-1

Adenylylcyclase Activity (cAMP Production) After Cardiac Pacing in Pigs

We examined cAMP production to assess the function of adenylylcyclase in left ventricular membranes from normal pigs and from pigs with severe heart failure, using a model of heart failure with very high fidelity to human clinical dilated heart failure (as described by Roth D A, et al., J Clin Invest 91: 939–949, 1993).

After only four days of pacing, isoproterenol-stimulated cAMP production was somewhat reduced (p<0.05) in left ventricular membranes. Forskolin-stimulated cAMP production, an indicator of AC activation independent of β-AR-mediated stimulation, was not significantly affected at this time.

Figure 3:
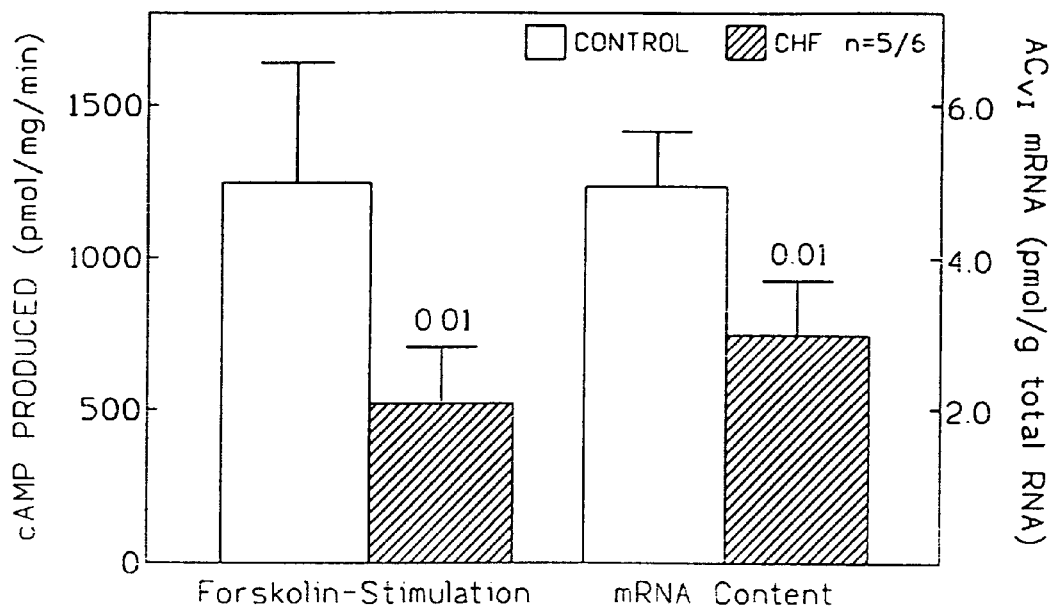
FIG. 3 shows data from experiments using forskolin-stimulated cAMP production to assess the function of adenylylcyclase in left ventricular membranes from normal pigs and from pigs with severe heart failure, using a model of heart failure with very high fidelity to human clinical dilated heart failure, as described in Example 3.

In contrast, twenty-eight days of pacing resulted in substantial reductions in all measures of AC activity. Our results as shown in FIG. 3 (indicating forskolin-stimulated cAMP production), demonstrated that there was in fact a substantial reduction in activity of the β-ASP adenylylcyclase in association with severe heart failure in these animals.

Example 3-2

Identification of AC Isoforms in Cardiac Myocyte Samples

RT-PCR was used to amplify a DNA fragment corresponding to the expected size of AC from cardiac myocyte samples obtained from adult pigs. The DNA fragment was absent when reverse transcriptase was omitted from the reaction.

After hybridization with various AC-specific probes, Southern blots revealed that adult porcine myocytes express AC isoforms II, V, and VI.

Example 3-3

AC mRNA Expression in the Porcine Model

We examined changes in the mRNA levels of AC isoforms (II, V and VI) in normal pigs and in pigs exhibiting heart failure.

After only four days of pacing, there were no significant changes in the mRNA content of the three AC isoforms.

In contrast, as shown in FIG. 3, after 28 days of pacing in the heart failure model, $AC_{VI}$ mRNA was significantly downregulated (p=0.002), whereas $AC_{II}$ and $AC_{V}$ were relatively unchanged. It remains possible that changes in the latter AC isoforms may have occurred at the protein level without substantial changes in mRNA for those isoforms.

Our observations that forskolin-stimulated cAMP production was relatively unchanged until severe heart failure was present indirectly support the idea that AC protein expression was relatively normal during the initial stages of heart dysfunction. However, our data clearly indicate substantial reductions in all measures of AC activity, and downregulation of $AC_{VI}$ protein and mRNA, in association with the onset of more severe heart failure.

Example 4

The Role of β-AR and GRK Inhibitors as β-Adrenergic Signaling Proteins in a Large Animal Model of Congestive Heart Failure As described in the following examples, we also examined the role of β-adrenergic receptor proteins and GRK activity in β-adrenergic signaling in the porcine heart failure model.

Example 4-1

Left Ventricular β-Adrenergic Receptors and G-Protein Content

Despite alterations in left ventricular function and circulatory congestion, four days of pacing was not associated with significant changes in left ventricular β-AR number, or changes in the stimulatory (Gsα) or inhibitory ($Gi\alpha_2$) GTP-binding proteins. However, four days of pacing did result in a reduced proportion of left ventricular β-ARs exhibiting high affinity agonist binding (p<0.01), suggesting an uncoupling of the β-AR from Gsα.

After twenty-eight days of pacing in the heart failure model, we observed substantial downregulation of left ventricular β-AR number, at a time when both Gsα and $Gi\alpha_2$ are also downregulated (Roth D A, et al., J. Clin Invest, 91: 939–949, 1993).

Example 4-2

G-Protein Receptor Kinase Activity

Both cytosolic and membrane fractions of left ventricular homogenates were column-purified and light-dependent phosphorylation of rhodopsin was used to measure GRK activity.

After four days of pacing, animals exhibited increases in left ventricular GRK activity that did not appear to undergo further increases after an additional twenty-four days of pacing (Table 2). A substantial portion (40%) of myocardial GRK activity was associated with the sarcolemma and, although total GRK activity increased in conjunction with the onset of left ventricular dysfunction, the cellular distribution of GRK activity was not altered.

TABLE 2

LEFT VENTRICULAR G-PROTEIN RECEPTOR KINASE ACTIVITY

|  | CONTROL | 4 d | 28 d | p(ANOVA) |
| --- | --- | --- | --- | --- |
| CYTOSOL | 21 ± 4 | 30 ± 8$^a$ | 28 ± 2$^a$ | 0.04 |
| MEMBRANE | 15 ± 2 | 18 ± 2 | 21 ± 3b | 0.005 |
| TOTAL | 35 ± 5 | 48 ± 9$^b$ | 49 ± 2$^b$ | 0.01 |
| % IN CYTOSOL | 59 ± 3 | 63 ± 12 | 57 ± 7 | 0.52 |

G-protein receptor kinase activity in left ventricular membranes. Data from sixteen animals; groups included normal animals that were not paced (Control, n = 5), animals with mild heart failure induced by four days of pacing (4 d; n = 5), and animals with severe heart failure induced by twenty-eight days of pacing (28 d, n = 6). Values are mean ± 1 SD and represent $^{32}$P incorporated (fmol/mg/min). Analysis of variance (repeated measures) was used to determine whether duration of pacing affected a specific variable. Post hoc testing was performed by Student's t-test with the Bonferroni correction: $^a$p ≤ 0.05; $^b$p <0.01 (vs control).

Example 4-3
G-Protein Receptor Kinase$_2$ Protein Content

A band estimated to be 80 kD, co-migrating with purified bovine GRK$_2$, was identified with the GRK$_2$ antibody. LV total GRK$_2$ protein content was unchanged by mild heart failure (4 d pacing) but tended to decrease in LV from animals with severe heart failure (Control: 1.37±0.17 du/μg; 4 d: 1.58±0.34 du/μg; 28 d: 1.02±0.07 du/μg; p<0.02 by ANOVA). However, post hoc analysis revealed that the only group mean comparisons that were statistically significant was 4 d vs 28 d (p<0.03). GRK$_2$ concentration was reduced in the supernatant (p<0.04), but not the pellet fraction of the LV homogenate in severe heart failure.

Example 4-4
G-Protein Receptor Kinase$_5$ Protein Content

A band migrating at 68 kD, identifying GRK$_5$, was detected using the GRK$_5$ antibody. LV total GRK$_5$ protein content was increased by mild heart failure (4 d pacing) and increased further in severe heart failure (Control: 0.62±0.16 du/μg; 4 d: 0.97±0.16 du/μg; 28 d: 1.33±0.25 du/μg; p=0.0004 by ANOVA; Control vs 4 d, p<0.04; Control vs 28 d, p<0.001).

Example 4-5
G-Protein Receptor Kinase$_2$ mRNA Content

An mRNA species estimated to be 3.8 kb was identified with the GRK$_2$ probe. An additional species of 2.4 kb was also noted. LV GRK$_2$ mRNA content was unchanged by mild heart failure (4 d pacing) but was reduced in LV from animals with severe heart failure (Control: 67±11 du; 4 d: 66±16 du; 28 d: 45±13 du; p=0.02 by ANOVA; Control vs 28 d, p=0.02; 4 d vs 28 d, p<0.03). We were unable to detect GRK$_3$ (βARK$_2$) expression either with PCR or by Northern blotting.

Example 4-6
G-Protein Receptor Kinase$_5$ mRNA Content

An mRNA species estimated to be 3.0 kb was identified with the GRK$_5$ probe. LV GRK$_5$ mRNA content was upregulated within 4 d of the initiation of pacing, a finding that persisted for 28 d (Control: 54±4 du; 4 d: 110±28 du; 28 d: 96±17 du; p=0.001 by ANOVA; Control vs 4 d: p=0.003; Control vs 28 d: p=0.01).

Example 4-7
β-AR and GRK Inhibitors as β-Adrenergic Signaling Proteins (β-ASPs)

Results obtained in our large animal model of heart failure confirmed that reduced β-AR responsiveness in heart failure is associated with selective down-regulation of myocardial β$_1$-AR and β$_1$-AR mRNA levels; β$_2$-AR expression and mRNA content do not change (see, e.g., Bristow M R et al., J Clin Invest 92: 2737–2745, 1993; Ping P, et al., Am J Physiol, 267: H2079–H2085, 1994; Ungerer M, et al., Circulation, 87: 454–461, 1993); and that remaining β-ARs are uncoupled from Gs (the stimulatory GTP-binding protein which links receptor activation with AC stimulation), as reflected by a reduction in high affinity agonist binding (see, e.g., Bristow M R, et al., Mol Pharm, 35: 295–303, 1989; Bristow M R, et al., J Clin Invest, 92: 2737–2745, 1993). Mechanisms for β-AR uncoupling in CHF have not been firmly established. GRK, primarily studied in cells with β$_2$-ARs, phosphorylates the β$_2$-AR after adrenergic activation (Hausdorff W P, et al., FASEB J, 4: 2881–2889, 1990; Inglese J, et al., J Biol Chem, 268: 23735–23738, 1993), and may play a role in β-AR desensitization in the setting of sustained sympathetic activation, as occurs in CHF. After β$_2$-AR stimulation by agonist, GRK$_2$ translocates from cytosol to sarcolemma, phosphorylates the β$_2$-AR, and thereby uncouples the β$_2$-AR and Gs, thus attenuating the signal (Hausdorff W P, et al., FASEB J, 4: 2881–2889, 1990; Inglese J, et al., J Biol Chem, 268: 23735–23738, 1993). A role for GRK-mediated phosphorylation of the β$_1$-AR has recently been demonstrated, a phosphorylation that can be mediated both by GRK$_2$ and GRK$_5$ (Freedman N J, et al., J Biol Chem, 270: 17953–17961, 1995; Koch W J, et al., Science, 268: 1350–1353, 1995). In addition, chronic reduction of β$_1$-AR activation (bisoprolol treatment) results in downregulation of GRK activity and enhanced adrenergic signaling, suggesting that the extent of adrenergic activation may influence GRK expression (Ping P, et al., J Clin Invest 95: 1271–1280, 1995). Recent studies have suggested that GRK activity is also increased in the soluble fraction of left ventricular homogenates of failing human hearts (Salomon Y, et al., Anal Biochem, 58: 541–548, 1974; Ungerer M, et al., Circ Res, 74: 206–213, 1994).

Our findings with respect to GRK activity in the porcine heart failure model are also similar to those reported by Ungerer et al (Ungerer M, et al., Circulation, 87: 454–461, 1993), in that left ventricular GRK activity is increased in failing left ventricle. However, there are several aspects of our data which are quite new with respect to GRK expression in the setting of heart failure. First, unlike previous reports, we measured GRK activity in both soluble and particulate fractions. While heart failure does not affect the sarcolemmal/cytosolic distribution of GRK activity, severe heart failure is associated with increased myocardial GRK activity in both fractions. A second new finding is that the increase in total GRK activity was an early event in heart failure, occurring prior to alterations in β-AR number, G-protein content, or AC isoform expression or catalyst activity. To the extent that increased GRK activity may serve to phosphorylate and uncouple Gs and the β-AR, we also have demonstrated a potential biochemical correlate of increased GRK activity. In conjunction with decreased numbers of β-ARs showing high affinity agonist binding, we found reduced hormonal stimulation of cAMP that correlated temporally with increased total GRK activity. Third, total GRK$_5$ protein and mRNA content were increased, also at this early time point, and these elevations persisted in severe heart failure. These data support the idea that increased myocardial GRK expression predates other changes in adrenergic signaling in heart failure, and thus appears to be an important early event in the pathogenesis. A previous study found increased GRK activity and increased GRK$_2$ mRNA (using PCR) in explanted failed human left ventricles (Ungerer M, et al., Circulation, 87: 454–461, 1993). However, we found reduced LV GRK$_2$ mRNA levels by Northern blotting. The discrepancy regarding LV GRK$_2$ mRNA levels in the present study vs the human studies may reflect different methods employed to assess mRNA, different models employed, or the difficulty in obtaining true control material in the human studies. We also note that GRK$_5$ was not examined in the cited report. While we do not rule out a role for GRK$_2$ in severe heart failure, our data support the idea that GRK$_5$ may plait a more important role.

Increased GRK activity was detected in the soluble fraction of LV membranes from animals with mild heart failure, while GRK$_2$ and GRK$_5$ protein content were not significantly increased in the soluble fraction. This may indicate a disparity between enzymatic activity and protein content, or may reflect methodological differences in protein distribution in the membrane preparations used for the enzymatic assay vs immunoblotting studies.

The present study documents, for the first time, that myocardial GRK$_5$ protein and mRNA contents are susceptible to upregulation in mild and severe heart failure. Without wishing to be bound by theory, our data support the idea that increased expression of GRK$_5$ may be responsible for the increased GRK activity observed in these clinical conditions. In any case, the current data strongly support the hypothesis that increased left ventricular GRK expression contributes to reduced adrenergic signaling at an early stage during the development of heart failure.

Example 5
Construction of a Vector for Gene Delivery of Adenylylcyclase as an Exemplary β-ASP As an illustration of the construction of a gene delivery vector for use in the present invention, we have prepared constructs using a helper-independent replication-defective viral vector as described above. In particular, in this example, we demonstrate the generation of replication-defective adenoviral constructs based on the human adenovirus-5 system (see, e.g., McGrory W J, et al., Virology 163: 614–617, 1988).

As an exemplary β-adrenergic signaling protein (β-ASP), we initially selected an adenylylcyclase protein, in particular adenylyicyclase isoform VI (AC$_{VI}$). We therefore constructed vectors comprising either AC$_{VI}$ (as an illustrative β-ASP), or lacZ (as an illustrative detectable marker gene which encodes β-galactosidase). The system used to generate recombinant adenoviruses (based on these "first-generation" vectors) imposes packaging constraints that are believed to increase as the size of the transgene insert exceeds about 5 kb. in the case of control elements such as a CMV promoter and an SV40 polyadenylation signal (which together comprise approximately 1 kb), the transgene itself (i.e. without additional control elements) would therefore preferably be less than about 4 kb. Although smaller transgenes are therefore preferred, we have also shown that substantially larger transgenes can nevertheless be employed, even in these "first generation" vectors. For example, in a first exemplary β-ASP transgene, described in Example 5-1, we used essentially the entire transcribed region from a murine adenylylcyclase gene (approximately 5748 bp), together with a heterologous CMV promoter (approximately 790 bp) and an SV40 polyadenylation signal (approximately 230 bp). As described in detail below, we have shown that such transgenes (including more than 6.7 kb with control elements) can nevertheless be incorporated and effectively used with these first generation vectors.

However, in view of the known packaging constraints of these particular vectors, and as another exemplary β-ASP transgene, we constructed an altered adenylylcyclase gene in which an untranslated region of the transcript was deleted to generate a shorter β-ASP transgene. In the illustrative embodiment described below in Example 5-2, the 3'-untranslated region from the AC$_{VI}$ gene was removed, and the resulting construct was incorporated into a vector for delivery of the transgene to the heart, as described herein. As will be apparent, the desirability of truncating the transgene (in the case of a size-constrained viral vector such as Ad or AAV) depends in part on the length of the native gene, as well as the choice of control elements used. In the case of Ad, where the total insert size exceeds about 5 kb, the transgene can be truncated, preferably in the 3'-untranslated region, to result in a shorter insert. As is also apparent, the preferred extent of truncation depends on the insert size, but is typically at least about 100 bp, more preferably at least about 500 bp, still more preferably at least about 1000 bp (particularly if the total insert size is still greater than about 5 kb). We have shown that the entire 3'-untranslated region can be readily deleted from the AC$_{VI}$ isoform, resulting in a substantial shorter transgene. First generation AAV vectors are also size constrained and efficiency decreases with inserts significantly greater than about 5 kb. For these and other such vectors, however, "second generation" derivatives can provide additional space for transgene packaging. Other viral vectors, as well as various non-viral vectors, can be used to accommodate substantially larger inserts.

Example 5-3 describes the identification of sequences encoding a human adenylylcyclase gene. As described herein, such human β-ASP transgenes can be obtained by screening of human DNA libraries (using probes from homologous mammalian genes), and such human β-ASP transgenes can be usefully employed in the context of the present invention. In particular, where the therapeutic target is a human heart, it is expected that the use of human β-ASP transgenes can provide additional advantages (including potentially closer coordination with other components of the β-adrenergic signaling pathway, as well as further minimizing the possibility of a host response to non-human proteins). The isolation and sequencing of an exemplary human β-ASP transgene is described below in Example 5-3.

Other illustrative β-ASP transgenes, including genes encoding β$_1$-adrenergic receptors (β$_1$-AR) and GRK inhibitors are described in Examples 6 and 7.

Example 5-1
Generation of a β-ASP Transgene Using a Full Length AC$_{VI}$ cDNA

For generation of a first exemplary β-ASP transgene, we used a cDNA encoding murine AC$_{VI}$ (a Ca(2+)-inhibitable AC from murine NCB-20 cells as reported by Yoshimura M and Cooper D M, Proc Natl Acad Sci (USA) 89: 6716–6720, 1992, referred to in the paper as "pAC-V", now known as "pAC-VI"; see also Krupinski, J., et al., J. Biol. Chem. 267: 24858–24862, 1992). The full length AC$_{VI}$ cDNA was cloned into the polylinker of plasmid ACCMVPLPA (J Biol Chem 267: 25129–25134, 1992) which contains the CMV promoter and the SV40 polyadenylation signal flanked by partial adenovirus sequences from which the E1A and E1B genes, which are essential for viral replication, had been deleted. The resulting plasmid was co-transfected (by lipofection) into human 293 cells with plasmid JM17 (Giordano, et al. Nature Medicine 2: 534–539, 1996) which contains the entire human adenovirus 5 genome as well as an additional 4.3 kb insert (thereby making pJM17 too large to be encapsidated).

Homologous rescue recombination resulted in the generation of recombinant adenovirus vectors containing the transgene ($AC_{VI}$ or lacZ) in the absence of E1A/E1B sequences (as illustrated in FIG. 1). Although these recombinants were nonreplicative in normal mammalian cells, they can be propagated in human 293 cells which had been transformed with E1A/E1B (and therefore provided these essential replication gene products in trans).

Transfected human 293 cells were monitored for evidence of cytopathic effect which usually occurred 10–14 days after transfection. To identify successful recombinants, cell supernatant from plates showing a cytopathic effect was treated with proteinase K (50 mg/ml with 0.5% sodium dodecyl sulfate and mM EDTA) at 56 degrees C. for 60 minutes, followed by phenol/chloroform extraction and ethanol precipitation. Successful recombinant viral vectors were then identified by PCR using primers complementary to the CMV promoter and SV40 polyadenylation sequences to amplify the insert, and primers designed to concomitantly amplify adenovirus sequences (as in Biotechniques 15:868–872, 1993).

Successful recombinant viral particles were then subjected to two rounds of plaque purification. Viral stocks were further propagated in human 293 cells to titers ranging between $10^{10}$ and $10^{12}$ viral particles, and were purified by double CsCl gradient centrifugation prior to use following standard procedures. Briefly, cells were infected at 80% confluence and harvested at 36–48 hours; and, after freeze-thaw cycles, the cellular debris was collected by standard centrifugation and the virus further purified by double CsCl gradient ultracentrifugation (discontinuous 1.33/1.45 CsCl gradient; cesium prepared in 5 mM Tris, 1 mM EDTA (pH 7.8); 90,000×g (2 hr), 105,000× g (18 hr)).

Prior to in vivo injection, the viral stocks were typically desalted by gel filtration through Sepharose columns such as G25 Sephadex. The resulting viral stock had a final viral titer in the $10^{10}$–$10^{12}$ viral particles range. The viral preparation was found to be highly purified, with essentially no replicative virus present (as determined by an absence of cytopathic effect after transfection of the vector into human host 293 cells).

Example 5-2

Generation of a Second β-ASP Transgene Using a Truncated Adenylylcyclase Gene

As another illustrative β-ASP transgene, we constructed an altered adenylylcyclase gene in which an untranslated region of the normal transcript was removed to generate a shorter β-ASP transgene. In particular, we essentially removed the 3'-untranslated region from an $AC_{VI}$ construct, and incorporated the resulting truncated transgene into a viral vector for gene delivery.

Figure 1B:
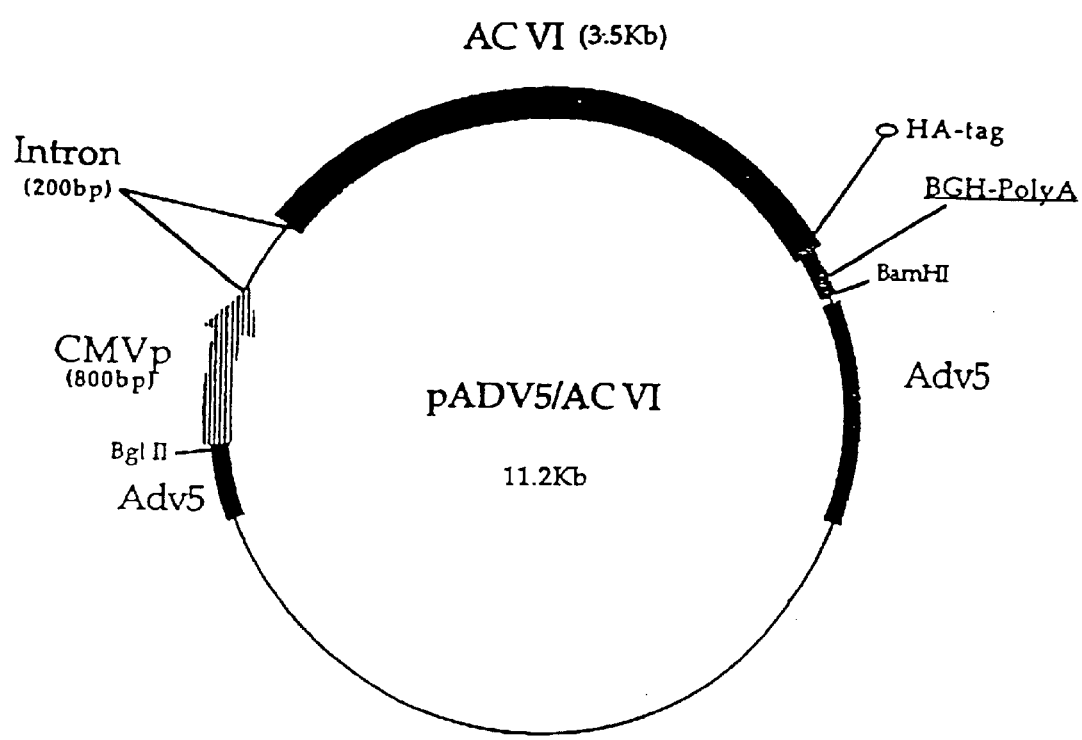
FIG. 1B shows a schematic of a clone used in the construction of an exemplary replication-defective recombinant adenovirus vector useful for gene transfer into cells and into the heart, as described in Example 5–2 below.

Plasmid Construction and Recombinant Adenovirus Production. A murine $AC_{VI}$ cDNA without the 3'-untranslated region was constructed as follows. A subfragment containing the 3' portion of $AC_{VI}$ with an Xho I site at its 5' end was generated using two PCR primers: $AC_{VI}$PX, which anneals to $AC_{VI}$ cDNA at bases 2500–2521; and $AC_{VI}$p3'HA which contains sequences from the 3' end of $AC_{VI}$ and sequences from human influenza hemoagglutinin. The PCR product was digested with restriction enzymes Xho I and Xba I which were designed in the primers at the 3' end. The 5' portion of the $AC_{VI}$ fragment (base pair −92 to +2500) was obtained by Eco RI and Xho I digestion of the full length cDNA (as described above) and was isolated on an agarose gel. Two $AC_{VI}$ fragments were then subcloned into an Eco RI-Xba I digested adenovirus vector (pAd5Cl, a gift of Dr. Swang Huang, The Scripps Research Institute, La Jolla, Calif.) by three molecule ligation. The pAd5/Cl vector contains a cytomegalovirus immediate-early enhancer/promoter region (CMV promoter), a chimeric intron, and a multicloning site derived from pCl plasmid DNA (Promega, Madison, Wis.). It also contains a bovine growth hormone polyadenylation (poly A) sequence and partial human adenovirus-5 sequences. Introduction of the two $AC_{VI}$ fragments into the EcoRI-XbaI digested plasmid, as noted above, resulted in the generation of plasmid pADV5/$AC_{VI}$ which is depicted in FIG. 1B (abbreviations: AC VI—Adenylylcyclase VI; CMVp—Cytomegalovirus immediate-early enhancer/promoter region; HA-tag—Hemagglutinin protein of influenza virus—tag; BGH-poly A—Bovine growth hormone-poly A; Adv5—Adenovirus 5).

Following procedures as described above, the $AC_{VI}$-containing vector was cotransfected (calcium phosphate) into a human embryonal kidney cell line (H293) with pJM17 which contains the adenovirus genome except the E1 region. After recombination, plaques were selected and expanded in H293 cells. H293 cells have been transformed with adenovirus E1, and therefore provide this viral transcription factor in trans. Expression of $AC_{VI}$ was examined by RT-PCR and Western blot analysis. Virus was purified by cesium chloride ultracentrifugation and desalted by column filtration through Sephadex G-25 equilibrated with PBS as described above. The viral concentration was determined by optical densitometry at $OD_{260}$. Plaque-forming units (pfu) were assayed by plaque titration using H293 cells overlaid with agarose-DMEM medium.

Identification of $AC_{VI}$ Expressing Clones. To identify adenovirus clones that expressed $AC_{VI}$, sixteen clones were screened by RT-PCR using a pair of specific primers ($AC_{VI}$PX and $AC_{VI}$p3'HA) which hybridize to transgene $AC_{VI}$ but not endogenous $AC_{VI}$ in H293 cells. The 512-bp RT-PCR product was confirmed by digestion with the restriction enzyme Apa I to produce 312-bp and 200-bp fragments. Three of sixteen clones expressed $AC_{VI}$ mRNA. Expressed as fold increase in cAMP production, all three clones showed increased cAMP production in response to stimulation by isoproterenol (Clone 1, 22-fold increase; Clone 2, 15-fold increase; Clone 3, 12-fold increase) and forskolin (Clone 1, 16-fold increase; Clone 2, 11-fold increase; Clone 3, 13-fold increase). Clone 1 was selected for additional analyses using cardiac myocytes as described in Example 8-2.

Example 5-3

Generation of a Third β-ASP Transgene Using a Human Adenylylcyclase Gene

As discussed above, β-ASP genes exist in many mammalian tissues, with different isoforms typically predominating in certain tissue types. In the case of adenylycyclases, as noted above, there tends to be a predominance of isoforms II, V and VI in cardiac tissues. Such genes also tend to exhibit a fairly significant degree of sequence conservation between different mammals, particularly with respect to the isoforms found in a specific tissue such as the heart. DNA hybridization and associated molecular biological techniques can thus be employed to identify additional β-ASP transgenes for use in the context of the present invention.

By way of illustration, we have identified clones in a human heart cDNA library that were homologous to a murine $AC_{VI}$ cDNA fragment as a means of obtaining the human $AC_{VI}$ gene. Identification of the human sequence will thus permit the use of the corresponding human β-ASP transgene according to the methods described herein. Briefly, a human heart cDNA library (commercially available from Clontech, #HL3026b) was screened with an SphI fragment of about 1.9 kb from the murine $AC_{VI}$ cDNA using standard molecular biological techniques as described in the references cited above. Six positive clones were identified in the primary screen and confirmed in secondary and tertiary screens. Three of these clones (designated clones 1, 4 and 5) were sub-cloned into a vector for sequencing. We employed the "Bluescript" vector pBS-SK (commercially available from Stratagene). The first round of sequencing was carried out using T3 and T7 primers, and then internal primers were employed for subsequent sequencing. All three of the clones contained sequences that were highly homologous to $AC_{VI}$ genes of other species including the mouse. These clones, and sub-fragments thereof, were used to identify overlapping clones containing the remaining sequence. From the overlapping clones we obtained the nucleotide sequences (SEQ ID NOS: 1 and 3), which correspond to more than 2 kb of the presumed 3.4 kb coding sequence of human $AC_{VI}$. SEQ ID NOS: 2 and 4 depict the amino acid sequences corresponding to the nucleotide sequences shown in SEQ ID NOS: 1 and 3, respectively. From the sequence information provided in SEQ ID NO: 1 or 3, the complete nucleotide sequence encoding the full length human $AC_{VI}$ and variants thereof can be readily obtained using standard recombinant DNA methodology. The complete nucleotide sequence of human $AC_{VI}$ as obtained is shown in SEQ ID NO: 5. The corresponding amino acid sequence is depicted in SEQ ID NO: 6.

Polynucleotides comprising closely related sequences can likewise be obtained, using techniques such as hybridization, as is known in the art. Such sequences would include, for example, those exhibiting at least about 80% overall sequence identity, preferably at least 90%, even more preferably at least 95% sequence identity with a nucleotide sequence comprising that shown in SEQ ID NO. 1 or 3 or 5. Isolated polynucleotides that hybridize at high stringency to a polynucleotide having the nucleotide sequence of SEQ ID NO. 1 or 3 or 5 can thus be readily obtained based on standard molecular biological techniques. These polynucleotides can also be used to obtain isolated polypeptides encoded by the polynucleotides. As used in this context, an "isolated polypeptide" or protein is a polypeptide or protein which has been substantially separated from any cellular contaminants and components naturally associated with the protein in vivo. The phrase embraces a polypeptide which has been removed from its naturally occurring environment, and includes recombinant polypeptide and chemically synthesized analogues or analogues biologically synthesized by heterologous systems. An "isolated polynucleotide" is similarly defined. The variants will include allelic variants. An "allelic variant" in the context of a nucleic acid or a gene is an alternative form (allele) of a gene that exists in more than one form in the population. At the polypeptide level, "allelic variants" generally differ from one another by only one, or at most, a few amino acid substitutions. There can also be synthetic or "unnatural" variants of a gene that are generated by recombinant biological techniques. Preferably, the amino acid residue positions which are not identical in the variant differ by conservative amino acid substitutions. "Conservative amino acid substitutions" refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine.

The ACVI polynucleotides encoding variants can also comprise silent nucleotide subtitutions. By "silent" subtitution is meant that the substituted nucleotide does not result in an amino acid change at the protein level. Even more substantial nucleotide changes can be introduced into regions that do not affect the enzymatic activity of the encoded adenycyclase polypeptide. Many such polynucleotides will encode polypeptides that maintain adenycyclase enzymatic activity, which can be tested by routine methods as known in the art. "High stringency" conditions for polynucleotide hybridization are described, e.g., in J. Sambrook et al., supra, and typically refer to conditions in which the salt concentration and the temperature are increased such that only sequences having substantial overall sequence identity (typically in excess of 80%, more preferably in excess of 90%) over stretches of greater than about 100 nucleotides remain hybridized.

As will be appreciated by those of skill in the art, small fragments of the human $AC_{VI}$ polynucleotide sequence (including fragments on the order of about 15–50 nucleotides) can be used as primers or probes to identify and isolate isoforms or variants of the native polypeptides.

Isolated polypeptides encoded by the polynucleotides of the preceding embodiments include, for example, polypeptides comprising a sequence in which at least about 300 amino acid residues is at least 80% (preferably 90%, even more preferably 95%, most preferably greater than 98%) identical with a sequence of comparable length within SEQ ID NO. 2 or 4 or 6.

Example 6

Construction of a Vector for Gene Delivery of a β-Adrenergic Receptor Protein ($β_1$-AR) as a Second Type of β-ASP As described above, other preferred β-adrenergic signaling proteins for use in the present invention include β-adrenergic receptor proteins, particularly $β_1$-adrenergic receptors ($β_1$-AR), and GRK inhibitors (which can indirectly enhance β-AR activity as described above).

Gene delivery vectors comprising transgenes encoding such additional β-ASPs can be readily generated using techniques such as those described in the preceding example.

By way of illustration, we have constructed a recombinant replication-defective adenovirus vector expressing a human β-adrenergic receptor. As an exemplary β-AR, we used a full length cDNA encoding human $β_1$-AR (about 1.8 kb) as described and sequenced in Frielle, et al., PNAS (USA) 84: 7920–7942, 1987).

Briefly, the $β_1$-AR cDNA fragment (which had been cloned into the EcoRI site of pSP65) was inserted into an E1-deleted recombinant human adenovirus-5 vector using the techniques described in the preceding example, thereby generating a recombinant vector for the delivery of a gene encoding a second preferred β-ASP (i.e. a β-adrenergic receptor protein).

Example 7
Illustrative Construction of a Vector for Gene Delivery of a GRK Inhibitor as a Third Type of β-ASP Yet another illustrative example of a β-adrenergic signaling protein for use in the present invention is a G-protein receptor kinase inhibitor (GRK inhibitor), which can be used to indirectly enhance β-AR activity and therefore β-adrenergic responsiveness. Gene delivery vectors comprising transgenes encoding such a β-ASP can be readily generated using techniques such as those described in the preceding examples.

Since the functional kinase domains of various GRK proteins have been identified (and corresponding domains in related GRK proteins can be identified by homology), and the mutation need only impair kinase functionality (which is testable using standard techniques), a variety of GRK inhibitors can be readily prepared. By way of illustration, a GRK inhibitor can be constructed as described for the "β-ARK 1-minigene" (Koch, et al., Science 268: 1350–1353, 1995), or an analogous construct (in which a GRK is mutated to effectively delete or impair kinase function without disrupting receptor binding activity) can be used.

Briefly, the DNA fragment encoding the GRK inhibitor can be inserted into an E1-deleted recombinant human adenovirus-5 vector using the techniques described in the preceding examples, or using another vector as known in the art.

Example 8
Rapid Screening of Vector Constructs for β-ASP Gene Transfer and Expression Using Neonatal Rat Ventricular Myocytes in Cell Culture β-ASP gene transfer vectors can initially be tested by examining the ability of the vectors to deliver β-adrenergic signaling proteins to ventricular cells maintained in cell culture. Such cell culture studies can thus be useful in screening putative gene transfer vectors (having, e.g., particular combinations of β-ASP transgenes and promoters) for the ability to deliver expressible transgenes to cells of particular types, such as exemplified herein.

The first round of such screening can be conveniently accomplished using a standard detectable marker gene (such as lacZ) so that gene delivery and gene expression can be readily and rapidly quantified, as illustrated below.

Vectors that effectively deliver and cause expression of the first round "test" transgene (e.g. a detectable marker gene) can then be subjected to a second screening round using a β-ASP according to the present invention.

By way of illustration of such vector screening techniques, neonatal rat ventricular myocytes were prepared with a collagenase-containing perfusate according to standard methods. Rod-shaped cells were cultured on laminin-coated plates and at 48 hours were infected with a vector comprising a detectable marker gene (viz. an adenovirus vector comprising a lacZ gene, as described in the examples above) at a multiplicity of infection of 1:1 (plaque forming units: cell). After a further 36 hour period, the cells were fixed with glutaraldehyde and incubated with X-gal.

Examination of staining revealed that essentially all exposed cardiac myocytes expressed the product of the lacZ transgene (i.e. β-galactosidase) after infection with the recombinant adenovirus vector in cell culture.

Example 8-1
Delivery of a β-ASP Transgene to Cardiac Myocytes Derived from Mammalian Ventricles Experiments were then performed to examine the ability of the gene transfer vectors to deliver and express a β-adrenergic signaling protein in the ventricular myocytes. Forty-eight hours after culture, myocytes were infected with recombinant vectors, as in Example 5, comprising either a β-ASP gene ($AC_{VI}$) or a detectable marker gene (lacZ).

Twenty-four hours after gene transfer, cells were incubated with and without isoproterenol (10 μM) in the presence of $^3$H-forskolin, to assess the degree of forskolin binding as a measure of AC protein content. In additional studies, $AC_{VI}$ mRNA content was assessed in Northern blots.

Figure 4:
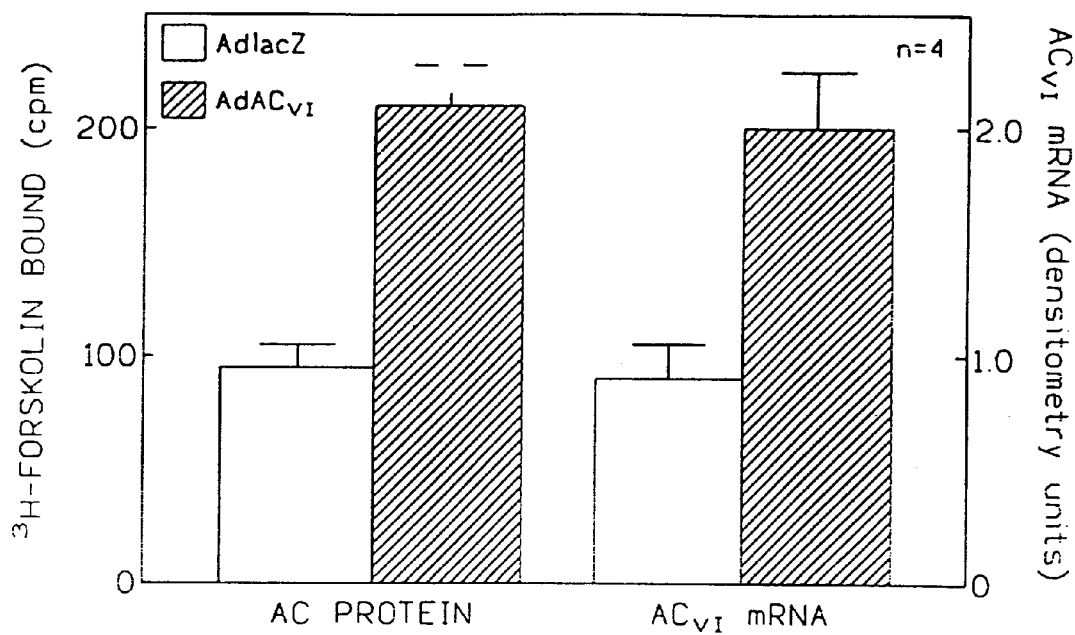
FIG. 4 shows data indicating that AC content sets a limit upon βAR-mediated signal transduction in cardiac myocytes, as described in Example 8–1.

As shown in FIG. 4, cells exposed to vectors carrying the β-ASP transgene $AC_{VI}$ had a 2-fold increase in AC protein content and mRNA, confirming successful gene transfer and expression of $AC_{VI}$ in cardiac myocytes in vitro using viral vectors.

Additional experiments were conducted on cultured neonatal rat ventricular myocytes to examine cAMP production in myocytes following delivery of the β-ASP transgene $AC_{VI}$. Forty-eight hours after culture, myocytes underwent infection with recombinant adenovirus expressing either $AC_{VI}$ or lacZ. Twenty-four hours after gene transfer, cells were incubated with isoproterenol (10 μM) or forskolin (3 μM) and cAMP content was measured.

Figure 5:
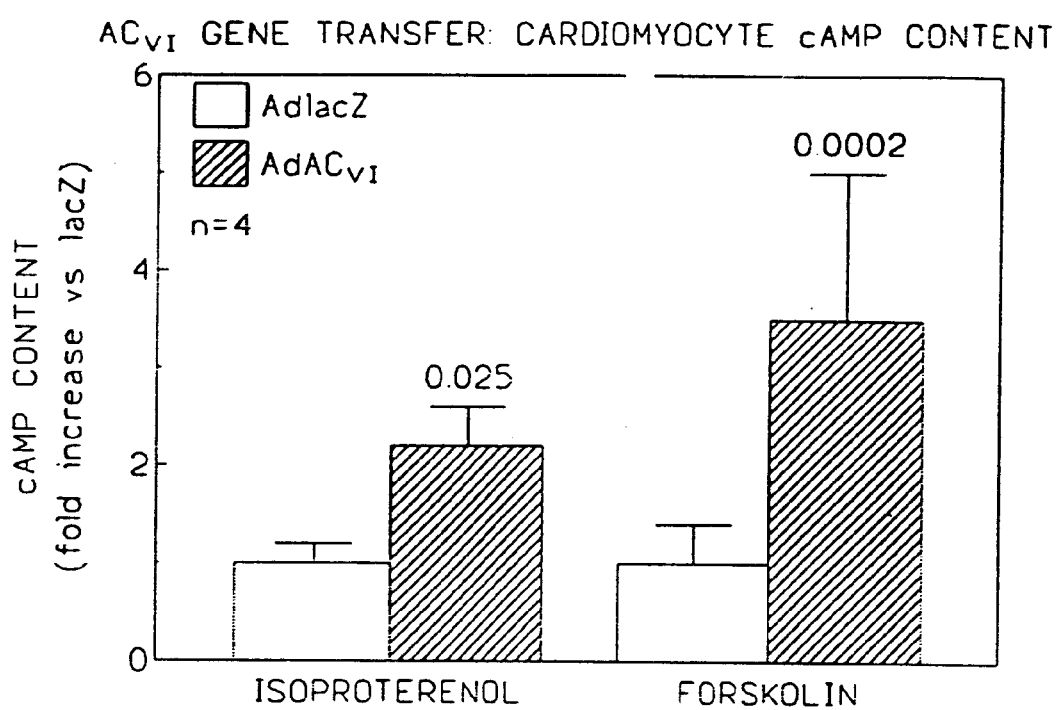
FIG. 5 shows data indicating that gene transfer of an $AC_{VI}$ transgenes to cultured neonatal rat ventricular myocytes increased the levels of cAMP obtained after stimulation with either isoproterenol (10 $μM$) or forskolin (3 $μM$), as described in Example 8–1.

As shown in FIG. 5, cells exposed to vectors carrying the β-ASP transgene $AC_{VI}$ exhibited a 2-fold increase in isoproterenol-stimulated cAMP content, and an 3-fold increase in forskolin-stimulated cAMP content.

These rapid-screening techniques are also applicable to the testing of other vectors, as described herein, including other vectors (e.g. other viral vectors such as AAV as well as non-viral vectors including lipid-based vectors and various non-viral delivery platforms), vectors in which transgenes are linked to different transcriptional control sequences (such as ventricular-specific promoters), as well as vectors encoding other β-ASP transgenes, as described and illustrated herein.

Example 8-2
Delivery of a Truncated β-ASP Transgene to Cardiac Myocytes Derived from Mammalian Ventricles As an additional illustration, we delivered a truncated β-ASP transgene (constructed as described in Example 5-2) to cardiac myocytes that had been derived from the ventricles of a mammalian heart, and assessed expression of the transgene and the encoded protein in the treated cardiac cells.

We also analyzed the physiological effects of transgene delivery to the ventricular myocytes (as measured by alterations in forskolin binding and cAMP production), and examined β-adrenergic receptor binding in the cells (using radioligand binding assays).

Cardiac Myocyte Preparation and Gene Transfer. Hearts from 1 to 2 day old Sprague-Dawley rats were removed, atria and great vessels discarded, and ventricles trisected. Myocardium was digested with collagenase II (Worthington) and pancreatin (GibcoBRL Life Technology, Gaithersburg, Md.), and the myocardial cell suspension was centrifuged through Percoll step gradients to separate cardiac myocytes from other cells. Cells then were plated ($4 \times 10^4$ cells/cm$^2$) in plates precoated with gelatin, and incubated for 24 h. Cells were then washed with serum-free media and maintained in 2% fetal bovine serum for 24 h (as described in Knowlton, K U et al, J Biol Chem 266: 7759–7768, 1991). Adenovirus-mediated gene transfer was performed 3 d after initial isolation by adding recombinant adenovirus expressing $AC_{VI}$ or lacZ (10 pfu/cell), and incubating for 20 h in DMEM containing 2% fetal bovine serum. Adenovirus was removed and the cells were maintained for 24 h and then used for study. The extent of gene transfer was evaluated by X-gal staining of cells after gene transfer with lacZ. Preliminary studies established that at virus titers of 1, 10, and 100 pfu per cell, 95–100% of cardiac myocytes expressed lacZ with no evidence of cytotoxicity. We selected 10 pfu/cell for our studies. Protein content per plate was similar after gene transfer with lacZ and $AC_{VI}$.

RT-PCR. RT-PCR was used to identify $AC_{VI}$ mRNA. The reverse transcription reaction was performed (SuperScript II, GibcoBRL Life Technology). Briefly, 1 μg of mRNA was mixed with 100 ng of the primer $AC_{VI}3'pHA$ in 11 μl, heated (70° C., 10 m) and quickly chilled on ice. Four microliters of 5×first strain buffer, 2 μl of 0.1 M DTT, and 1 μl of 10 mM dNTP were added and the reaction mixture allowed to equilibrate (37° C., 2m). Finally, 1 μl (200 units) of Super-Script II Rnase H reverse transcriptase was added; reaction duration was 1 h (37° C.).

Northern Blot Analysis. Total RNA was isolated from cardiac myocytes 48 h after gene transfer using Trizon reagent (GIBCOBRL Life Technology). Twenty micrograms of denatured total RNA was electrophoresed in 1×MOPS/EDTA buffer on a 1.0% agarose gel. The RNA was transferred to a nylon membrane in 20×SCC solution. RNA was immobilized (80° C., 2 h); and the membrane hybridized with randomly labeled $^{32}$P-dCTP murine $AC_{VI}$ cDNA probe or glyceraldehyde-3-phosphate dehydrogenase (GADPH). Hybridization was carried out in Hood buffer (50% formamide, 5×SSC, 20 mM NaHPO4, pH6.7, 7% SDS, 1% PEG 15,000–20,000, and 0.5% non-fat milk) at 42° C. for 16 h. The membrane was washed once with 2×SSC-0.5% SDS for 30 m at RT, and 2–3 times with 0.1×SSC-0.1% SDS for 30 m each (60–65° C.) and exposed to X-ray film.

Figure 6:
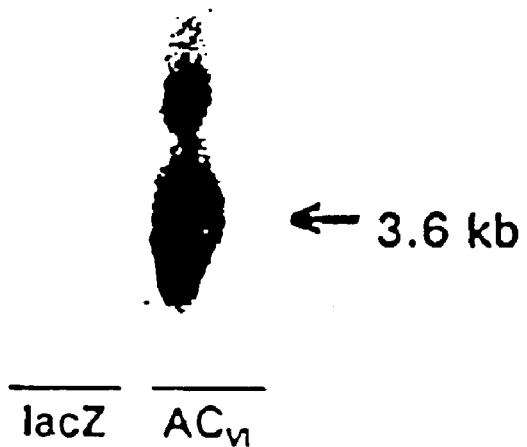
FIG. 6 shows data from a Northern analysis indicating the presence of transgenes mRNA in cardiac myocytes, as described in Example 8–2.

The resulting Northern blots showed a band compatible with $AC_{VI}$ mRNA in RNA isolated from cardiac myocytes that had received $AC_{VI}$ gene transfer (FIG. 6). The low abundance endogenous rat $AC_{VI}$ mRNA was detectable after prolonged exposure in cells that had received lacZ gene transfer. Equal RNA loading was documented by GADPH controls. These data document robust transgene $AC_{VI}$ mRNA expression after gene transfer.

Western Blot Analysis. Cell lysates were prepared from virus infected myocytes by using NP-40 lysis buffer (20 mM Hepes pH7.0, 120 mM HCl, 1 mM DTT, 5 mM magnesium acetate, 10% glycerol, 0.5% NP-40, and proteinase inhibitors: 10 μg/ml each of leupeptin, aprotinin, and pepstatin, and 1 mg/ml of pefabloc ) for 10 m on ice. The samples were centrifuged in a microfuge at full speed for 15 m at 4° C. The pellet was resuspended in 1×SDS buffer. Samples were boiled (5 m) and cell lysates loaded onto a 7.5% SDS-polyacrylamide gel (SDS-PAGE). Protein was electrophoretically transferred (1 h, 100V, 4° C.) to nitrocellulose membranes in Tris-glycine buffer (25 mM Tris-HCl pH 8.3, 150 mM glycine, and 10% methanol). The membranes were treated with blocking buffer consisting of 5% nonfat dry milk in Tris-saline buffer (0.9% NaCl and 10 mM Tris-HCl, pH 7.5). For detection of $AC_{VI}$ protein, membranes were incubated with anti-ACV/VI antibody (Santa Cruz Biotechnology, Inc., Santa Cruz, Calif.) diluted 1:100 in blocking buffer for 1 h (RT). For detection of Gsα and Giα$_2$1 membranes were incubated with anti-Gsα or anti-Giα$_2$ antibodies as previously described (as in Ping et al., J. Clin. Invest. 95: 1271–1280, 1995). Primary antibodies were detected with goat anti-rabbit IgG horseradish peroxidase conjugate (GIBCOBRL Life Technology) in blocking buffer. The antigen then was visualized with chemiluminescent substrates A and B (Kirkegaard and Perry Laboratories, Gaithersburg, Md.) and exposed to X-ray film.

Figure 7:
FIG. 7 shows data from a Western analysis indicating the presence of transgenes protein in cardiac myocytes, as described in Example 8–2.

The resulting Western blots revealed that endogenous rat $AC_{VI}$ protein could not be detected in cells after gene transfer with lacZ. However in cardiac myocytes that had received $AC_{VI}$ gene transfer, transgene $AC_{VI}$ protein was easily detectable as a band of appropriate electrophoretic mobility (FIG. 7). These data document robust transgene $AC_{VI}$ protein expression after gene transfer.

Forskolin Binding. [$^3$H]Forskolin-binding assays were conducted using a modification of published methods (Post S R, Biochemical Journal 311: 75–80, 1995). Briefly, myocytes were infected with either adenovirus expressing ACV or lacZ, and cultured for 48 h in 12-well culture plates. Prior to assay, culture medium was aspirated and the cells washed in reverse buffer (100 mM KCl, 20 mM NaCl, 1 mM NaH$_2$PO$_4$, 20 mM HEPES, and 1 mM MgSO$_4$, pH 7.4). Binding assays were initiated by the addition of saponin (20 μg/ml final), 20 nM [$^3$H]forskolin, 1 μM 1,9-dideoxyforskolin (to reduce association of radiolabel with non-adenylylcyclase molecules) and the additions indicated in the figure legends. Cells were incubated in a final volume of 0.5 ml for 15 min at 25° C. Reactions were terminated by aspiration of media and cells were washed twice with ice-cold washing buffer (50 mM Tris, 10 mM MgCl$_{21}$ pH 7.4). The amount of [$^3$H]forskolin associated with cells was determined by extraction of cells in 0.2% Triton X-100 and scintillation counting of the soluble cell extract.

Cyclic AMP Measurements. Prior to treatment of cells, growth medium was removed and cells were equilibrated for 30 m (RT) in serum- and sodium bicarbonate-free DMEM supplied with 20 mM HEPES pH 7.2. Subsequently, cells were incubated for 10 m (RT) in fresh DMEM containing either 10 μM isoproterenol, or 10 μM forskolin in the presence of 0.1 mM ascorbic acid (to prevent oxidization) and 250 μM IBMX, a phosphodiesterase inhibitor. The reaction was terminated by aspiration of medium and addition of 7.5% ice-cold trichloroacetic acid (TCA). TCA extracts were frozen (−20° C.) until assayed. Intracellular cAMP levels were determined by radioimmunoassay (Calbiochem, San Diego, Calif.) of TCA extracts following acetylation according to the protocol provided by the manufacturer. The sensitivity of this assay allowed for large dilution of TCA extracts such that ether extraction of TCA was unnecessary. Production of cAMP was normalized to the amount of acid-insoluble protein assayed by the BioRad protein assay.

Statistical analysis. For the forskolin binding and cAMP production studies, data are reported as mean values±1 SD. Data were compared using Student's t-test and, where appropriate, analyses of variance. The null hypothesis was rejected when p<0.05.

Figure 8A:
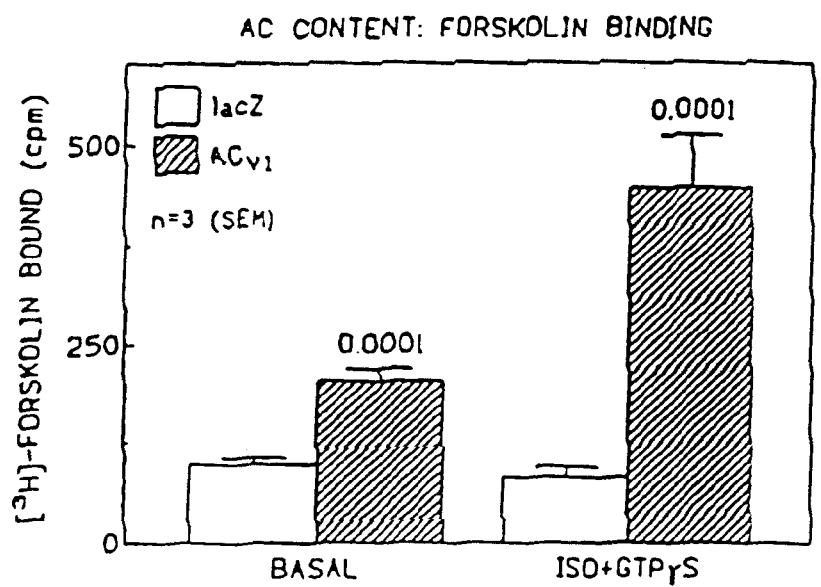
FIG. 8A shows data from a forskolin binding study indicating that net GTPγ-stimulated forskolin binding was increased after $AC_{VI}$ gene transfer (data are mean values from three experiments), as described in Example 8–2.

Results of studies on forskolin binding and cAMP production. Forskolin binding studies provided a means to evaluate the amount of AC available for activation during hormonally-stimulated signaling. Cardiac myocytes that had received gene transfer on the same day, using the same clone, underwent parallel studies designed to measure forskolin binding as well as hormonally-stimulated cAMP production. The rationale for these studies was to obtain an accurate assessment of the relationship between transgene protein expression and cAMP production. Net GTPγS-stimulated forskolin binding was increased after $AC_{VI}$ gene transfer (lacZ: 81±24 cpm; $AC_{VI}$: 447±113 cpm; p<0.0001). These are mean values from three experiments, documenting that transgene $AC_{VI}$ is present and responsive to Gs:AC interaction (FIG. 8A).

Figure 8B:
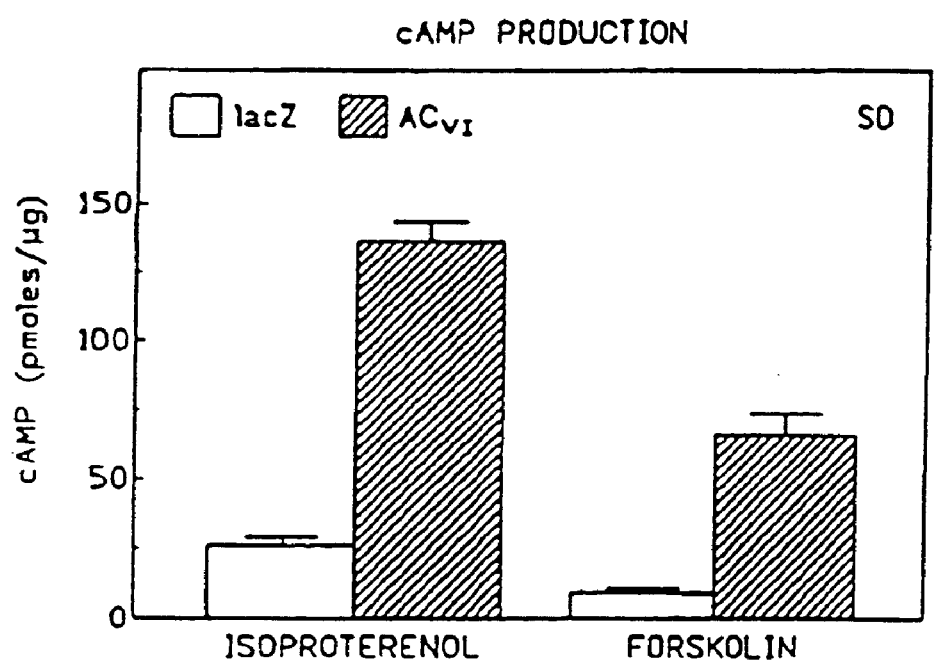
FIG. 8B shows data from a cAMP production study indicating that cardiac myocytes expressing transgenes $AC_{VI}$ have increased adrenergic responsiveness not only to forskolin stimulation, reflecting increased amounts of AC, but to isoproterenol, suggesting that newly synthesized AC is functionally coupled and recruitable through β-AR stimulation, as described in Example 8–2. Shown are mean values from three experiments.

We then measured the responsiveness of cardiac myocytes overexpressing $AC_{VI}$ to hormonal stimulation (FIG. 8B). $AC_{VI}$ gene transfer was associated with increased cAMP production when stimulated by isoproterenol (lacZ:

26±3 pmoles/ug; $AC_{VI}$: 136±7 pmoles/µg; p<0.0001) and by forskolin (lacZ: 9±2 pmoles/µg; $AC_{VI}$: 66±8 pmoles/µg; p<0.0001). These are mean values from three experiments, documenting that cardiac myocytes expressing transgene $AC_{VI}$ have increased adrenergic responsiveness not only to forskolin stimulation, reflecting increased amounts of AC, but to isoproterenol, indicating that newly synthesized AC is functionally coupled and recruitable through βAR stimulation.

Figure 8C:
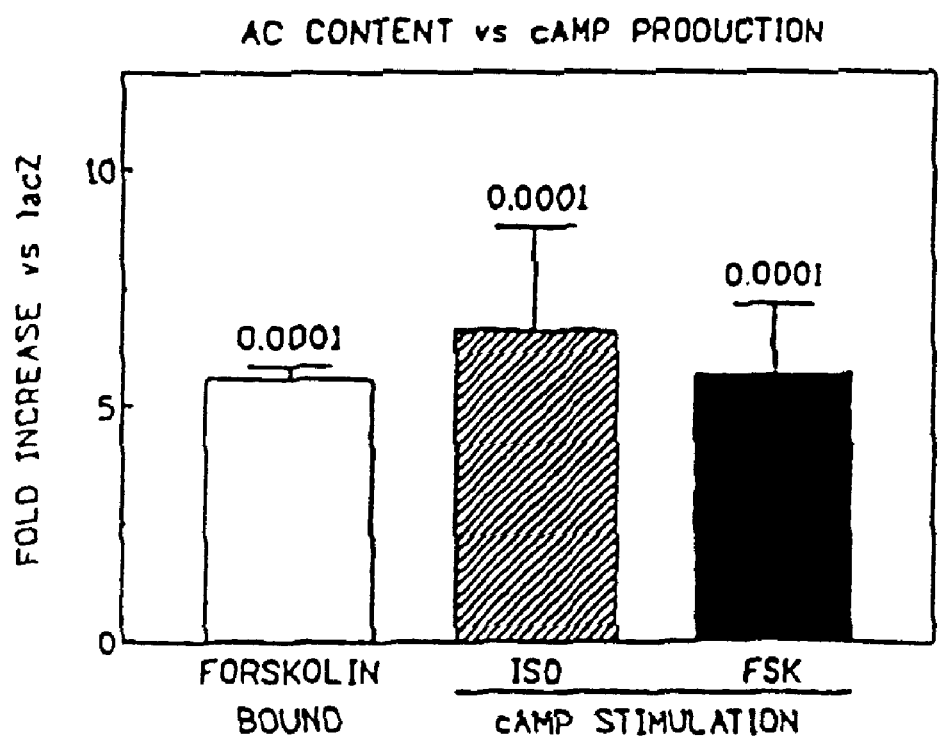
FIG. 8C shows the observed relationship between $AC_{VI}$ content and cAMP production, as described in Example 8–2. The graph displays three measure of altered adrenergic signaling (forskolin binding, and isoproterenol- and forskolin-stimulated cAMP production). These data indicate that a proportional increase in AC content and enhanced adrenergic signaling has occurred.

FIG. 8C displays three measures of altered adrenergic signaling (forskolin binding, and isoproterenol- and forskolin-stimulated cAMP production). These data indicate that a proportional increase in AC content and enhanced adrenergic signaling have occurred.

Figure 9:
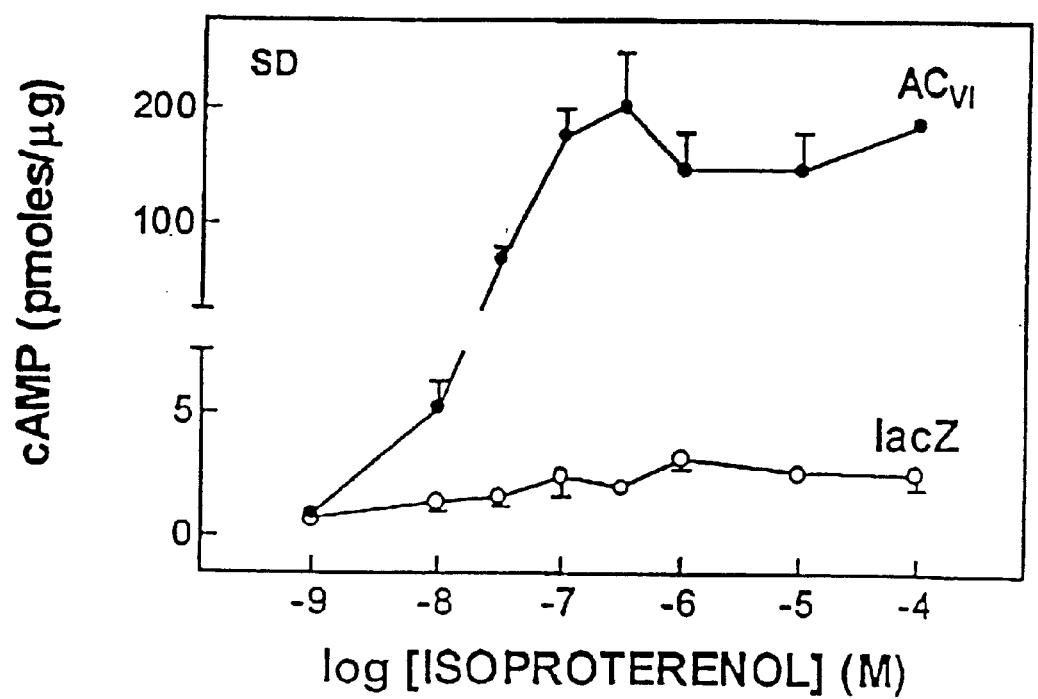
FIG. 9 shows the results of an isoproterenol stimulation study as described in Example 8–2. Neonatal rat cardiac myocytes underwent gene transfer using recombinant adenovirus expressing lacZ or $AC_{VI}$. After gene transfer with $AC_{VI}$ (vs lacZ), there is an obvious increase in cAMP produced through a wide range of isoproterenol concentrations. The EC50 for isoproterenol-stimulated cAMP production was unchanged.

FIG. 9 shows cAMP production when cardiac myocytes were stimulated by a range of isoproterenol concentrations. After gene transfer with $AC_{VI}$ (vs lacZ), there was an obvious increase in cAMP produced through a wide range of isoproterenol concentrations. The EC50 for isoproterenol-stimulated cAMP production was unchanged (lacZ: 16±13 nM; $AC_{VI}$: 32±19 nM).

To determine if lacZ has a deleterious effect on cAMP production, we also studied non-transfected cardiac myocytes. These studies showed that untransfected cells were indistinguishable from lacZ infected cells in cAMP production.

β-Adrenergic Receptor Binding Studies. βARs were identified in radioligand binding experiments using [$^{125}$I]-iodocyanopindolol (ICYP; 30–240 pM); $10^{-4}$M isoproterenol was used to define nonspecific binding. Transfected cells (IlacZ vs $AC_{VI}$) were lysed and membranes prepared for radioligand binding (as in Ping et al., J. Clin. Invest. 95: 1271–1280, 1995); experiments were performed with triplicate samples. Data are reported as specifically bound ICYP (fmol/mg).

To determine whether increased AC content affected βAR number, we performed radioligand binding assays. These assays identified similar amounts of specifically bound ICYP per mg membrane protein in plates of cardiac myocytes infected with adenovirus expressing lacZ (Bmax: 26 fmol/mg; Kd: 43 pM) or $AC_{VI}$ (Bmax: 29 fmol/mg; Kd: 78 pM). These data indicate that βAR number was unchanged by gene transfer of $AC_{VI}$.

Gsα and $Gi\alpha_2$ Content. To determine whether increased AC content affected G protein content, we performed immunoblotting studies with antibodies directed against Gsα and $Gi\alpha_2$. These assays identified similar amounts of Gsα and $Gi\alpha_2$. These data indicate that the content of Gsα and $Gi\alpha_2$ were not changed by gene transfer of $AC_{VI}$.

Summary of studies involving β-ASP transgenes

The experiments described above demonstrate that β-ASP transgenes (including variant transgenes in which untranslated regions have been altered) can be readily constructed and used to deliver β-ASP gene products to cardiac cells, and further confirm that such transgenes can be used to alter the functional responsiveness of the cells.

Deletion of the 3'-untranslated region in the illustrative β-ASP construct resulted in a substantially smaller transgene that was found to be even more effective in mediating transgene expression and functional response following delivery to the ventricular myocytes. Truncated constructs in which untranslated regions are removed from the transgene (e.g. β-ASP transgenes from which the 3'-untranslated regions are removed) can thus provide alternative, highly functional constructs for use in the present invention. As compared to the "parental-type" construct in which the native 3'-untranslated region was maintained, the altered β-ASP transgene resulted in an approximately 4-fold increase in forskolin-stimulated cAMP production, and an approximately 9-fold increase in isoproterenol-stimulated cAMP production. The ability to employ genes exhibiting differing levels of expression thus provides an added tool that can be used to optimize the present invention in the context of varying therapeutic needs (depending on the desired level of expression in the cells and tissue to be treated). Alternatively, by employing such high expression constructs, one can practice the present invention using correspondingly less vector to achieve an equivalent effect. Indeed, despite unchanged numbers of cell surface receptors in these experiments, we were able to amplify cAMP production through βAR stimulation by approximately 2–100 fold using β-ASP transgenes as described and illustrated above.

Without wishing to be bound by theory, the observed increases in effective expression levels using the altered transgene may be due to an increase in vector packaging efficiency and/or an increase in message stability. In those regards, the substantially reduced size of the transgene construct may allow it to be packaged more efficiently in the viral vector used in these experiments. Our results also suggest that the resulting mRNA was more abundant in transfected cells (approximately 25-fold higher as compared to the parental-type construct), which may be the result of an increase in message stability. With respect to the latter, we have identified a potential mRNA destabilizing element depicted in SEQ ID NO: 9 (UUAUUUA(UA)(UA)) in the 3'-untranslated region of the original ACVI construct. Removal of such message destabilizing elements may thus enhance the effective expression of other β-ASP transgenes having such elements.

In addition, our observations that cells overexpressing $AC_{VI}$ showed amplified responsiveness to βAR-mediated stimulation (versus forskolin alone) suggests that newly synthesized AC is functionally coupled and recruitable through stimulation by agonists that are normally present in vivo.

Example 9

Demonstration of In Vivo Gene Transfer to the Myocardium in a Porcine Heart Failure Model In order to examine in vivo gene transfer in a large animal model that would be predictive of CHF in humans, we initially demonstrated delivery and expression of a detectable marker transgene to pig heart myocardium using the β-galactosidase-encoding vector generated as described in the examples above.

Briefly, an adenoviral vector was propagated in permissive human 293 cells and purified by CsCl gradient ultracentrifugation (with a final viral titer of $1.5 \times 10^{10}$ viral particles), based on the procedures of Example 5.

An anesthetized, ventilated 40 kg pig underwent thoracotomy. A 26-gauge butterfly needle was inserted into the mid left anterior descending (LAD) coronary artery and the vector ($1.5 \times 10^{10}$ viral particles) was injected in a 2 ml volume. The chest was then closed and the animal allowed to recover. On the fourth day post-injection, the animal was sacrificed. The heart was fixed with glutaraldehyde, then sectioned and incubated with X-gal for 16.5 hours. After imbedding and sectioning, the tissue was counter-stained with eosin.

Microscopic analyses of tissue sections (transmural sections of the LAD bed)) revealed a significant magnitude of gene transfer in cells of the LAD coronary bed with many tissue sections demonstrating greater than 50–60% of the cells staining positively for β-galactosidase. Areas of the myocardium remote from the LAD circulatory bed did not demonstrate X-gal staining and served as a negative control, while diffuse expression of the gene was observed in myocytes and in endothelial cells.

In additional studies using closed-chest intracoronary injection, substantial activity was present 14 days after gene transfer (n=8).

Using these techniques, we thus demonstrated effective in vivo gene transfer and expression in a large mammal heart, with no evidence of inflammation or necrosis in areas of gene expression.

In view of our demonstration of the efficacy of this system, the in vivo procedure for monitoring delivery and expression of transgenes in the porcine heart failure model can also be readily employed to test other in vivo gene delivery vectors according to the present invention.

As described in Examples 10, 11 and 12 below, this in vivo procedure for monitoring delivery and expression of transgenes in the porcine heart failure model can also be readily employed to test other in vivo gene delivery vectors according to the present invention, including, for example, other in vivo delivery vectors (e.g. other viral vectors such as AAV as well as non-viral vectors including lipid-based vectors and various non-viral delivery platforms), vectors in which transgenes are linked to different transcriptional control sequences (such as ventricular-specific promoters), as well as vectors encoding other β-ASP transgenes, as described and illustrated herein.

As described in Example 13 below, we have also demonstrated that delivery of a β-ASP transgene to the myocardium, in accordance with the present invention, can be used to significantly enhance cardiac function in this large animal model of human heart failure.

Example 10

Illustrative in vivo Gene Transfer to Pig Myocardium Using Other Viral Vectors (AAV)

Other vectors, including various viral vectors (such as adeno-associated virus (AAV)), liposomes and other lipid-containing gene delivery complexes, and other macromolecular complexes (such as multifunctional gene delivery fusion proteins) that are capable of mediating delivery of a polynucleotide to a mammalian host cell in vivo can be used to deliver β-ASP transgenes to the myocardium in accordance with present invention. Thus, for example, AAV can be used to deliver one or more β-ASP transgenes to the myocardium in vivo. The general principles of the preparation and use of adeno-associated viral vectors have been described in the art (see, e.g., Carter, B., Curr. Opin. Biotechnol., 3: 533–539, 1992; Kotin, R., Human Gene Therapy, 5: 793–801, 1994; and Flotte, T. R., et al., Gene Therapy 2:357–362, 1995; and the other references cited above).

By way of illustration, one or more βASP transgenes (preferably comprising less than about 5 kb) as described herein is cloned into a recombinant AAV vector from which some (preferably all) of the AAV coding sequences (i.e. AAV rep and cap genes) have been deleted, but which retains at least the AAV inverted terminal repeats (ITRs). By placing the β-ASP transgene between the AAV inverted terminal repeats and introducing the vector into a permissive packaging cell line capable of providing or modified to provide the missing AAV packaging functions (i.e. Rep and Cap proteins) in trans. The packaging cell line can then be used to replicate and encapsidate the recombinant AAV vector into infective (but replication-defective) AAV particles once the necessary AAV helper virus functions are provided, as described in the art. Alternatively, the recombinant AAV vector can be introduced prior to or coincident with the introduction of the helper virus or helper virus functions. As is known in the art, a variety of helper viruses (or genetic functions derived therefrom) can be used to provide helper activity to AAV, including adenoviruses, herpesviruses and poxviruses such as vaccinia. The most commonly used helper virus is Adenovirus. The deleted AAV packaging functions can be stably introduced into the genome of the packaging cell or they can be provided transiently (by, e.g., transfection with a helper plasmid or by inclusion within the helper virus, such as adenovirus). Recombinant AAV particles are then purified as described in the art (using, e.g., isopycnic ultracentrifugation).

As described in Examples 5–7 above, various β-ASP transgenes are generated for cloning into recombinant vectors, in this case AAV. With first-generation AAV vectors, the transgene or transgenes should comprise less than about 5 kb in order to be efficiently packaged. Of course, different ASP transgenes can also be placed into separate vectors.

Methods such as those illustrated in Example 8 can be used to select vector constructs mediating efficient delivery of β-adrenergic signaling proteins to ventricular cells maintained in cell culture; and, as illustrated in Example 9, a detectable marker gene (such as lacZ) can be used to select vector constructs mediating efficient delivery of transgenes to the myocardium in vivo. Suitable β-ASP vector constructs can then be used (as described in Examples 12–13 below) to deliver β-ASP transgenes to the myocardium in vivo.

Example 11

Illustrative in vivo Gene Transfer to Pig Myocardium Using Non-Viral Vectors

The examples described herein using viral vectors as illustrative gene delivery vehicles can also be readily applied to the use of non-viral vectors, such as liposomes and other lipid-containing gene delivery complexes, and other macromolecular complexes (such as multifunctional gene delivery fusion proteins) that are capable of mediating delivery of a polynucleotide to a mammalian host cell in vivo.

By way of illustration, liposomes and other lipid-containing gene delivery complexes can be used to deliver one or more β-ASP transgenes. The principles of the preparation and use of such complexes for gene delivery have been described in the art (see, e.g., Ledley, F D, Human Gene Therapy 6: 1 129–1144, 1995; Miller, N., et al., FASEB Journal 9: 190–199, 1995; Chonn, A., et al., Curr. Opin. in Biotech. 6: 698–708, 1995; Schofield, J P, et al., British Med. Bull. 51: 56–71, 1995; Brigham, K. L., et al., J. Liposome Res. 3: 31–49, 1993; and the other references cited above).

Briefly, one or more β-ASP transgenes as described herein is introduced into a liposome or other lipid-containing gene delivery complex using techniques known in the art. Various β-ASP transgenes can be generated as described in Examples 5–7, and then introduced into liposomes or other lipid-based vectors. Methods such as those illustrated in Example 8 can be used to select vectors mediating efficient delivery of β-adrenergic signaling proteins to ventricular cells maintained in cell culture; and, as illustrated in Example 9, a detectable marker gene (such as lacZ) can be used to select vectors mediating efficient delivery of transgenes to the myocardium in vivo. Suitable β-ASP vector constructs can then be used (as described in Examples 12–13 below) to deliver β-ASP transgenes to the myocardium in vivo.

Example 12
Effect of Gene Transfer of β-ASP Transgenes in vivo in Large Animal Models Predictive of Heart Failure in Humans Example 12-1
In Vivo Gene Transfer of an Adenylylcyclase β-ASP Transgene to Myocardium In view of the foregoing observations, we examined the ability to enhance β-adrenergic responsiveness in vivo using gene therapy to deliver a β-ASP transgene to the myocardium of our large animal model.

Animals included 3 domestic pigs (weighing 30–40 kg). A left thoracotomy was performed under sterile conditions for instrumentation (as in Hammond, et al. J Clin Invest 92:2644–2652, and Roth, et al. J Clin Invest 91:939–949, 1993).

Catheters were placed in the left atrium and aorta, providing a means to calibrate the left ventricular high fidelity pressure gauge used to measure pressure development, and to monitor pressures. Wires were sutured on the left atrium to permit ECG recording and atrial pacing.

After recovery from surgery (10–14 days), pigs were examined to determine β-adrenergic responsiveness and baseline left ventricular dimension and hemodynamics. The most important element of these studies were heart rate responses to isoproterenol infusion. One of the pigs was also examined for left ventricular dP/dt measurements that were made before and after gene transfer, as described below.

The illustrative adenovirus vector system described above was used to deliver transgenes by in vivo gene delivery. As an exemplary β-ASP transgene, we used the $AC_{VI}$ isoform referred to above. The vector material injected in vivo was highly purified and contained no wild-type (replication competent) adenovirus. Thus adenovirus infection and inflammatory infiltration in the heart were minimized. The vector preparation was injected into the lumen of the coronary artery by coronary catheters.

Introduction of the vector preparation (4.0 ml containing about $10^{11}$ viral particles of adenovirus) was made by injecting 2.0 ml into both the left and right coronary arteries. Animals were anesthetized, and arterial access acquired via the right carotid by cut-down; a 5 F Cordis sheath was placed. A 5 F Multipurpose (A2) coronary catheter was used to engage the coronary arteries. The catheter tip was then placed 1 cm within the arterial lumen so that minimal material would be lost to the proximal aorta during injection. This procedure was carried out for each of the pigs.

Using these techniques, we have obtained very high efficiency gene delivery to the myocardium with no transgene expression observed in hepatocytes. Moreover, viral RNA could not be detected in the urine at any time after intracoronary injection.

As described in Example 13, such in vivo gene delivery of a β-ASP transgene to myocardium was found to substantially enhance cardiac function in our large mammal model.

Example 12-2
In vivo Gene Transfer of Other β-ASPs to Myocardium

Vectors comprising other β-ASPs, such as vectors encoding β-ARs or GRK inhibitors as described in Examples 6 and 7, can be used to deliver other preferred β-ASP transgenes using techniques as described in Example 12-1.

As described below, in vivo gene transfer of a first exemplary β-ASP transgene (AC) had a substantial and positive impact on cardiac function in our large animal model.

Delivery of other β-ASP transgenes can be used in place of, or in addition to, delivery of an AC transgene. Where a combination of β-ASP transgenes is supplied, the combination can be provided in a single vector (comprising two or more β-ASP transgenes) or in separate vectors (each comprising a β-ASP transgene). With size-constrained vectors such as adenovirus, an additional β-ASP transgene (such as a GRK inhibitor) can be accommodated in the vector by deleting an additional replication gene such as E4, as described above. Moreover, newer generations of such viral vectors are being used in which size-constraints are relieved in additional ways. In addition, a number of available non-viral vectors such as lipid-based vectors (including, e.g., cationic liposome complexes) do not exhibit such restrictive size constraints as observed with viral particle vectors.

Such additional β-ASPs can also be delivered using separate vectors. Where separate vectors are used, the vectors can be introduced together in a single injection (such as illustrated above) or in separate injections. While such separate vectors providing different transgenes are most conveniently analogous vectors (in which one β-ASP transgene is effectively replaced with another), different promoters can be employed as well as different base vectors.

The following example demonstrates the effect of in vivo β-ASP transgene delivery on cardiac function in our porcine model of heart failure.

Example 13
Increased Cardiac Function After in vivo Gene Transfer to Large Animal Models Predictive of CHF in Humans Pigs that had received an exemplary β-adrenergic signaling protein via in vivo gene therapy as described in Example 12-1 above were examined for cardiac function and other criteria, both before and after gene delivery.

Mismatch analyses confirmed that the β-ASP transgene (murine $AC_{VI}$) was present in the myocardium of animals that had received the gene transfer.

A number of indicators of cardiac function were measured before and after gene transfer. Briefly, conscious animals were suspended in a sling and pressures from the LV (n=1), LA and aorta were monitored, and electrocardiograms were recorded in digital format on-line (at rest and during atrial pacing at 150 bpm). Two-dimensional and M-mode images were obtained using a Hewlett Packard ultrasound imaging system. Images were obtained from a right parasternal approach at the mid-papillary muscle level and recorded on VHS tape. Images were recorded with animals in a basal state and again during right atrial pacing (HR=150 bpm). These studies were performed one day prior to gene transfer and were then repeated at 7±3 days after transfer. Rate-pressure products and left atrial pressures were found to be similar before and after gene transfer, indicating similar myocardial oxygen demands and loading conditions. Echocardiographic measurements were made using standardized criteria (Sahn, et al. Circulation 58:1072, 1978). The left ventricular end-diastolic diameter (EDD) and end-systolic diameter (ESD) were measured from 5 continuous beats and averaged.

Left ventricular fractional shortening (% FS) was also examined [(EDD-ESD)/EDD]×100. This measure was unchanged by gene transfer, indicating no deleterious effects of the intervention, and demonstrating the safety of the procedure. To demonstrate reproducibility of echocardiographic measurements, animals (n=5) were imaged on two consecutive days, showing high correlation ($r^2$=0.90; p=0.005).

After left ventricular dimensions had been measured and baseline hemodynamics recorded, glycopyrrolate (a muscarinic cholinergic antagonist) was given (at 0.14 mg/kg, by i.v.) in order to block the effects of the parasympathetic nervous system on heart rate responses. Isoproterenol was then delivered in bolus doses into the pulmonary artery catheter as heart rate responses were recorded. These studies were conducted one day prior to gene transfer and then again 5–10 days after gene transfer in each pig. Data were then examined by paired analyses comparing each animal before and after gene transfer.

Figure 10:
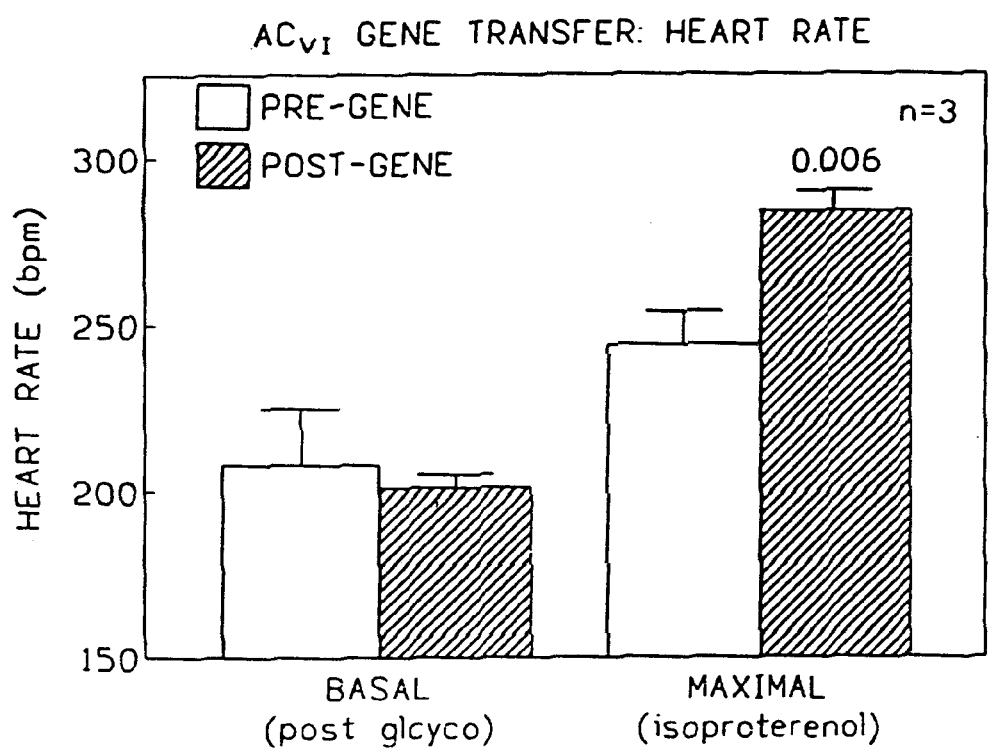
FIG. 10 shows data summarizing the effects of in vivo gene transfer of $AC_{VI}$ on heart rate in pigs, as described in Example 13. These data demonstrate, for the first time, that in vivo gene transfer can effectively increase adrenergic responsiveness in a large mammal heart.
Figure 11:
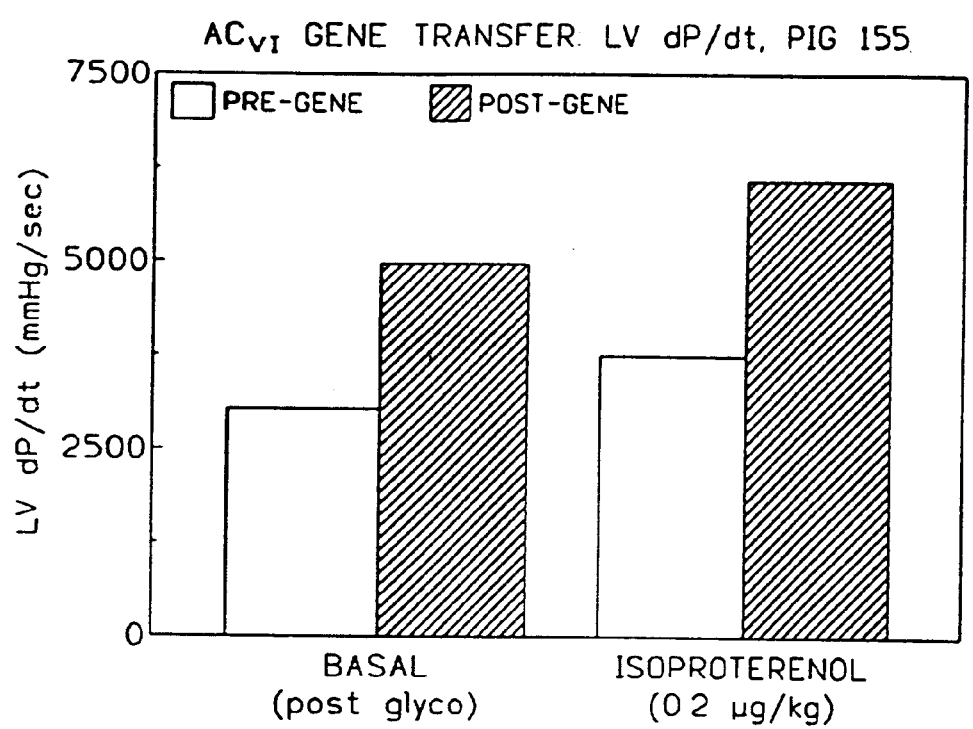
FIG. 11 shows results of in vivo gene transfer of $AC_{VI}$ on left ventricular (LV) dP/dt in a normal pig, as described in Example 13. These data further demonstrate that in vivo gene transfer of an adrenergic signaling element (in this case $AC_{VI}$) can effectively enhance contractile function of the intact heart in a large animal model that is considered highly predictive of human cardiac function.

The results, as shown in FIGS. 10 and 11, demonstrated that in vivo gene delivery of even a single β-ASP transgene according to the present invention effectively increased β-adrenergic responsiveness in a large animal model heart that is predictive of humans.

FIG. 10 shows data summarizing the effects of in vivo gene transfer of $AC_{VI}$ on heart rate. Animals were studied before and 5–10 days after intracoronary delivery of $10^{11}$ viral particles of an adenovirus expressing $AC_{VI}$. Glycopyrrolate was used to remove parasympathetic influences on heart rate, thereby optimally isolating the myocardial βAR pathway. Basal heart rate was unchanged, but maximal (isoproterenol-stimulated) heart rate was increased significantly by in vivo delivery of a β-ASP transgene (i.e. $AC_{VI}$) according to the present invention. These data demonstrate, for the first time, that in vivo gene transfer of a β-ASP transgene can effectively increase β-adrenergic responsiveness in a large mammal heart.

FIG. 11 shows results of in vivo gene transfer of $AC_{VI}$ on LV dP/dt in a normal pig. The animal was studied before and 7 days after intracoronary delivery of $10^{12}$ viral particles of an adenovirus carrying the β-ASP transgene $AC_{VI}$.

Glycopyrrolate was used to remove parasympathetic influences on contractile function, thereby optimally isolating the myocardial βAR pathway.

As shown in FIG. 11, basal LV dP/dt was substantially increased at the same basal heart rate. Response to isoproterenol was also increased after $AC_{VI}$ gene transfer. These data demonstrate that in vivo gene transfer of an illustrative β-ASP transgene can effectively increase contractile function of the intact heart in a large animal model expected to predictive of cardiac function in humans.

In summary, the foregoing studies demonstrated that the use of in vivo gene therapy to deliver even a single β-ASP transgene according to the present invention effectively increased endogenous β-adrenergic responsiveness and cardiac function in a mammalian heart that has been observed to mimic cardiac function, and dysfunction, in humans.

As noted previously, β-ASP gene constructs can also be modified to alter the effective levels of expression of the resulting transgene being employed in the context of the present invention. For example, as described above, expression of β-ASP transgenes can be altered by placing the transgene under the control of a heterologous promoter (including, for example, various constitutive or inducible promoters, as well as tissue-specific promoters such as cardiac-specific promoters). As also described above, expression can be altered by changing other regions of the genes, including, for example, the untranslated regions of such genes. By way of illustration, $AC_{VI}$ constructs having deletions in the 3'-untranslated region can be generated (as described in Example 5-3), and tested for their relative ability to affect expression and functional responsiveness in cardiac cells (as illustrated in Example 8-2). The ability to employ genes exhibiting differing levels of expression provides an added tool that can be used to readily tailor and optimize the present invention in the context of varying therapeutic needs (e.g., depending on the desired level of expression in the cells and tissue to be treated), and can also be used to reduce the amount of vector required to generate a given physiological effect. As further described above, it is possible to obtain human isoforms of β-ASP transgenes using techniques such as those illustrated in Example 5-3. The illustrations presented in Examples 9–13 provide additional guidance as to means for testing and using such β-ASP transgenes in the context of the present invention.

In addition, considering these demonstrated effects in conjunction with our observations and others' regarding the effective coupling of various components in the βAR-$G_s$-AC pathway, the ability to deliver β-ARs, GRK inhibitors or combinations of such β-ASPs in accordance with the present invention (as described above) is expected to provide an even greater enhancement of endogenous β-adrenergic responsiveness and cardiac function in such dysfunctional mammalian hearts. Indeed our data described above support the idea that alterations in β-ARs and proteins affecting β-ARs (such as GRK) are important early contributors to the abnormalities in responsiveness to endogenous β-adrenergic agonists that are observed in association with CHF.

By providing means for effectively enhancing responsiveness to endogenous β-adrenergic agonists, the methods and compositions of the present invention thus provide greatly-needed alternatives to the use of exogenous pharmacological agonists and other methods for the treatment of congestive heart failure in humans.

Various particularly preferred embodiments of the present invention are described above and generally claimed below. The invention now being fully described herein, it will be apparent to those of ordinary skill in the art that many changes and modifications can be made to this invention without departing from the spirit or scope of the invention as presently claimed.

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 314 base pairs
      (B) TYPE: nucleic acid
      (C) STRANDEDNESS: double
      (D) TOPOLOGY: linear

```
    (ix) FEATURE:
          (A) NAME/KEY: Coding Sequence
          (B) LOCATION: 1...312
          (D) OTHER INFORMATION:

(xi) SEQUENCE DESCRIPTION: SEQ ID NO:1:

ATG TCA TGG TTT AGT GGC CTC CTG GTC CCT AAA GTG GAT GAA CGG AAA         48
Met Ser Trp Phe Ser Gly Leu Leu Val Pro Lys Val Asp Glu Arg Lys
1               5                   10                  15

ACA GCC TGG GGT GAA CGC AAT GGG CAG AAG CGT TCG CGG CGC CGT GGC         96
Thr Ala Trp Gly Glu Arg Asn Gly Gln Lys Arg Ser Arg Arg Arg Gly
                20                  25                  30

ACT CGG GCA GGT GGC TTC TGC ACG CCC CGC TAT ATG AGC TGC CTC CGG        144
Thr Arg Ala Gly Gly Phe Cys Thr Pro Arg Tyr Met Ser Cys Leu Arg
            35                  40                  45

GAT GCA GAG CCA CCC AGC CCC ACC CCT GCG GGC CCC CCT CGG TGC CCC        192
Asp Ala Glu Pro Pro Ser Pro Thr Pro Ala Gly Pro Pro Arg Cys Pro
        50                  55                  60

TGG CAG GAT GAC GCC TTC ATC CGG AGG GGC GGC CCA NGC AAG GGC AAG        240
Trp Gln Asp Asp Ala Phe Ile Arg Arg Gly Gly Pro Xaa Lys Gly Lys
65                  70                  75                  80

GAA CTG GGG CTG CGG GCA GTG GCC CTG GGC TTC GAA GAT ACC GAA GTG        288
Glu Leu Gly Leu Arg Ala Val Ala Leu Gly Phe Glu Asp Thr Glu Val
                85                  90                  95

ACA ACG ACA CCG GCG GGA CCG CTG AA                                     314
Thr Thr Thr Pro Ala Gly Pro Leu
            100

(2) INFORMATION FOR SEQ ID NO:2:

(i) SEQUENCE CHARACTERISTICS:
        (A) LENGTH: 104 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:2:

Met Ser Trp Phe Ser Gly Leu Leu Val Pro Lys Val Asp Glu Arg Lys
1               5                   10                  15

Thr Ala Trp Gly Glu Arg Asn Gly Gln Lys Arg Ser Arg Arg Arg Gly
                20                  25                  30

Thr Arg Ala Gly Gly Phe Cys Thr Pro Arg Tyr Met Ser Cys Leu Arg
            35                  40                  45

Asp Ala Glu Pro Pro Ser Pro Thr Pro Ala Gly Pro Pro Arg Cys Pro
        50                  55                  60

Trp Gln Asp Asp Ala Phe Ile Arg Arg Gly Gly Pro Xaa Lys Gly Lys
65                  70                  75                  80

Glu Leu Gly Leu Arg Ala Val Ala Leu Gly Phe Glu Asp Thr Glu Val
                85                  90                  95

Thr Thr Thr Pro Ala Gly Pro Leu
            100

(2) INFORMATION FOR SEQ ID NO:3:

(i) SEQUENCE CHARACTERISTICS:
        (A) LENGTH: 1812 base pairs
        (B) TYPE: nucleic acid
        (C) STRANDEDNESS: double
        (D) TOPOLOGY: linear
```

(ix) FEATURE:
    (A) NAME/KEY: Coding Sequence
    (B) LOCATION: 1...1812
    (D) OTHER INFORMATION:

(xi) SEQUENCE DESCRIPTION: SEQ ID NO:3:

```
GTT AAC GTG GTG CTG GGC ATC CTG GCG GCA GTG CAG GTC GGG GGC GCT       48
Val Asn Val Val Leu Gly Ile Leu Ala Ala Val Gln Val Gly Gly Ala
 1               5                  10                  15

TTC GCA GCA GAC CCG CGC AGC CCC TCT GCG GGC CTC TGG TGC CCT GTG       96
Phe Ala Ala Asp Pro Arg Ser Pro Ser Ala Gly Leu Trp Cys Pro Val
             20                  25                  30

TTC TTT GTA TAC ATC GCA TAC ACG CTC CTC CCC ATC CGC ATG CGG GCT      144
Phe Phe Val Tyr Ile Ala Tyr Thr Leu Leu Pro Ile Arg Met Arg Ala
         35                  40                  45

GCC GTC CTC AGC GGC CTG GGC CTC TCC ACC TTG CAT TTG ATC TTG GCC      192
Ala Val Leu Ser Gly Leu Gly Leu Ser Thr Leu His Leu Ile Leu Ala
     50                  55                  60

TGG CAA CTT AAC CGT GGT GAT GCC TTC CTC TGG AAG CAG CTC GGT GCC      240
Trp Gln Leu Asn Arg Gly Asp Ala Phe Leu Trp Lys Gln Leu Gly Ala
 65                  70                  75                  80

AAT GTG CTG CTG TTC CTC TGC ACC AAC GTC ATT AGC ATC TGC ACA CAC      288
Asn Val Leu Leu Phe Leu Cys Thr Asn Val Ile Ser Ile Cys Thr His
                 85                  90                  95

TAT CCA GCA GAG GTG TCT CAG CGC CAG GCC TTT CAG GAG ACC CGC AGT      336
Tyr Pro Ala Glu Val Ser Gln Arg Gln Ala Phe Gln Glu Thr Arg Ser
            100                 105                 110

TAC ATC CAG GCC CGG CTC CAC CTG CAG CAT GAG AAT CGG CAG CAG GAG      384
Tyr Ile Gln Ala Arg Leu His Leu Gln His Glu Asn Arg Gln Gln Glu
        115                 120                 125

CGG CTG CTG CTG TCG GTA TTG CCC CAG CAC GTT GCC ATG GAG ATG AAA      432
Arg Leu Leu Leu Ser Val Leu Pro Gln His Val Ala Met Glu Met Lys
    130                 135                 140

GAA GAC ATC AAC ACA AAA AAA GAA GAC ATG TTC CAC AAG ATC TAC ATA      480
Glu Asp Ile Asn Thr Lys Lys Glu Asp Met Phe His Lys Ile Tyr Ile
145                 150                 155                 160

CAG AAG CAT GAC AAT GTC AGC ATC CTG TTT GCA GAC ATT GAG GGC TTC      528
Gln Lys His Asp Asn Val Ser Ile Leu Phe Ala Asp Ile Glu Gly Phe
                165                 170                 175

ACC AGC CTG GCA TCC CAG TGC ACT GCG CAG GAG CTG GTC ATG ACC CTG      576
Thr Ser Leu Ala Ser Gln Cys Thr Ala Gln Glu Leu Val Met Thr Leu
            180                 185                 190

AAT GAG CTC TTT GCC CGG TTT GAC AAG CTG GCT GCG GAG AAT CAC TGC      624
Asn Glu Leu Phe Ala Arg Phe Asp Lys Leu Ala Ala Glu Asn His Cys
        195                 200                 205

CTG AGG ATC AAG ATC TTG GGG GAC TGT TAC TAC TGT GTG TCA GGG CTG      672
Leu Arg Ile Lys Ile Leu Gly Asp Cys Tyr Tyr Cys Val Ser Gly Leu
    210                 215                 220

CCG GAG GCC CGG GCC GAC CAT GCC CAC TGC TGT GTG GAG ATG GGG GTA      720
Pro Glu Ala Arg Ala Asp His Ala His Cys Cys Val Glu Met Gly Val
225                 230                 235                 240

GAC ATG ATT GAG GCC ATC TCG CTG GTA CGT GAG GTG ACA GGT GTG AAT      768
Asp Met Ile Glu Ala Ile Ser Leu Val Arg Glu Val Thr Gly Val Asn
                245                 250                 255

GTG AAC ATG CGC GTG GGC ATC CAC AGC GGG CGC GTG CAC TGC GGC GTC      816
Val Asn Met Arg Val Gly Ile His Ser Gly Arg Val His Cys Gly Val
            260                 265                 270

CTT GGC TTG CGG AAA TGG CAG TTC GAT GTG TGG TCC AAT GAT GTG ACC      864
Leu Gly Leu Arg Lys Trp Gln Phe Asp Val Trp Ser Asn Asp Val Thr
        275                 280                 285
```

```
CTG GCC AAC CAC ATG GAA GCA GGA AGC CGG GCT GGC CGC ATC CAC ATC      912
Leu Ala Asn His Met Glu Ala Gly Ser Arg Ala Gly Arg Ile His Ile
    290                 295                 300

ACT CGG GCA ACA CTG CAG TAC CTG AAC GGG GAC TAC GAA GTG GAG CCA      960
Thr Arg Ala Thr Leu Gln Tyr Leu Asn Gly Asp Tyr Glu Val Glu Pro
305                 310                 315                 320

GGC CGT GGT GGC AAG CGC AAC GCG TAC CTC AAG GAG CAG CAC ATT GAG     1008
Gly Arg Gly Gly Lys Arg Asn Ala Tyr Leu Lys Glu Gln His Ile Glu
                325                 330                 335

ACT TTC CTC ATC CTG GGC GCC AGC CAG AAA CGG AAA GAG GAG AAA GGC     1056
Thr Phe Leu Ile Leu Gly Ala Ser Gln Lys Arg Lys Glu Glu Lys Gly
    340                 345                 350

ATG CTG GCC AAG CTG CAG CGG ACT CGG GCC AAC TCC ATG GAA GGG CTG     1104
Met Leu Ala Lys Leu Gln Arg Thr Arg Ala Asn Ser Met Glu Gly Leu
355                 360                 365

ATG CCG CGA TGG GTT CCT GAT CGT GCC TTC TCC CGG ACC AAG GAC TCC     1152
Met Pro Arg Trp Val Pro Asp Arg Ala Phe Ser Arg Thr Lys Asp Ser
                370                 375                 380

AAG GCC TTC CGC CAG ATG GGC ATT GAT GAT TCC AGC AAA GAC AAC CGG     1200
Lys Ala Phe Arg Gln Met Gly Ile Asp Asp Ser Ser Lys Asp Asn Arg
385                 390                 395                 400

GGC ACC CAA GAT GCC CTG AAC CCT GAG GAT GAG GTG GAT GAG TTC CTG     1248
Gly Thr Gln Asp Ala Leu Asn Pro Glu Asp Glu Val Asp Glu Phe Leu
                405                 410                 415

AGC CGT GCC ATC GAT GCC CGC AGC ATT GAT CAG CTG CGG AAG GAC CAT     1296
Ser Arg Ala Ile Asp Ala Arg Ser Ile Asp Gln Leu Arg Lys Asp His
                420                 425                 430

GTG CGC CGG TTT TTG CTC ACC TTC CAG AGA GAG GAT TTT GAG AAG AAG     1344
Val Arg Arg Phe Leu Leu Thr Phe Gln Arg Glu Asp Phe Glu Lys Lys
        435                 440                 445

TAC TCC CGG AAG GTG GAT CCC CGC TTC GGA GCC TAC GTT GCC TGT GCC     1392
Tyr Ser Arg Lys Val Asp Pro Arg Phe Gly Ala Tyr Val Ala Cys Ala
    450                 455                 460

CTG TTG GTC TTC TGC TTC ATC TGC TTC ATC CAG CTT CTA ATT TTC CCA     1440
Leu Leu Val Phe Cys Phe Ile Cys Phe Ile Gln Leu Leu Ile Phe Pro
465                 470                 475                 480

CAC TCC ACC CTG ATG CTT GGG ATT TAT GCC AGC ATC TTC CTG CTG CTG     1488
His Ser Thr Leu Met Leu Gly Ile Tyr Ala Ser Ile Phe Leu Leu Leu
                485                 490                 495

CTA ATC ACC GTG CTG ATC TGT GCT GTG TAC TCC TGT GGT TCT CTG TTC     1536
Leu Ile Thr Val Leu Ile Cys Ala Val Tyr Ser Cys Gly Ser Leu Phe
            500                 505                 510

CCT AAG GCC CTG CAA CGT CTG TCC CGC AGC ATT GTC CGC TCA CGG GCA     1584
Pro Lys Ala Leu Gln Arg Leu Ser Arg Ser Ile Val Arg Ser Arg Ala
                515                 520                 525

CAT AGC ACC GCA GTT GGC ATC TTT TCC GTC CTG CTT GTG TTT ACT TCT     1632
His Ser Thr Ala Val Gly Ile Phe Ser Val Leu Leu Val Phe Thr Ser
                530                 535                 540

GCC ATT GCC AAC ATG TTC ACC TGT AAC CAC ACC CCC ATA CGG AGC TGT     1680
Ala Ile Ala Asn Met Phe Thr Cys Asn His Thr Pro Ile Arg Ser Cys
545                 550                 555                 560

GCA GCC CGG ATG CTG AAT TTA ACA CCT GCT GAC ATC ACT GCC TGC CAC     1728
Ala Ala Arg Met Leu Asn Leu Thr Pro Ala Asp Ile Thr Ala Cys His
                565                 570                 575

CTG CAG CAG CTC AAT TAC TCT CTG GGC CTG GAT GCT CCC CTG TGT GAG     1776
Leu Gln Gln Leu Asn Tyr Ser Leu Gly Leu Asp Ala Pro Leu Cys Glu
            580                 585                 590

GGC ACC ATG CCC ACC TGC AGC TTT CCT GAG GTG TTC                     1812
Gly Thr Met Pro Thr Cys Ser Phe Pro Glu Val Phe
595                 600
```

(2) INFORMATION FOR SEQ ID NO:4:

(i) SEQUENCE CHARACTERISTICS:
        (A) LENGTH: 604 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:4:

```
Val Asn Val Val Leu Gly Ile Leu Ala Ala Val Gln Val Gly Gly Ala
 1               5                  10                  15

Phe Ala Ala Asp Pro Arg Ser Pro Ser Ala Gly Leu Trp Cys Pro Val
            20                  25                  30

Phe Phe Val Tyr Ile Ala Tyr Thr Leu Leu Pro Ile Arg Met Arg Ala
            35                  40                  45

Ala Val Leu Ser Gly Leu Gly Leu Ser Thr Leu His Leu Ile Leu Ala
50                  55                  60

Trp Gln Leu Asn Arg Gly Asp Ala Phe Leu Trp Lys Gln Leu Gly Ala
65                  70                  75                  80

Asn Val Leu Leu Phe Leu Cys Thr Asn Val Ile Ser Ile Cys Thr His
                85                  90                  95

Tyr Pro Ala Glu Val Ser Gln Arg Gln Ala Phe Gln Glu Thr Arg Ser
            100                 105                 110

Tyr Ile Gln Ala Arg Leu His Leu Gln His Glu Asn Arg Gln Gln Glu
            115                 120                 125

Arg Leu Leu Leu Ser Val Leu Pro Gln His Val Ala Met Glu Met Lys
130                 135                 140

Glu Asp Ile Asn Thr Lys Lys Glu Asp Met Phe His Lys Ile Tyr Ile
145                 150                 155                 160

Gln Lys His Asp Asn Val Ser Ile Leu Phe Ala Asp Ile Glu Gly Phe
                165                 170                 175

Thr Ser Leu Ala Ser Gln Cys Thr Ala Gln Glu Leu Val Met Thr Leu
            180                 185                 190

Asn Glu Leu Phe Ala Arg Phe Asp Lys Leu Ala Ala Glu Asn His Cys
            195                 200                 205

Leu Arg Ile Lys Ile Leu Gly Asp Cys Tyr Tyr Cys Val Ser Gly Leu
210                 215                 220

Pro Glu Ala Arg Ala Asp His Ala His Cys Cys Val Glu Met Gly Val
225                 230                 235                 240

Asp Met Ile Glu Ala Ile Ser Leu Val Arg Glu Val Thr Gly Val Asn
                245                 250                 255

Val Asn Met Arg Val Gly Ile His Ser Gly Arg Val His Cys Gly Val
            260                 265                 270

Leu Gly Leu Arg Lys Trp Gln Phe Asp Val Trp Ser Asn Asp Val Thr
            275                 280                 285

Leu Ala Asn His Met Glu Ala Gly Ser Arg Ala Gly Arg Ile His Ile
290                 295                 300

Thr Arg Ala Thr Leu Gln Tyr Leu Asn Gly Asp Tyr Glu Val Glu Pro
305                 310                 315                 320

Gly Arg Gly Gly Lys Arg Asn Ala Tyr Leu Lys Glu Gln His Ile Glu
                325                 330                 335

Thr Phe Leu Ile Leu Gly Ala Ser Gln Lys Arg Lys Glu Glu Lys Gly
            340                 345                 350
```

```
Met Leu Ala Lys Leu Gln Arg Thr Arg Ala Asn Ser Met Glu Gly Leu
            355                 360                 365

Met Pro Arg Trp Val Pro Asp Arg Ala Phe Ser Arg Thr Lys Asp Ser
        370                 375                 380

Lys Ala Phe Arg Gln Met Gly Ile Asp Asp Ser Ser Lys Asp Asn Arg
385                 390                 395                 400

Gly Thr Gln Asp Ala Leu Asn Pro Glu Asp Glu Val Asp Glu Phe Leu
                405                 410                 415

Ser Arg Ala Ile Asp Ala Arg Ser Ile Asp Gln Leu Arg Lys Asp His
            420                 425                 430

Val Arg Arg Phe Leu Leu Thr Phe Gln Arg Glu Asp Phe Glu Lys Lys
        435                 440                 445

Tyr Ser Arg Lys Val Asp Pro Arg Phe Gly Ala Tyr Val Ala Cys Ala
    450                 455                 460

Leu Leu Val Phe Cys Phe Ile Cys Phe Ile Gln Leu Leu Ile Phe Pro
465                 470                 475                 480

His Ser Thr Leu Met Leu Gly Ile Tyr Ala Ser Ile Phe Leu Leu Leu
                485                 490                 495

Leu Ile Thr Val Leu Ile Cys Ala Val Tyr Ser Cys Gly Ser Leu Phe
            500                 505                 510

Pro Lys Ala Leu Gln Arg Leu Ser Arg Ser Ile Val Arg Ser Arg Ala
        515                 520                 525

His Ser Thr Ala Val Gly Ile Phe Ser Val Leu Leu Val Phe Thr Ser
    530                 535                 540

Ala Ile Ala Asn Met Phe Thr Cys Asn His Thr Pro Ile Arg Ser Cys
545                 550                 555                 560

Ala Ala Arg Met Leu Asn Leu Thr Pro Ala Asp Ile Thr Ala Cys His
                565                 570                 575

Leu Gln Gln Leu Asn Tyr Ser Leu Gly Leu Asp Ala Pro Leu Cys Glu
            580                 585                 590

Gly Thr Met Pro Thr Cys Ser Phe Pro Glu Val Phe
        595                 600

(2) INFORMATION FOR SEQ ID NO:5:

(i) SEQUENCE CHARACTERISTICS:
        (A) LENGTH: 3549 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 1...3501
        (D) OTHER INFORMATION:

(xi) SEQUENCE DESCRIPTION: SEQ ID NO:5:

ATG TCA TGG TTT AGT GGC CTC CTG GTC CCT AAA GTG GAT GAA CGG AAA        48
Met Ser Trp Phe Ser Gly Leu Leu Val Pro Lys Val Asp Glu Arg Lys
 1               5                  10                  15

ACA GCC TGG GGT GAA CGC AAT GGG CAG AAG CGT TCG CGG CGC CGT GGC        96
Thr Ala Trp Gly Glu Arg Asn Gly Gln Lys Arg Ser Arg Arg Arg Gly
             20                  25                  30

ACT CGG GCA GGT GGC TTC TGC ACG CCC CGC TAT ATG AGC TGC CTC CGG       144
Thr Arg Ala Gly Gly Phe Cys Thr Pro Arg Tyr Met Ser Cys Leu Arg
         35                  40                  45

GAT GCA GAG CCA CCC AGC CCC ACC CCT GCG GGC CCC CCT CGG TGC CCC       192
Asp Ala Glu Pro Pro Ser Pro Thr Pro Ala Gly Pro Pro Arg Cys Pro
     50                  55                  60
```

-continued

```
TGG CAG GAT GAC GCC TTC ATC CGG AGG GGC GGC CCA GGC AAG GGC AAG     240
Trp Gln Asp Asp Ala Phe Ile Arg Arg Gly Gly Pro Gly Lys Gly Lys
 65                  70                  75                  80

GAG CTG GGG CTG CGG GCA GTG GCC CTG GGC TTC GAG GAT ACC GAG GTG     288
Glu Leu Gly Leu Arg Ala Val Ala Leu Gly Phe Glu Asp Thr Glu Val
                 85                  90                  95

ACA ACG ACA GCG GGC GGG ACG GCT GAG GTG GCG CCC GAC GCG GTG CCC     336
Thr Thr Thr Ala Gly Gly Thr Ala Glu Val Ala Pro Asp Ala Val Pro
            100                 105                 110

AGG AGT GGG CGA TCC TGC TGG CGC CGT TTG GTG CAG GTG TTC CAG TCG     384
Arg Ser Gly Arg Ser Cys Trp Arg Arg Leu Val Gln Val Phe Gln Ser
        115                 120                 125

AAG CAG TTC CGT TCG GCC AAG CTG GAG CGC CTG TAC CAG CGG TAC TTT     432
Lys Gln Phe Arg Ser Ala Lys Leu Glu Arg Leu Tyr Gln Arg Tyr Phe
130                 135                 140

TTC CAG ATG AAC CAG AGC AGC CTG ACG CTG CTG GTG GCG GTG CTG GTG     480
Phe Gln Met Asn Gln Ser Ser Leu Thr Leu Leu Val Ala Val Leu Val
145                 150                 155                 160

CTG CTC ACA GCG GTG CTG CTG GCT TTC CAA GCC GCA CCC GCC CGC CCT     528
Leu Leu Thr Ala Val Leu Leu Ala Phe Gln Ala Ala Pro Ala Arg Pro
                165                 170                 175

CAG CCT GCC TAT GTG GCA CTG TTG GCC TGT GCC GCC GCC CTG TTC GTG     576
Gln Pro Ala Tyr Val Ala Leu Leu Ala Cys Ala Ala Ala Leu Phe Val
            180                 185                 190

GGG CTC ATG GTG GTG TGT AAC CGG CAT AGC TTC CGC CAG GAC TCC ATG     624
Gly Leu Met Val Val Cys Asn Arg His Ser Phe Arg Gln Asp Ser Met
        195                 200                 205

TGG GTG GTG AGT AAC GTG GTG CTG GGC ATC CTG GCG GCA GTG CAG GTC     672
Trp Val Val Ser Asn Val Val Leu Gly Ile Leu Ala Ala Val Gln Val
210                 215                 220

GGG GGC GCT TTC GCA GCA GAC CCG CGC AGC CCC TCT GCG GGC CTC TGG     720
Gly Gly Ala Phe Ala Ala Asp Pro Arg Ser Pro Ser Ala Gly Leu Trp
225                 230                 235                 240

TGC CCT GTG TTC TTT GTA TAC ATC GCA TAC ACG CTC CTC CCC ATC CGC     768
Cys Pro Val Phe Phe Val Tyr Ile Ala Tyr Thr Leu Leu Pro Ile Arg
                245                 250                 255

ATG CGG GCT GCC GTC CTC AGC GGC CTG GGC CTC TCC ACC TTG CAT TTG     816
Met Arg Ala Ala Val Leu Ser Gly Leu Gly Leu Ser Thr Leu His Leu
            260                 265                 270

ATC TTG GCC TGG CAA CTT AAC CGT GGT GAT GCC TTC CTC TGG AAG CAG     864
Ile Leu Ala Trp Gln Leu Asn Arg Gly Asp Ala Phe Leu Trp Lys Gln
        275                 280                 285

CTC GGT GCC AAT GTG CTG CTG TTC CTC TGC ACC AAC GTC ATT AGC ATC     912
Leu Gly Ala Asn Val Leu Leu Phe Leu Cys Thr Asn Val Ile Ser Ile
290                 295                 300

TGC ACA CAC TAT CCA GCA GAG GTG TCT CAG CGC CAG GCC TTT CAG GAG     960
Cys Thr His Tyr Pro Ala Glu Val Ser Gln Arg Gln Ala Phe Gln Glu
305                 310                 315                 320

ACC CGC AGT TAC ATC CAG GCC CGG CTC CAC CTG CAG CAT GAG AAT CGG    1008
Thr Arg Ser Tyr Ile Gln Ala Arg Leu His Leu Gln His Glu Asn Arg
                325                 330                 335

CAG CAG GAG CGG CTG CTG CTG TCG GTA TTG CCC CAG CAC GTT GCC ATG    1056
Gln Gln Glu Arg Leu Leu Leu Ser Val Leu Pro Gln His Val Ala Met
            340                 345                 350

GAG ATG AAA GAA GAC ATC AAC ACA AAA AAA GAA GAC ATG TTC CAC AAG    1104
Glu Met Lys Glu Asp Ile Asn Thr Lys Lys Glu Asp Met Phe His Lys
        355                 360                 365

ATC TAC ATA CAG AAG CAT GAC AAT GTC AGC ATC CTG TTT GCA GAC ATT    1152
Ile Tyr Ile Gln Lys His Asp Asn Val Ser Ile Leu Phe Ala Asp Ile
370                 375                 380
```

-continued

```
GAG GGC TTC ACC AGC CTG GCA TCC CAG TGC ACT GCG CAG GAG CTG GTC      1200
Glu Gly Phe Thr Ser Leu Ala Ser Gln Cys Thr Ala Gln Glu Leu Val
385                 390                 395                 400

ATG ACC CTG AAT GAG CTC TTT GCC CGG TTT GAC AAG CTG GCT GCG GAG      1248
Met Thr Leu Asn Glu Leu Phe Ala Arg Phe Asp Lys Leu Ala Ala Glu
                405                 410                 415

AAT CAC TGC CTG AGG ATC AAG ATC TTG GGG GAC TGT TAC TAC TGT GTG      1296
Asn His Cys Leu Arg Ile Lys Ile Leu Gly Asp Cys Tyr Tyr Cys Val
            420                 425                 430

TCA GGG CTG CCG GAG GCC CGG GCC GAC CAT GCC CAC TGC TGT GTG GAG      1344
Ser Gly Leu Pro Glu Ala Arg Ala Asp His Ala His Cys Cys Val Glu
                435                 440                 445

ATG GGG GTA GAC ATG ATT GAG GCC ATC TCG CTG GTA CGT GAG GTG ACA      1392
Met Gly Val Asp Met Ile Glu Ala Ile Ser Leu Val Arg Glu Val Thr
        450                 455                 460

GGT GTG AAT GTG AAC ATG CGC GTG GGC ATC CAC AGC GGG CGT GTG CAC      1440
Gly Val Asn Val Asn Met Arg Val Gly Ile His Ser Gly Arg Val His
465                 470                 475                 480

TGC GGC GTC CTT GGC TTG CGG AAA TGG CAG TTC GAT GTG TGG TCC AAT      1488
Cys Gly Val Leu Gly Leu Arg Lys Trp Gln Phe Asp Val Trp Ser Asn
                485                 490                 495

GAT GTG ACC CTG GCC AAC CAC ATG GAA GCA GGA AGC CGG GCT GGC CGC      1536
Asp Val Thr Leu Ala Asn His Met Glu Ala Gly Ser Arg Ala Gly Arg
            500                 505                 510

ATC CAC ATC ACT CGG GCA ACA CTG CAG TAC CTG AAC GGG GAC TAC GAA      1584
Ile His Ile Thr Arg Ala Thr Leu Gln Tyr Leu Asn Gly Asp Tyr Glu
                515                 520                 525

GTG GAG CCA GGC CGT GGT GGC AAG CGC AAC GCG TAC CTC AAG GAG CAG      1632
Val Glu Pro Gly Arg Gly Gly Lys Arg Asn Ala Tyr Leu Lys Glu Gln
530                 535                 540

CAC ATT GAG ACT TTC CTC ATC CTG GGC GCC AGC CAG AAA CGG AAA GAG      1680
His Ile Glu Thr Phe Leu Ile Leu Gly Ala Ser Gln Lys Arg Lys Glu
545                 550                 555                 560

GAG AAA GGC ATG CTG GCC AAG CTG CAG CGG ACT CGG GCC AAC TCC ATG      1728
Glu Lys Gly Met Leu Ala Lys Leu Gln Arg Thr Arg Ala Asn Ser Met
                565                 570                 575

GAA GGG CTG ATG CCG CGA TGG GTT CCT GAT CGT GCC TTC TCC CGG ACC      1776
Glu Gly Leu Met Pro Arg Trp Val Pro Asp Arg Ala Phe Ser Arg Thr
            580                 585                 590

AAG GAC TCC AAG GCC TTC CGC CAG ATG GGC ATT GAT GAT TCC AGC AAA      1824
Lys Asp Ser Lys Ala Phe Arg Gln Met Gly Ile Asp Asp Ser Ser Lys
                595                 600                 605

GAC AAC CGG GGC ACC CAA GAT GCC CTG AAC CCT GAG GAT GAG GTG GAT      1872
Asp Asn Arg Gly Thr Gln Asp Ala Leu Asn Pro Glu Asp Glu Val Asp
610                 615                 620

GAG TTC CTG AGC CGT GCC ATC GAT GCC CGC AGC ATT GAT CAG CTG CGG      1920
Glu Phe Leu Ser Arg Ala Ile Asp Ala Arg Ser Ile Asp Gln Leu Arg
625                 630                 635                 640

AAG GAC CAT GTG CGC CGG TTT TTG CTC ACC TTC CAG AGA GAG GAT TTT      1968
Lys Asp His Val Arg Arg Phe Leu Leu Thr Phe Gln Arg Glu Asp Phe
                645                 650                 655

GAG AAG AAG TAC TCC CGG AAG GTG GAT CCC CGC TTC GGA GCC TAC GTT      2016
Glu Lys Lys Tyr Ser Arg Lys Val Asp Pro Arg Phe Gly Ala Tyr Val
            660                 665                 670

GCC TGT GCC CTG TTG GTC TTC TGC TTC ATC TGC TTC ATC CAG CTT CTA      2064
Ala Cys Ala Leu Leu Val Phe Cys Phe Ile Cys Phe Ile Gln Leu Leu
                675                 680                 685

ATT TTC CCA CAC TCC ACC CTG ATG CTT GGG ATT TAT GCC AGC ATC TTC      2112
Ile Phe Pro His Ser Thr Leu Met Leu Gly Ile Tyr Ala Ser Ile Phe
            690                 695                 700
```

-continued

```
CTG CTG CTG CTA ATC ACC GTG CTG ATC TGT GCT GTG TAC TCC TGT GGT        2160
Leu Leu Leu Leu Ile Thr Val Leu Ile Cys Ala Val Tyr Ser Cys Gly
705                 710                 715                 720

TCT CTG TTC CCT AAG GCC CTG CAA CGT CTG TCC CGC AGC ATT GTC CGC        2208
Ser Leu Phe Pro Lys Ala Leu Gln Arg Leu Ser Arg Ser Ile Val Arg
            725                 730                 735

TCA CGG GCA CAT AGC ACC GCA GTT GGC ATC TTT TCC GTC CTG CTT GTG        2256
Ser Arg Ala His Ser Thr Ala Val Gly Ile Phe Ser Val Leu Leu Val
                740                 745                 750

TTT ACT TCT GCC ATT GCC AAC ATG TTC ACC TGT AAC CAC ACC CCC ATA        2304
Phe Thr Ser Ala Ile Ala Asn Met Phe Thr Cys Asn His Thr Pro Ile
                    755                 760                 765

CGG AGC TGT GCA GCC CGG ATG CTG AAT TTA ACA CCT GCT GAC ATC ACT        2352
Arg Ser Cys Ala Ala Arg Met Leu Asn Leu Thr Pro Ala Asp Ile Thr
770                 775                 780

GCC TGC CAC CTG CAG CAG CTC AAT TAC TCT CTG GGC CTG GAT GCT CCC        2400
Ala Cys His Leu Gln Gln Leu Asn Tyr Ser Leu Gly Leu Asp Ala Pro
785                 790                 795                 800

CTG TGT GAG GGC ACC ATG CCC ACC TGC AGC TTT CCT GAG GTG TCC ATC        2448
Leu Cys Glu Gly Thr Met Pro Thr Cys Ser Phe Pro Glu Val Ser Ile
                805                 810                 815

GGG AAC ATG CTG CTG AGT CTC TTG GCC AGC TCT GTC TTC CTG CAC ATC        2496
Gly Asn Met Leu Leu Ser Leu Leu Ala Ser Ser Val Phe Leu His Ile
                    820                 825                 830

AGC AGC ATC GGG AAG TTG GCC ATG ATC TTT GTC TTG GGG CTC ATC TAT        2544
Ser Ser Ile Gly Lys Leu Ala Met Ile Phe Val Leu Gly Leu Ile Tyr
                        835                 840                 845

TTG GTG CTG CTT CTG CTG GGT CCC CCA GCC GCC ATC TTT GAC AAC TAT        2592
Leu Val Leu Leu Leu Leu Gly Pro Pro Ala Ala Ile Phe Asp Asn Tyr
850                 855                 860

GAC CTA CTG CTT GGC GTC CAT GGC TTG GCT TCT TCC AAT GAG ACC TTT        2640
Asp Leu Leu Leu Gly Val His Gly Leu Ala Ser Ser Asn Glu Thr Phe
865                 870                 875                 880

GAT GGG CTG GAC TGT CCA GCT GCA GGG AGG GTG GCC CTC AAA TAT ATG        2688
Asp Gly Leu Asp Cys Pro Ala Ala Gly Arg Val Ala Leu Lys Tyr Met
                885                 890                 895

ACC CCT GTG ATT CTG CTG GTG TTT GCG CTG GCG CTG TAT CTG CAT GCT        2736
Thr Pro Val Ile Leu Leu Val Phe Ala Leu Ala Leu Tyr Leu His Ala
                    900                 905                 910

CAG CAG GTG GAA TCG ACT GCC CGC CTA AAC TTC CTC TGG AAA CTA CAG        2784
Gln Gln Val Glu Ser Thr Ala Arg Leu Asn Phe Leu Trp Lys Leu Gln
                        915                 920                 925

GCA ACA GGG GAA AAA GAG GAG ATG GAG GAG CTA CAG GCA TAC AAC CGG        2832
Ala Thr Gly Glu Lys Glu Glu Met Glu Glu Leu Gln Ala Tyr Asn Arg
930                 935                 940

AGG CTG CTG CAT AAC ATT CTG CCC AAG GAC GTG GCG GCC CAC TTC CTG        2880
Arg Leu Leu His Asn Ile Leu Pro Lys Asp Val Ala Ala His Phe Leu
945                 950                 955                 960

GCC CGG GAG CGC CGC AAT GAT GAA CTC TAC TAT CAG TCG TGT GAG TGT        2928
Ala Arg Glu Arg Arg Asn Asp Glu Leu Tyr Tyr Gln Ser Cys Glu Cys
                965                 970                 975

GTG GCT GTT ATG TTT GCC TCC ATT GCC AAC TTC TCT GAG TTC TAT GTG        2976
Val Ala Val Met Phe Ala Ser Ile Ala Asn Phe Ser Glu Phe Tyr Val
                    980                 985                 990

GAG CTG GAG GCA AAC AAT GAG GGT GCC GAG TGC CTG CGG CTG CTC AAC        3024
Glu Leu Glu Ala Asn Asn Glu Gly Ala Glu Cys Leu Arg Leu Leu Asn
                        995                 1000                1005

GAG ATC ATC GCT GAC TTT GAT GAG ATT ATC AGC GAG GAG CGG TTC CGG        3072
Glu Ile Ile Ala Asp Phe Asp Glu Ile Ile Ser Glu Glu Arg Phe Arg
        1010                1015                1020
```

-continued

```
CAG CTG GAA AAG ATC AAG ACG ATT GGT AGC ACC TAC ATG GCT GCC TCA    3120
Gln Leu Glu Lys Ile Lys Thr Ile Gly Ser Thr Tyr Met Ala Ala Ser
025                 1030                1035                1040

GGG CTG AAC GCC AGC ACC TAC GAT CAG GTG GGC CGC TCC CAC ATC ACT    3168
Gly Leu Asn Ala Ser Thr Tyr Asp Gln Val Gly Arg Ser His Ile Thr
                1045                1050                1055

GCC CTG GCT GAC TAC GCC ATG CGG CTC ATG GAG CAG ATG AAG CAC ATC    3216
Ala Leu Ala Asp Tyr Ala Met Arg Leu Met Glu Gln Met Lys His Ile
            1060                1065                1070

AAT GAG CAC TCC TTC AAC AAT TTC CAG ATG AAG ATT GGG CTG AAC ATG    3264
Asn Glu His Ser Phe Asn Asn Phe Gln Met Lys Ile Gly Leu Asn Met
        1075                1080                1085

GGC CCA GTC GTG GCA GGT GTC ATC GGG GCT CGG AAG CCA CAG TAT GAC    3312
Gly Pro Val Val Ala Gly Val Ile Gly Ala Arg Lys Pro Gln Tyr Asp
    1090                1095                1100

ATC TGG GGG AAC ACA GTG AAT GTC TCT AGT CGT ATG GAC AGC ACG GGG    3360
Ile Trp Gly Asn Thr Val Asn Val Ser Ser Arg Met Asp Ser Thr Gly
105                 1110                1115                1120

GTC CCC GAC CGA ATC CAG GTG ACC ACG GAC CTG TAC CAG GTT CTA GCT    3408
Val Pro Asp Arg Ile Gln Val Thr Thr Asp Leu Tyr Gln Val Leu Ala
                1125                1130                1135

GCC AAG GGC TAC CAG CTG GAG TGT CGA GGG GTG GTC AAG GTG AAG GGC    3456
Ala Lys Gly Tyr Gln Leu Glu Cys Arg Gly Val Val Lys Val Lys Gly
            1140                1145                1150

AAG GGG GAG ATG ACC ACC TAC TTC CTC AAT GGG GGC CCC AGC AGT TAACA 3506
Lys Gly Glu Met Thr Thr Tyr Phe Leu Asn Gly Gly Pro Ser Ser
        1155                1160                1165

GGGCCCAGCC ACAAATTCAG CTGAAGGGAC CAAGGTGGGC ACT                    3549
```

(2) INFORMATION FOR SEQ ID NO:6:

(i) SEQUENCE CHARACTERISTICS:
        (A) LENGTH: 1167 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:6:

```
Met Ser Trp Phe Ser Gly Leu Leu Val Pro Lys Val Asp Glu Arg Lys
1               5                   10                  15

Thr Ala Trp Gly Glu Arg Asn Gly Gln Lys Arg Ser Arg Arg Arg Gly
            20                  25                  30

Thr Arg Ala Gly Gly Phe Cys Thr Pro Arg Tyr Met Ser Cys Leu Arg
        35                  40                  45

Asp Ala Glu Pro Pro Ser Pro Thr Pro Ala Gly Pro Pro Arg Cys Pro
50                  55                  60

Trp Gln Asp Asp Ala Phe Ile Arg Arg Gly Gly Pro Gly Lys Gly Lys
65                  70                  75                  80

Glu Leu Gly Leu Arg Ala Val Ala Leu Gly Phe Glu Asp Thr Glu Val
                85                  90                  95

Thr Thr Thr Ala Gly Gly Thr Ala Glu Val Ala Pro Asp Ala Val Pro
            100                 105                 110

Arg Ser Gly Arg Ser Cys Trp Arg Arg Leu Val Gln Val Phe Gln Ser
        115                 120                 125

Lys Gln Phe Arg Ser Ala Lys Leu Glu Arg Leu Tyr Gln Arg Tyr Phe
    130                 135                 140
```

```
-continued

Phe Gln Met Asn Gln Ser Ser Leu Thr Leu Leu Val Ala Val Leu Val
145                 150                 155                 160

Leu Leu Thr Ala Val Leu Leu Ala Phe Gln Ala Ala Pro Ala Arg Pro
            165                 170                 175

Gln Pro Ala Tyr Val Ala Leu Leu Ala Cys Ala Ala Ala Leu Phe Val
            180                 185                 190

Gly Leu Met Val Val Cys Asn Arg His Ser Phe Arg Gln Asp Ser Met
        195                 200                 205

Trp Val Ser Asn Val Val Leu Gly Ile Leu Ala Ala Val Gln Val
    210                 215                 220

Gly Gly Ala Phe Ala Ala Asp Pro Arg Ser Pro Ser Ala Gly Leu Trp
225                 230                 235                 240

Cys Pro Val Phe Phe Val Tyr Ile Ala Tyr Thr Leu Leu Pro Ile Arg
                245                 250                 255

Met Arg Ala Ala Val Leu Ser Gly Leu Gly Leu Ser Thr Leu His Leu
        260                 265                 270

Ile Leu Ala Trp Gln Leu Asn Arg Gly Asp Ala Phe Leu Trp Lys Gln
            275                 280                 285

Leu Gly Ala Asn Val Leu Leu Phe Leu Cys Thr Asn Val Ile Ser Ile
    290                 295                 300

Cys Thr His Tyr Pro Ala Glu Val Ser Gln Arg Gln Ala Phe Gln Glu
305                 310                 315                 320

Thr Arg Ser Tyr Ile Gln Ala Arg Leu His Leu Gln His Glu Asn Arg
                325                 330                 335

Gln Gln Glu Arg Leu Leu Leu Ser Val Leu Pro Gln His Val Ala Met
        340                 345                 350

Glu Met Lys Glu Asp Ile Asn Thr Lys Lys Glu Asp Met Phe His Lys
            355                 360                 365

Ile Tyr Ile Gln Lys His Asp Asn Val Ser Ile Leu Phe Ala Asp Ile
    370                 375                 380

Glu Gly Phe Thr Ser Leu Ala Ser Gln Cys Thr Ala Gln Glu Leu Val
385                 390                 395                 400

Met Thr Leu Asn Glu Leu Phe Ala Arg Phe Asp Lys Leu Ala Ala Glu
                405                 410                 415

Asn His Cys Leu Arg Ile Lys Ile Leu Gly Asp Cys Tyr Tyr Cys Val
        420                 425                 430

Ser Gly Leu Pro Glu Ala Arg Ala Asp His Ala His Cys Cys Val Glu
            435                 440                 445

Met Gly Val Asp Met Ile Glu Ala Ile Ser Leu Val Arg Glu Val Thr
    450                 455                 460

Gly Val Asn Val Asn Met Arg Val Gly Ile His Ser Gly Arg Val His
465                 470                 475                 480

Cys Gly Val Leu Gly Leu Arg Lys Trp Gln Phe Asp Val Trp Ser Asn
                485                 490                 495

Asp Val Thr Leu Ala Asn His Met Glu Ala Gly Ser Arg Ala Gly Arg
        500                 505                 510

Ile His Ile Thr Arg Ala Thr Leu Gln Tyr Leu Asn Gly Asp Tyr Glu
            515                 520                 525

Val Glu Pro Gly Arg Gly Gly Lys Arg Asn Ala Tyr Leu Lys Glu Gln
    530                 535                 540

His Ile Glu Thr Phe Leu Ile Leu Gly Ala Ser Gln Lys Arg Lys Glu
545                 550                 555                 560
```

-continued

```
Glu Lys Gly Met Leu Ala Lys Leu Gln Arg Thr Arg Ala Asn Ser Met
                565                 570                 575

Glu Gly Leu Met Pro Arg Trp Val Pro Asp Arg Ala Phe Ser Arg Thr
                580                 585                 590

Lys Asp Ser Lys Ala Phe Arg Gln Met Gly Ile Asp Asp Ser Ser Lys
                595                 600                 605

Asp Asn Arg Gly Thr Gln Asp Ala Leu Asn Pro Glu Asp Glu Val Asp
            610                 615                 620

Glu Phe Leu Ser Arg Ala Ile Asp Ala Arg Ser Ile Asp Gln Leu Arg
625                 630                 635                 640

Lys Asp His Val Arg Arg Phe Leu Leu Thr Phe Gln Arg Glu Asp Phe
                645                 650                 655

Glu Lys Lys Tyr Ser Arg Lys Val Asp Pro Arg Phe Gly Ala Tyr Val
                660                 665                 670

Ala Cys Ala Leu Leu Val Phe Cys Phe Ile Cys Phe Ile Gln Leu Leu
                675                 680                 685

Ile Phe Pro His Ser Thr Leu Met Leu Gly Ile Tyr Ala Ser Ile Phe
            690                 695                 700

Leu Leu Leu Leu Ile Thr Val Leu Ile Cys Ala Val Tyr Ser Cys Gly
705                 710                 715                 720

Ser Leu Phe Pro Lys Ala Leu Gln Arg Leu Ser Arg Ser Ile Val Arg
                725                 730                 735

Ser Arg Ala His Ser Thr Ala Val Gly Ile Phe Ser Val Leu Leu Val
                740                 745                 750

Phe Thr Ser Ala Ile Ala Asn Met Phe Thr Cys Asn His Thr Pro Ile
                755                 760                 765

Arg Ser Cys Ala Ala Arg Met Leu Asn Leu Thr Pro Ala Asp Ile Thr
770                 775                 780

Ala Cys His Leu Gln Gln Leu Asn Tyr Ser Leu Gly Leu Asp Ala Pro
785                 790                 795                 800

Leu Cys Glu Gly Thr Met Pro Thr Cys Ser Phe Pro Glu Val Ser Ile
                805                 810                 815

Gly Asn Met Leu Leu Ser Leu Leu Ala Ser Ser Val Phe Leu His Ile
                820                 825                 830

Ser Ser Ile Gly Lys Leu Ala Met Ile Phe Val Leu Gly Leu Ile Tyr
            835                 840                 845

Leu Val Leu Leu Leu Gly Pro Pro Ala Ala Ile Phe Asp Asn Tyr
850                 855                 860

Asp Leu Leu Leu Gly Val His Gly Leu Ala Ser Ser Asn Glu Thr Phe
865                 870                 875                 880

Asp Gly Leu Asp Cys Pro Ala Ala Gly Arg Val Ala Leu Lys Tyr Met
                885                 890                 895

Thr Pro Val Ile Leu Leu Val Phe Ala Leu Ala Leu Tyr Leu His Ala
                900                 905                 910

Gln Gln Val Glu Ser Thr Ala Arg Leu Asn Phe Leu Trp Lys Leu Gln
                915                 920                 925

Ala Thr Gly Glu Lys Glu Glu Met Glu Glu Leu Gln Ala Tyr Asn Arg
                930                 935                 940

Arg Leu Leu His Asn Ile Leu Pro Lys Asp Val Ala Ala His Phe Leu
945                 950                 955                 960

Ala Arg Glu Arg Arg Asn Asp Glu Leu Tyr Tyr Gln Ser Cys Glu Cys
                965                 970                 975
```

```
Val Ala Val Met Phe Ala Ser Ile Ala Asn Phe Ser Glu Phe Tyr Val
            980                 985                 990
Glu Leu Glu Ala Asn Asn Glu Gly Ala Glu Cys Leu Arg Leu Leu Asn
        995                1000                1005
Glu Ile Ile Ala Asp Phe Asp Glu Ile Ile Ser Glu Glu Arg Phe Arg
    1010                1015                1020
Gln Leu Glu Lys Ile Lys Thr Ile Gly Ser Thr Tyr Met Ala Ala Ser
025                 1030                1035                1040
Gly Leu Asn Ala Ser Thr Tyr Asp Gln Val Gly Arg Ser His Ile Thr
            1045                1050                1055
Ala Leu Ala Asp Tyr Ala Met Arg Leu Met Glu Gln Met Lys His Ile
            1060                1065                1070
Asn Glu His Ser Phe Asn Asn Phe Gln Met Lys Ile Gly Leu Asn Met
        1075                1080                1085
Gly Pro Val Val Ala Gly Val Ile Gly Ala Arg Lys Pro Gln Tyr Asp
    1090                1095                1100
Ile Trp Gly Asn Thr Val Asn Val Ser Ser Arg Met Asp Ser Thr Gly
105                 1110                1115                1120
Val Pro Asp Arg Ile Gln Val Thr Thr Asp Leu Tyr Gln Val Leu Ala
            1125                1130                1135
Ala Lys Gly Tyr Gln Leu Glu Cys Arg Gly Val Val Lys Val Lys Gly
            1140                1145                1150
Lys Gly Glu Met Thr Thr Tyr Phe Leu Asn Gly Gly Pro Ser Ser
        1155                1160                1165

(2) INFORMATION FOR SEQ ID NO:7:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ix) FEATURE:

(xi) SEQUENCE DESCRIPTION: SEQ ID NO:7:

ACGTAGAATT CGGRGAYTGT TAYTACTG                                            28

(2) INFORMATION FOR SEQ ID NO:8:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ix) FEATURE:

(xi) SEQUENCE DESCRIPTION: SEQ ID NO:8:

ACGTTAAGCT TCCASACRTC RAAYTGCCA                                           29

(2) INFORMATION FOR SEQ ID NO:9:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: Genomic RNA
```

```
        (ix) FEATURE:

(xi) SEQUENCE DESCRIPTION: SEQ ID NO:9:

UUAUUUAWW                                                                9
```

We claim:

1. A method of enhancing the cardiac function of a mammal with congestive heart failure comprising administering a replication-deficient adenoviral vector comprising a nucleic acid sequence encoding a cardiac adenylylcyclase (AC) protein operatively linked to a promoter, to at least one coronary artery of the mammal such that the cardiac AC protein is expressed in the myocardium and enhances the cardiac function of the mammal.

2. The method of claim 1, wherein said mammal is a human.

3. The method of claim 1, wherein the enhanced cardiac function of the mammal is contractile function of the heart.

4. The method of claim 1, wherein the enhanced cardiac function of the mammal is beta-adrenergic responsiveness.

5. The method of claim 1, wherein the enhanced cardiac function of the mammal is left ventricular dP/dt.

6. The method of claim 1, wherein the adenoviral vector is expressed in cardiac myocytes.

7. The metbod of claim 1 wherein the adenoviral vector is administered into at least one left and at least one right coronary artery of the mammal.

8. The method of claim 1, wherein the cardiac adenylylcyclase (AC) is AC isoform VI.

9. The method of claim 1, wherein the cardiac adenylylcyclase (AC) is murine AC isoform VI.

10. The method of claim 1, wherein the promoter is a heterologous constitutive promoter.

11. The method of claim 1, wheran the promoter is a CMV promotor.

12. The method of claim 1, whercm the promoter is selected from the group consisting of a ventricular myosin light chain 2 promoter and a ventricular myosin heavy chain promoter.

13. The method of claim 1, wherein the nucleic acid encodes a cardiac AC which is a variant of a wild-type AC, the variant comprising a deletion in one or more untranslated regions of said AC.

14. The method of claim 13, wherein the nucleic acid encodes a cardiac AC which is a truncated $AC_{VI}$ having a deletion removing the 3' untranslated region.

15. A method of enhancing the cardiac function of a mammal with congestive heart failure comprising administering a replication-deficient adenoviral vector comprising a nucleic acid sequence encoding a cardiac adenylylcyclase (AC) protein operatively linked to a promoter, to at least one saphenous vein graft or mammary artery graft supply blood to the myocardium of the mammal such that the AC protein is expressed in the myocardium and enhaces the cardiac function of the mammal.

16. The method of claim 15, wherein said mammal is a human.

17. The method of claim 15, wherein the enhanced cardiac function of the mammal is contractile function of the heart.

18. The method of claim 15, wherein the enhanced cardiac function of the mammal is beta-adrenergic responsiveness.

19. The method of clalim 15, wherein the enhanced cardiac function of the mammal is left ventricular dP/dt.

20. The method of claim 15, wherein the adenoviral vector is expressed in cardiac myocytes.

21. The method of claim 15, wherein the cardiac adenylylcyclase (AC) is AC isoform VI.

22. The method of claim 21, wherein the nucleic acid encoding $AC_{VI}$ comprises a deletion in one or more untranslated regions of said $AC_{VI}$.

23. The method of claim 22, wherein said nucleic acid encoding an $AC_{VI}$ is a truncated $AC_{VI}$ having a deletion removing the 3' untranslated region.

24. The method of claim 15, wherein the cardiac adenylylcyclase (AC) is murine AC isoform VI.

25. The method of claim 15, wherein the promoter is a heterologous constitutive promoter.

26. The method of claim 15, wherein the promoter is a CMV promoter.

27. The method of claim 15, wherein the promoter is selected from the group consting of a ventricular myosin light chain 2 promoter and a ventricular myosin heavy chain promoter.

* * * * *

UNITED STATES PATENT AND TRADEMARK OFFICE
CERTIFICATE OF CORRECTION

PATENT NO. : 6,306,830 B1
DATED : October 23, 2001
INVENTOR(S) : H. Kirk Hammond et al.

It is certified that error appears in the above-identified patent and that said Letters Patent is hereby corrected as shown below:

Title page,
Item [63], please delete "Continuation-in-part of application No. 08/924,757, filed as application No. PCT/US97/15610 on Sept. 5, 1997, now abandoned." and insert
-- Continuation-in-part of application No. 08/924,757, filed Sept. 5, 1997, now abandoned, and of application No. PCT/US97/15610, filed on Sept. 5, 1997. --

Column 4,
Line 23, please delete "adenylycylase" and insert -- adenylylcyclase --;
Lines 46 and 49, please delete "transgenes" and insert -- transgene --;

Column 9,
Line 58, please delete "transgenes" and insert -- transgene --;

Column 16,
Lines 2, 16 and 18, please delete "transgenes" and insert -- transgene --;
Line 58, please delete "effect or" and insert -- effector --;

Column 18,
Line 5, please delete "transgenes" and insert -- transgene --;

Column 19,
Lines 3, 6 and 10, please delete "transgenes" and insert -- transgene --;
Lines 20-21, please delete "trans-genes" and insert -- trans-gene --;

Column 20,
Lines 51, 54 and 57, delete "Feigner" and insert -- Felgner --;

Column 51,
Line 1, delete "pmoleslug" and insert -- p moles/µg --;
Line 31, delete "llacZ" and insert -- lacZ --;
Line 31, delete "Jysed" and insert -- lysed --;

Column 54,
Line 19, before "ASP" insert -- β --;

UNITED STATES PATENT AND TRADEMARK OFFICE
CERTIFICATE OF CORRECTION

PATENT NO. : 6,306,830 B1
DATED : October 23, 2001
INVENTOR(S) : H. Kirk Hammond et al.

It is certified that error appears in the above-identified patent and that said Letters Patent is hereby corrected as shown below:

<u>Column 83,</u>
Line 38, delete "wheran" and insert -- wherein --;
Line 38, delete "promotor" and insert -- promoter --;
Line 40, delete "whcrcm" and insert -- wherein --;

<u>Column 84,</u>
Line 15, delete "supply" and insert -- supplying --; and
Line 15, delete "enhaces" and insert -- enhances --.

Signed and Sealed this

Thirteenth Day of August, 2002

*Attest:*

JAMES E. ROGAN
*Attesting Officer*   *Director of the United States Patent and Trademark Office*